United States Patent
Feng et al.

(10) Patent No.: US 7,528,137 B2
(45) Date of Patent: May 5, 2009

(54) COMPOUNDS, COMPOSITIONS, AND METHODS

(75) Inventors: Bainian Feng, Foster City, CA (US); Gustave Bergnes, Pacificia, CA (US); David J. Morgans, Jr., Los Altos, CA (US); Dashyant Dhanak, West Chester, PA (US); Steven David Knight, West Chester, PA (US); Michael Gerard Darcy, Philadelphia, PA (US)

(73) Assignees: Cytokinetics, Inc., South San Francisco, CA (US); SmithKline Beecham Corporation, Philadelphia, PA (US)

( * ) Notice: Subject to any disclaimer, the term of this patent is extended or adjusted under 35 U.S.C. 154(b) by 176 days.

(21) Appl. No.: 11/262,506

(22) Filed: Oct. 27, 2005

(65) Prior Publication Data

US 2006/0094735 A1    May 4, 2006

Related U.S. Application Data

(63) Continuation of application No. 10/435,069, filed on May 8, 2003, now Pat. No. 7,214,800.

(60) Provisional application No. 60/379,531, filed on May 9, 2002.

(51) Int. Cl.
C07D 271/02   (2006.01)
C07D 291/00   (2006.01)
C07D 239/70   (2006.01)

(52) U.S. Cl. .................. 514/258.1; 544/1; 544/224; 544/253; 544/240; 548/125

(58) Field of Classification Search .............. 548/125; 544/1, 224, 253, 240
See application file for complete search history.

(56) References Cited

U.S. PATENT DOCUMENTS

| | | |
|---|---|---|
| 3,320,124 A | 5/1967 | Waletzky et al. |
| 3,322,756 A | 5/1967 | Ruschig et al. |
| 3,723,432 A | 3/1973 | Ott et al. |
| 3,740,442 A | 6/1973 | Ott et al. |
| 3,846,549 A | 11/1974 | Mentrup et al. |
| 3,925,548 A | 12/1975 | Oh |
| 3,962,244 A | 6/1976 | Weyer et al. |
| 4,011,324 A | 3/1977 | Althuis |
| 4,281,127 A | 7/1981 | LeMahieu et al. |
| 4,670,560 A | 6/1987 | Press et al. |
| 4,729,996 A | 3/1988 | Wright et al. |
| 4,734,419 A | 3/1988 | Hashimoto et al. |
| 4,808,590 A | 2/1989 | Higa et al. |
| 4,857,530 A | 8/1989 | Berman et al. |
| 4,859,670 A | 8/1989 | Kampe et al. |
| 4,866,084 A | 9/1989 | Gunasekera et al. |
| 4,970,226 A | 11/1990 | Sun et al. |
| 4,981,856 A | 1/1991 | Hughes |
| 4,992,550 A | 2/1991 | Hughes |
| 5,037,829 A | 8/1991 | Freyne et al. |
| 5,081,124 A | 1/1992 | Hughes |
| 5,147,875 A | 9/1992 | Coates |
| 5,158,959 A | 10/1992 | Geiger et al. |
| 5,187,167 A | 2/1993 | Hughes |
| 5,204,354 A | 4/1993 | Chakravarty et al. |
| 5,264,439 A | 11/1993 | Greenlee et al. |
| 5,280,027 A | 1/1994 | Andrew et al. |
| 5,316,906 A | 5/1994 | Haughland et al. |
| 5,330,987 A | 7/1994 | Allen et al. |
| 5,342,944 A | 8/1994 | Mohan et al. |
| 5,401,766 A | 3/1995 | Geiger et al. |
| 5,430,148 A | 7/1995 | Webber et al. |
| 5,444,061 A | 8/1995 | Bisset et al. |
| 5,449,678 A | 9/1995 | Pines et al. |
| 5,470,878 A | 11/1995 | Michnick et al. |
| 5,492,915 A | 2/1996 | Dereu et al. |
| 5,561,133 A | 10/1996 | Bisset et al. |
| 5,574,057 A | 11/1996 | Ireland et al. |
| 5,707,992 A | 1/1998 | Webber et al. |
| 5,714,493 A | 2/1998 | Myers et al. |
| 5,747,498 A | 5/1998 | Schnur et al. |
| 5,753,664 A | 5/1998 | Aono et al. |
| 5,756,450 A | 5/1998 | Hahn et al. |
| 5,756,502 A | 5/1998 | Padia |
| 5,756,510 A | 5/1998 | Griffin et al. |
| 5,770,595 A | 6/1998 | Klein et al. |
| 5,773,476 A | 6/1998 | Chen et al. |
| 5,777,115 A | 7/1998 | Leigh et al. |

(Continued)

FOREIGN PATENT DOCUMENTS

| | | |
|---|---|---|
| AU | B-12617/88 | 9/1988 |
| EP | 0 056 637 A1 | 7/1982 |
| EP | 0 286 813 A2 | 2/1988 |
| EP | 0 341 990 A3 | 11/1989 |
| EP | 0 341 990 B1 | 11/1989 |
| EP | 0 360 417 A2 | 3/1990 |
| EP | 0 360 417 A3 | 3/1990 |
| EP | 0 373 891 A2 | 6/1990 |
| EP | 0 431 945 A2 | 6/1991 |
| EP | 0 481 614 A1 | 4/1992 |
| EP | 0 509 643 A1 | 10/1992 |
| EP | 0 512 676 A1 | 11/1992 |

(Continued)

OTHER PUBLICATIONS

International Search Report and Written Opinion mailed Oct. 21, 2005, for PCT Application No. PCT/US05/19791, filed Jun. 7, 2005.

(Continued)

*Primary Examiner*—James O. Wilson
*Assistant Examiner*—Paul V. Ward
(74) *Attorney, Agent, or Firm*—Finnegan, Henderson, Farabow, Garrett & Dunner, LLP

(57) ABSTRACT

Compounds useful for treating cellular proliferative diseases and disorders by modulating the activity of KSP are disclosed.

20 Claims, No Drawings

U.S. PATENT DOCUMENTS

| | | | |
|---|---|---|---|
| 5,780,476 A | 7/1998 | Underiner |
| 5,783,577 A | 7/1998 | Houghten et al. |
| 5,789,427 A | 8/1998 | Chen et al. |
| 5,795,898 A | 8/1998 | Brown et al. |
| 5,801,181 A | 9/1998 | Michnick et al. |
| 5,801,182 A | 9/1998 | Klein et al. |
| 5,804,584 A | 9/1998 | Underiner et al. |
| 5,807,861 A | 9/1998 | Klein et al. |
| 5,807,862 A | 9/1998 | Klein et al. |
| 5,811,429 A | 9/1998 | Connell et al. |
| 5,817,662 A | 10/1998 | Klein et al. |
| 5,837,703 A | 11/1998 | Kumar et al. |
| 5,852,024 A | 12/1998 | Pines et al. |
| 5,859,018 A | 1/1999 | Brown et al. |
| 5,869,665 A | 2/1999 | Padia |
| 5,885,996 A | 3/1999 | Webber et al. |
| 5,891,879 A | 4/1999 | Nagler et al. |
| 5,892,114 A | 4/1999 | Goldmann et al. |
| 5,922,866 A | 7/1999 | Miyata et al. |
| 5,929,081 A | 7/1999 | Brown et al. |
| 5,939,421 A | 8/1999 | Palanki et al. |
| 5,948,775 A | 9/1999 | Koko et al. |
| 5,948,784 A | 9/1999 | Fujiwara et al. |
| 6,008,010 A | 12/1999 | Greenberger et al. |
| 6,136,812 A | 10/2000 | Chenard et al. |
| 6,156,758 A | 12/2000 | Kung et al. |
| 6,207,403 B1 | 3/2001 | Goldstein et al. |
| 6,214,879 B1 | 4/2001 | Abraham et al. |
| 6,245,768 B1 | 6/2001 | He et al. |
| 6,518,277 B1 | 2/2003 | Sadhu et al. |
| 6,545,004 B1 | 4/2003 | Finer et al. |
| 6,545,005 B1 | 4/2003 | Baxter et al. |
| 6,559,160 B1 | 5/2003 | Schall et al. |
| 6,562,831 B1 | 5/2003 | Finer et al. |
| 6,596,723 B1 | 7/2003 | Watkins et al. |
| 6,613,798 B1 | 9/2003 | Porter et al. |
| 6,627,755 B1 | 9/2003 | Chenard et al. |
| 6,630,479 B1 | 10/2003 | Finer et al. |
| 6,753,428 B2 | 6/2004 | Bergnes et al. |
| 6,794,379 B2 | 9/2004 | Medina et al. |
| 6,831,085 B1 | 12/2004 | Bergnes et al. |
| 7,214,800 B2 | 5/2007 | Feng et al. |
| 2001/0046997 A1 | 11/2001 | Abraham et al. |
| 2002/0032207 A1 | 3/2002 | Thompson et al. |
| 2002/0055519 A1 | 5/2002 | Thompson et al. |
| 2002/0165221 A1 | 11/2002 | Baxter et al. |
| 2002/0169159 A1 | 11/2002 | Medina et al. |
| 2002/0198326 A1 | 12/2002 | Aoyama et al. |
| 2003/0018038 A1 | 1/2003 | Thompson et al. |
| 2003/0055054 A1 | 3/2003 | Medina et al. |
| 2003/0091946 A1 | 5/2003 | Uchira et al. |
| 2003/0096813 A1 | 5/2003 | Cao et al. |
| 2003/0119834 A1 | 6/2003 | Bamdad |
| 2003/0119854 A1 | 6/2003 | Schall et al. |
| 2003/0130293 A1 | 7/2003 | Bamdad |
| 2003/0139398 A1 | 7/2003 | Hoekstra et al. |
| 2003/0139457 A1 | 7/2003 | Baxter et al. |
| 2003/0144350 A1 | 7/2003 | Stevenson et al. |
| 2003/0158188 A1 | 8/2003 | Lee et al. |
| 2003/0158198 A1 | 8/2003 | Lee et al. |
| 2003/0166933 A1 | 9/2003 | Bergnes et al. |
| 2003/0171387 A1 | 9/2003 | Sun et al. |
| 2003/0195211 A1 | 10/2003 | Sadhu et al. |
| 2003/0220338 A1 | 11/2003 | Watkins et al. |
| 2003/0220356 A1 | 11/2003 | Ibrahim et al. |
| 2004/0023996 A1 | 2/2004 | Finer et al. |
| 2004/0048853 A1 | 3/2004 | Bergnes |
| 2004/0067969 A1 | 4/2004 | Bergnes et al. |
| 2004/0077662 A1 | 4/2004 | Zhou et al. |
| 2004/0077667 A1 | 4/2004 | Matsuoka et al. |
| 2004/0077668 A1 | 4/2004 | Feng et al. |
| 2004/0082567 A1 | 4/2004 | McDonald et al. |
| 2004/0092561 A1 | 5/2004 | Ruckle et al. |
| 2004/0116438 A1 | 6/2004 | Lu et al. |
| 2004/0142949 A1 | 7/2004 | Bergnes et al. |
| 2004/0192913 A1 | 9/2004 | Bergnes et al. |
| 2004/0198724 A1 | 10/2004 | McNaughton-Smith et al. |
| 2004/0242596 A1 | 12/2004 | Kim et al. |
| 2004/0259826 A1 | 12/2004 | Fraley et al. |
| 2005/0059823 A1 | 3/2005 | McNaughton-Smith et al. |
| 2005/0152940 A1 | 7/2005 | Hezi-Yamit et al. |
| 2005/0209254 A1 | 9/2005 | Wang et al. |

FOREIGN PATENT DOCUMENTS

| | | |
|---|---|---|
| EP | 0 534 706 A1 | 3/1993 |
| EP | 0 537 937 A2 | 4/1993 |
| EP | 0 884 310 A1 | 12/1998 |
| EP | 0 884 316 A1 | 12/1998 |
| EP | 0 884 319 A2 | 12/1998 |
| EP | 0 884 319 A3 | 12/1998 |
| EP | 0 900 568 A2 | 3/1999 |
| EP | 0 903 344 A1 | 3/1999 |
| EP | 1 072 952 A1 | 1/2000 |
| EP | 1 174 430 A1 | 1/2002 |
| GB | 2271111 A | 4/1994 |
| HU | 184797 | 10/1984 |
| JP | 62-135473 | 6/1987 |
| JP | 06049070 A2 | 2/1994 |
| JP | 06-148835 | 5/1994 |
| JP | 10/259176 | 9/1998 |
| WO | WO 91/12001 A1 | 8/1991 |
| WO | WO 93/11115 A2 | 6/1993 |
| WO | WO 93/19051 A1 | 9/1993 |
| WO | WO 93/20055 A1 | 10/1993 |
| WO | WO 93/23404 A1 | 11/1993 |
| WO | WO 94/21259 A1 | 9/1994 |
| WO | WO 95/16682 A1 | 6/1995 |
| WO | WO 95/19169 A2 | 7/1995 |
| WO | WO 95/24379 A1 | 9/1995 |
| WO | WO 96/06616 A1 | 3/1996 |
| WO | WO 96/19224 A1 | 6/1996 |
| WO | WO 96/28430 A1 | 9/1996 |
| WO | WO 96/28444 A1 | 9/1996 |
| WO | WO 96/39403 A1 | 12/1996 |
| WO | WO 97/10221 A1 | 3/1997 |
| WO | WO 97/43276 A1 | 11/1997 |
| WO | WO 98/26664 A1 | 6/1998 |
| WO | WO 98/29410 A1 | 7/1998 |
| WO | WO 98/34613 A1 | 8/1998 |
| WO | WO 98/58947 A1 | 12/1998 |
| WO | WO 99/08501 A2 | 2/1999 |
| WO | WO 99/20298 A1 | 4/1999 |
| WO | WO 00/00491 A1 | 1/2000 |
| WO | WO 00/07017 A2 | 2/2000 |
| WO | WO 01/74344 A2 | 10/2000 |
| WO | WO 00/69827 A1 | 11/2000 |
| WO | WO 01/16114 A2 | 3/2001 |
| WO | WO 01/19800 A2 | 3/2001 |
| WO | WO 01/23364 A1 | 4/2001 |
| WO | WO 01/23365 A1 | 4/2001 |
| WO | WO 01/25235 A1 | 4/2001 |
| WO | WO 01/30768 A1 | 5/2001 |
| WO | WO 01/32171 A1 | 5/2001 |
| WO | WO 01/32634 A1 | 5/2001 |
| WO | WO 01/42216 A2 | 6/2001 |
| WO | WO 01/66519 A2 | 9/2001 |
| WO | WO 01/70737 A2 | 9/2001 |
| WO | WO 01/81346 A2 | 11/2001 |
| WO | WO 01/95884 A2 | 12/2001 |
| WO | WO 01/98278 A1 | 12/2001 |
| WO | WO 02/04444 A2 | 1/2002 |
| WO | WO 02/08224 A1 | 1/2002 |
| WO | WO 02/09713 A2 | 2/2002 |

| | | |
|---|---|---|
| WO | WO 02/09713 A3 | 2/2002 |
| WO | WO 02/14319 A2 | 2/2002 |
| WO | WO 02/30462 A2 | 4/2002 |
| WO | WO 02/083143 A1 | 10/2002 |
| WO | WO 02/094790 A1 | 11/2002 |
| WO | WO 03/020279 A2 | 3/2003 |
| WO | WO 03/020280 A2 | 3/2003 |
| WO | WO 03/027234 A2 | 4/2003 |
| WO | WO 03/035076 A1 | 5/2003 |
| WO | WO 03/035077 A1 | 5/2003 |
| WO | WO 03/039460 A2 | 5/2003 |
| WO | WO 03/043961 A2 | 5/2003 |
| WO | WO 03/043995 A1 | 5/2003 |
| WO | WO 03/049527 A2 | 6/2003 |
| WO | WO 03/049678 A2 | 6/2003 |
| WO | WO 03/049679 A2 | 6/2003 |
| WO | WO 03/050064 A2 | 6/2003 |
| WO | WO 03/050122 A2 | 6/2003 |
| WO | WO 03/063800 A2 | 8/2003 |
| WO | WO 03/070701 A2 | 8/2003 |
| WO | WO 03/070701 A3 | 8/2003 |
| WO | WO 03/076418 A1 | 9/2003 |
| WO | WO 03/079973 A2 | 10/2003 |
| WO | WO 03/084544 A2 | 10/2003 |
| WO | WO 03/094839 A2 | 11/2003 |
| WO | WO 03/097053 A1 | 11/2003 |
| WO | WO 03/099211 A2 | 12/2003 |
| WO | WO 03/103575 A2 | 12/2003 |
| WO | WO 03/105855 A1 | 12/2003 |
| WO | WO 03/106417 A1 | 12/2003 |
| WO | WO 03/106426 A1 | 12/2003 |
| WO | WO 03/106435 A1 | 12/2003 |
| WO | WO 2004/004652 A2 | 1/2004 |
| WO | WO 2004/006916 A1 | 1/2004 |
| WO | WO 2004/009036 A2 | 1/2004 |
| WO | WO 2004/018058 A2 | 3/2004 |
| WO | WO 2004/020599 A2 | 3/2004 |
| WO | WO 2004/022554 A1 | 3/2004 |
| WO | WO 2004/034972 A2 | 4/2004 |
| WO | WO 2004/039774 A2 | 5/2004 |
| WO | WO 2004/064741 A2 | 8/2004 |
| WO | WO 2004/078758 | 9/2004 |

OTHER PUBLICATIONS

Franco et al., "Functional association of retinoic acid and *hedgehog* signaling in *Xenopus* primary neurogenesis," *Development*, 126: 4257-4265 (1999).
Gaffield et al., "A Looking Glass Perspective: Thalidomide and Cyclopamine," *Cellular and Molecular Biology*, 45(5): 579-588 (1999).
Ghorab, "Synthesis of Some New Thiadiazole, Selena, Triazine, Thiazole and Cyanopyridine Derivatives with Assay for Their Antitumor Activity," *Phosphorus, Sulfur, and Silicon*, 112: 7-17 (1996).
Gailani et al., "The role of the human homologue of *Drosophilia* patched in sporadic basal cell carcinomas," *Nature Genetics*, 14: 78-81 (1996).
Ghorab et al., "Synthesis and effect of some new [1,2,4]triazolo[4,3-a]quinazolin-5(4H)-ones and related compounds on Ehrlich Ascites Carcinoma cells," *Acta Pharm.*, 49: 1-10 (1999).
Jiang et al., "Synthesis and Biological Evaluation of 2-Styrylquinazolin-4(3H)-ones, a New Class of Antimitotic Anticancer Agents Which Inhibit Tubulin Polymerization," *J. Med. Chem.*, 33: 1721-1728 (1990).
Smith et al., "Effects of Gastrin, Proglumide, and Somatostatin on Growth of Human Colon Cancer," *Gastroenterology*, 95: 1541-1548 (1988).
"Signal Transduction," from the *Dictionary of Biology*, Penguin Books, Ninth Edition reprinted with minor revisions, pp. 574-575 (1995).
"Hyper-," from *The British Medical Dictionary*, Caxton, p. 706 (circa 1961).
"Inhibit," from *The British Medical Dictionary*, Caxton, p. 747 (circa 1961).
Ghosh, "Quinazolines. Part I.," *J. Indian Chemical Society*, XIV: 411-413 (1937).
Mayer et al, "Small Molecule Inhibitor of Mitotic Spindle Bipolarity Identified in a Phenotype-Based Screen," *Science*, 286: 971-974 (1999).
Tortora et al., "Oral Administration of a Novel Taxane, an Antisense Oligonucleotide Targeting Protein Kinase A, and the Epidermal Growth Factor Receptor Inhibitor Iressa Causes Cooperative Antitumor and Antiangiogenic Activity," *Clinical Cancer Research*, 7: 4156-4163 (2001).
Guo et al., "Overexpression of Bax Enhances Antitumor Activity of Chemotherapeutic Agents in Human Head and Neck Squamous Cell Carcinoma," *Clinical Cancer Research*, 6: 718-724 (2000).
Simone, "Oncology: Introduction," *Cecil Textbook of Medicine, 20th Edition*, 1: 1004-1010 (1996).
Farrell et al., "The role of ATP hydrolysis for kinesin processivity," PubMed Abstract only, *J Biol Chem*, 277(19): 17079-17087 (2002).
Yildiz et al., "Kinesin: walking, crawling or sliding along?" *TRENDS in Cell Biology*, 15(2): 112-120 (2005).
Office Action mailed Dec. 5, 2005, for U.S. Appl. No. 10/429,195, filed May 2, 2003.
Office Action mailed Dec. 6, 2005, for U.S. Appl. No. 10/644,244, filed Aug. 20, 2003.
Office Action mailed Dec. 20, 2005, for U.S. Appl. No. 10/893,929, filed Jul. 20, 2004.
Chemcats Copyright 2000 ACS, 1998:596123 Chemcats, Maybridge, Apr. 3, 2000, DP 01489, "N2-(3-pyridylmethyl)-4-oxo-3,4-dihydroquinazoline-2-carboxamide," 190437-46-8, Chemical Library.
Q. Kozhevnikov et al. 4-Quinazolinones. II. 2-(Aminomethyl)-3-aryl-4-quinazolinones. (Russian) Tr Perm Sel-Khoz Inst. 79: 66-72 (1971). *Chem Abstracts* 78: 390 (1973).
Gupta, C.M. et al. "Drugs acting on the central nervous system. Synthesis of substituted quinazolones and quinazolines and triazepino- and triazocinoquinazolones," *J. Med. Chem.* 11: 392-395 (1968).
Saari, W.S. et al. "Synthesis and evaluation of 2-pyridinone dervatives as HIV-1-specific reverse transcriptase inhibitors. 2. Analogues of 3-aminopyridin-2(1H)-one," *J. Med. Chem.* 35: 3792-3802 (1992).
Farghaly, A.M. et al. "Non-steroidal anti-inflammatory agents. III: Synthesis of pyrazole derivatives of 4(3H)-quinazolinones," *Alexandria J. Pharm. Sci.* 4(1): 52-56 (1990).
Dymek, W. et al. "2-Chloromethyl-6-methylquinazolone-4 and its transformations," *Diss. Pharm. Et Pharmacol.* 20(1): 29-34 (1968).
Pattanaik, J.M. et al. "Synthesis and fungicidal activity of 3-aryl-2-(4'-aryl thiazol-2'-ylaminomethyl) quinazol-4(3H)-ones," *Indian J. Chem.* 37B: 1304-1306 (1998).
Gupta, D.P.,e t al. "Thiazolidinones, azetidinones and formazans of quinazolinones," *Indian J. Chem.* 26B: 1197-1199 (1987).
Parasharya, P.M. et al. "4 (3H)-Quinazolones. Part I: 2-Alkyl/arylaminomethyl-3-p-hydroxy/methoxyphenyl-4(3H)-quinazolones," J. Inst. Chemists (India) 64: 184-185 (1992).
Parasharya, P.M. et al. "4-(3H)-Quinazolones: 2-N-aryl/alkyl-amino-methyl/ethyl-3-p-hydroxyphenyl/p-anisyl/p-arylaminocyloxyphenyl/p-N-arylcarbamoylmethoxyphenyl -4-(3H)-quinazolones," *J. Inst. Chemists* (India) 64: 238-241 (1992).
Matthews, N. et al. "Structure-activity relationships of phenothiazines in inhibiting lymphocyte motility as determined by a novel flow cytometric assay," *Biochem. Pharmcol.* 50(7): 1053-1061 (1995).
List of Purchased Compounds 10/00.
Debnath, A.K. "Structure-Based Identification of Small Molecule Antiviral Compounds Targeted to the gp41 Core Structure of the Human Immunodeficiency Virus Type 1," *J. Med. Chem.* 42 (17): 3203-3209 (1999).
Bocskei, Z. et al.. "Two Antithrombotic Quinazolone Derivatives." *Acta Crystallogr., Sect. C: Cryst. Struct. Commun.* C51(4): 723-726 (1995).

Szabó, M. et al. "Synthesis of Potential CCK Antagonist Quinazolone Derivatives," Chemical Abstracts, vol. 124, No. 13, Abstract No. 176002v (1996).

Ager et al. "Synthesis and Central Nervous System Activity of Quinazolones Related to 2-Methyl-3-(o-tolyl)-4(3H) quinazolone (Methaqualone)," J. Med. Chem. 20(3): 379-386 (1977).

Tiwari et al. "Synthesis and CNS Activity of 2-Aryl-3(3'-, 4'-Dihydroxyphenylethyl) 6-8-substituted-4 (3H)Quinazolinones," Indian J. Pharm. Sci. pp. 40-43 (1978).

Rao et al. "Synthesis and Biological Activities of Certain Derivatives of 3-Aryl-4(3H)-quinazolinones, Part-II," J. Indian Chem. Soc. LXII: 234-237 (1985).

Registry file compounds from unspecified chemical libraries. Commercially available from ComGenex, Sep. 16, 1999.

Registry File Compounds from Published References, Maybridge Catalog, Apr. 3, 2000.

Singh et al. Chemical Abstracts, vol. 92, Abstract No. 58712 (1980).

Spirkova et al., Chemical Abstracts, vol. 132, Abstract No. 35672 (1999).

Pandey et al. Chemical Abstracts, vol. 124, Abstract No. 331723 (1996).

Parasharya et al. Chemical Abstracts, vol. 121, Abstract No. 108675 (1994).

Saari et al. Chemcial Abstracts, vol. 117, Abstract No. 191731 (1992).

Farghaly et al. Chemical Abstracts, vol. 114, Abstract No. 122242 (1991).

El-Nasser Ossman et al. Chemical Abstracts, vol. 106, Abstract No. 207516 (1987).

Rao et al. Chemical Abstracts, vol. 105, Abstract No. 97416 (1986).

Gupta et al. Chemical Abstracts, vol. 69, Abstract No. 42637 (1968).

Kumar et al. Chemical Abstracts, vol. 102, Abstract No. 142800 (1985).

Chaurasia et al. Chemical Abstracts, vol. 96, Abstract No. 6681 (1982).

Tani et al. Chemical Abstracs, vol. 93, Abstract No. 26374 (1980).

Ager et al. Chemical Abstracts, vol. 86, Abstract No. 83505 (1977).

Kozhevnikov et al. Chemical Abstracts, vol. 78, Abstract No. 16128U (1971).

Bergman et al. "Synthesis of Chrysogine, a Metabolite of Penicillium chrysogenum and some related 2-substituted 4-(3H)-Quinazolinones," Tetrahedron 46: 1295-1310 (1990).

Hart et al. "Synthesis of (−)-Alantrypinone," Tet. Lett. 40: 5429-5432 (1999).

Hart et al. "Synthesis of ent-Alantrypinone" J. Am. Chem. Soc. 123: 5892-5899 (2001).

Mayer et al. "Solid phase synthesis of quinazolinones" Tet. Lett. 38(49):8445-8448 (1997).

Prashad et al. "Reaction of benzoyleneurea and isatoic anhydride with the Vilsmeier reagent" Tet. Lett. 38(8):1313-1316 (1997).

Villalgordo et al. "Solid-phase synthesis of 3H-quinazolin-4-ones based on an aza Wittig-mediated annulation strategy" Synlett 1405-1407 (1998).

Wuckelt et al. "Efficient synthesis of quinazolin-4-ones and axially chiral 2,2'-bis-quinazolin-4-ones by reaction of anthranilic acid derived nucleophiles with oxalic acid-bis(imidoyl)chlorides." Synlett 7:1100-1102 (1999).

Wang et al. "Total synthesis of the quinazolinone alkaloids (−)-Fumiquinazoline G and (−)-Fiscalin B" J. Org. Chem. 63:2432-2433 (1998).

Padia et al. "Novel nonpeptide CCK-B antagonists: Design and development of quinazolinone derivatives as potent, selective, and orally active CCK-B antagonists" J. Med. Chem. 41:1042-1049 (1998).

Singh et al. "4-Quinazolones—II Synthesis of some imidazo [1,5-a] quinazolones" J. Indian Chem. Soc. 46(1):21-25 (1969).

Badawy et al. "Chemistry of Quinazolines: Reinvestigation of the Action of Hydrazine on Thioxo Derivatives" J. Heterocyclic Chem. 22: 1535-1536 (1985).

Yu et al. "Synthesis and x-ray crystallographic analysis of quinazolinone cholecystokinin/gastrin receptor ligands" J. Med. Chem. 35:2534-2542 (1992).

Zaher et al. "Reactions of 2-p-anisyl-3(4H), 1-benzoxazin-4-one with ammonia, primary amines, hydrazine, phenylhydrazine & Grignard reagents" Indian J. Chem. 12:1212-1215 (1974).

Kulkarni et al. "Possible antifertility agents. Part-I. Synthesis of 2-(N,N-substituted-aminomethyl)-3-(2-pyridyl)-4(3H)-oxo-3,1-quinazolines" J. Indian Chem. LXI:720-721 (1984).

Majo et al. "Dimerization of substituted 2-aminobenzoic acids under Vilsmeier conditions: A novel route to the synthesis of 4-(3H)-quinazolinones" Tet. Lett. 37(28):5015-5018 (1996).

Rathman et al. "Functionalization of 2-methyl-3-o-tolyl-4(3H)-quinazolinone and related compounds through carbanion reactions at the 2-methyl group" J. Org. Chem. 45:2169-2176 (1980).

Padia et al. "Design and synthesis of novel nonpeptide CCK-B receptor antagonists" Bioorg. Med. Chem. Lett. 7(7):805-810 (1997).

Zentmyer et al. "The so-called acylanthranils (3,1,4-benzoxazones). I. Preparation; reactions with water, ammonia, and aniline; structure" J. Organic Chemistry, 14: 967-981 (1949).

Panday, V.K. "Possible Antiparkinsonian Compounds Part XI: Synthesis of 2-aryl/alkyl-3-[β-(3'-4'-dihydroxyphenyl) ethyl]-quinazolin (3H)-4-one and 2-aryl/alkyl-3-[(7'-(phenothiazinyl)-ethyl]-quinazolin/(3H)-4-one" Acta Ciencia Indica 4(3):230-235 (1978).

Tiwari et al. Chemical Abstracts, vol. 96, Abstract No. 142790p (1982).

Fadda et al. "Reactions of a heterocyclic β-enaminoester: Synthesis of pyranopyrimidines and pyrano[3', 2', : 5,6]pyrimidino[2,3-c][1,4]benzoxazine ring system," Indian J. Chemistry 29B: 1020-1024 (1990).

Wagner "Synthesis and Biological Evaluation of Some Derivatives of Pyrido[3, 2-d]pyrimidine" Acta Poloniae Pharmaceutica—Drug Research 51(4-5): 359-363 (1994).

El-Sharief et al. "Oxidation of 3-aminoquinazolinones with lead tetraacetate. A novel synthesis of naphtho-fused azirino-pyrazolo and 1,4,5-oxadiazepino-quinazolinones" J. Chem Research (S); 205-208 (2002).

Chenard et al. "Quinazolin-4-one α-Amino-3-hydroxy-5-methyl-4-isoxazolepropionic Acid (AMPA) Receptor Antagonists: Structure-Activity Relationship of the C-2 Side Chain Tether" J. Med. Chem 44:1710-1717 (2001).

Garg et al. "Synthesis and anti-implantation activity of α-(2-aryl-3-ethyl-4-oxo (3H) quinazolinyl)-α-(substituted styryl)-cyclohexanone thiosemicarbazones" Biol. Mem.14(2):180-186 (1988).

Singh et al. "Synthesis and pharmacological screening of some 2-aryl-3-(phenyl-aryl-hydrazonyl)-quinazolin (3H) 4-ones" Indian Drugs 28(2):70-74 (1990).

Ahmad et al. "Monoamine oxidase Inhibitory Activity of 4 (3H)-Quinazolinones of Dopamine" Indian J. of Pharm. Sci. 126-127 (1979).

Tiwari et al. "Possible Antifertility Compounds Part III: Synthesis of 2-Hippuryl-3-Aryl-Quinazolinones" J. Chem. Soc. Pak. 3(4):215-217 (1981).

Pandey, V.K. "Antiparkinsonism and CNS Activities of 2-aryl alkyl-3-{β-(3'-4'-dihydroxyphenyl) Ethyl}-quinazolin (3H) 4-ones" Biol. Mem. 11(2):213-215 (1985).

Szabó et al. "Uj kinazolonszarmazekok szintezise es ciklizalasa [1,4]oxazepino- es [1,4]diazepino [3,4-b]kinazolonkka" Magyar Kemiai Folyoirat 102(8):343-355 (1996) translated abstract.

Reddy et al. "A New Synthesis of 2-aryl-2H-Pyrazino[2,1-β]Quinazolin-3,6(1H,4H)-Diones" Synthetic Communications 21 (2):173-181 (1991).

Szabó et al. "Potencialis CCK-antagonista kinazolon-szarmazekok szintezse" Acta Pharm. Hungarica 65:133-136 (1995) translated abstract.

Pandy et al. "Quinazolyl-thiazoles as CNS acting agents" Acta Pharm. 46:51-59 (1996).

Reddy et al. "4-Heteryl-β-lactams: A facile synthesis of 1-aryl-4-[isopropylideneamino/methyl-4(3H)-oxoquinazolin-2-yl] azetidin-2-ones" Indian J. of Chem. 38B:40-44 (1999).

Reddy et al. "Bisazaheterocycles: Part VII—Synthesis of novel bisquinazolinonyl β-lactams" Ind. J. of Chem. 41B:1946-1949 (2002).

Gyimesi-Forrás et al. "Az AGP-alapu folyadek-kromatografias allofazis alkalmazasa kinazolon szarmazekok enantiomerjeinek elvalasztasaban" *Acta Pharma. Hungarica* 73:5-12 (2003) translated abstract.
Reddy et al. "Synthesis of 2-quinazolinonyl imidazolidinones" *Ind. J. of Chem*. 42B:393-396 (2003).
Gyimesi-Forrás et al. "Optical Resolution of a Series of Potential Cholecystokinin Antagonist 4(3H)-Quinazolone Derivatives by Chiral Liquid Chromatography on $\alpha_1$-Acid Glycoprotein Stationary Phase" *J. of Chromat. Sci*. 38:430-434 (2000).
Jiang et al. "A Salt Bridge between on N-terminal Coiled Coil of gp41 and an Antiviral Agent Targeted to the gp41 Core Is Important for Anti-HIV-1 Activity" *Biochem. and Biophys. Res. Communications* 270:153-157 (2000).
Hughes et al. "Quinazoline Antifolate Thymidylate Synthase Inhibitors: Alkyl, Substituted Alkyl, and Aryl Substituents in the C2 Position" *J. Med. Chem*. 33:3060-3067 (1990).
Hassanein et al. "Synthesis of 2-substituted-10H-[1,2,4] triazino [6,1-b] quinazoline-10-ones and 8,13,14,16 tetrahydronaphtho [2',3',:3,4] [1,2,5] triazepino [7,1-b] quinazoline-8,13,16-triones with biological interest" *Al-Azhar Bull. Sci*. 8(2):417-434 (1997).
Szabó et al. "Nitrogen Bridgehead Compounds: Part 88 [1], Synthesis of 3H,7H-[1,4]Diazepino[3,4-b]quinazoline-3,7-diones" *J. Heterocyclic Chem*. 34(21):21-25 (1997).
Kokosi et al. "Nitrogen Bridgehead Compounds Part 90. An Efficient Versatile Synthesis of 1-Methyl-2-substituted 1,2,3,4-Tetrahydro-6H-Pyrazino[2,1-b]Quinazoline-3,6-Diones" *Heterocycles* 48(9):1851-1866 (1998).
El-Maghraby et al. "Synthesis of Glycylaminothiazoles" *Ind. J. Chem*. 12:1058-1059 (1974).
Hassan et al. "Synthesis and antimicrobial activity of some new N-aminoacyl derivatives of 2-amino-4-phenylthiazole" *Acta Pharm*. 47:159-166 (1997).
West, "Solid State Chemistry and it's Applications," Wiley, New York, 1988, pp. 358 & 365.
Office Action mailed May 7, 2001, for U.S. Appl. No. 09/699,047, filed Oct. 24, 2000.
Office Action mailed Apr. 24, 2002, for U.S. Appl. No. 09/699,047, filed Oct. 24, 2000.
Office Action mailed Feb. 6, 2002, for U.S. Appl. No. 09/724,644, filed Nov. 28, 2000.
Office Action mailed Oct. 21, 2002, for U.S. Appl. No. 09/724,644, filed Nov. 28, 2000.
Office Action mailed Feb. 6, 2002, for U.S. Appl. No. 09/724,712, filed Nov.28, 2000.
Office Action mailed Apr. 9, 2002, for U.S. Appl. No. 09/724,713, filed Nov. 28, 2000.
Office Action mailed Oct. 21, 2002, for U.S. Appl. No. 09/724,713, filed Nov. 28, 2000.
Office Action mailed Mar. 22, 2002, for U.S. Appl. No. 09/724,897, filed Nov. 28, 2000.
Office Action mailed Dec. 17, 2002, for U.S. Appl. No. 09/724,897, filed Nov. 28, 2000.
Office Action mailed Jul. 11, 2003, for U.S. Appl. No. 09/724,897, filed Nov. 28, 2000.
Office Action mailed May 12, 2004, for U.S. Appl. No. 09/724,897, filed Nov. 28, 2000.
Office Action mailed Jul. 26, 2002, for U.S. Appl. No. 09/724,941, filed Nov. 28, 2000.
Office Action mailed Jan. 13, 2003, for U.S. Appl. No. 09/724,941, filed Nov. 28, 2000.
Office Action mailed Jan. 7, 2004, for U.S. Appl. No. 09/724,941, filed Nov. 28, 2000.
Office Action mailed Jul. 3, 2002, for U.S. Appl. No. 09/724,778, filed Nov. 28, 2000.
Office Action mailed Dec. 27, 2002, for U.S. Appl. No. 09/724,778, filed Nov. 28, 2000.
Office Action mailed Aug. 8, 2003, for U.S. Appl. No. 09/724,778, filed Nov. 28, 2000.
Office Action mailed Dec. 29, 2003, for U.S. Appl. No. 09/724,778, filed Nov. 28, 2000.
Office Action mailed Mar. 30, 2004, for U.S. Appl. No. 09/724,778, filed Nov. 28, 2000.
Office Action mailed Jun. 25, 2004, for U.S. Appl. No. 09/724,778, filed Nov. 28, 2000.
International Search Report mailed Feb. 22, 2001, for PCT Application No. PCT/US00/29585, filed Oct. 26, 2000.
Written Opinion mailed Sep. 21, 2001, for PCT Application No. PCT/US00/29585, filed Oct. 26, 2000.
International Preliminary Examination Report mailed Jan. 17, 2002, for PCT Application No. PCT/US00/29585, filed Oct. 26, 2000.
Office Action mailed Aug. 8, 2003, for U.S. Appl. No. 10/300,967, filed Nov. 20, 2002.
International Search Report mailed Feb. 7, 2003, for PCT Application No. PCT/US02/37410, filed Nov. 20, 2002.
Written Opinion mailed Sep. 9, 2003, for PCT Application No. PCT/US02/37410, filed Nov. 20, 2002.
International Preliminary Examination Report mailed Aug. 11, 2004, for PCT Application No. PCT/US02/37410, filed Nov. 20, 2002.
International Search Report mailed Oct. 31, 2001, for PCT Application No. PCT/US01/13901, filed Apr. 27, 2001.
International Search Report mailed Oct. 17, 2003, for PCT Application No. PCT/US03/18778, filed Jun. 12, 2003.
Office Action mailed Oct. 18, 2004, for U.S. Appl. No. 10/462,002, filed Jun. 12, 2003.
Written Opinion mailed Mar. 2, 2004, for PCT Application No. PCT/US03/18778, filed Jun. 12, 2003.
International Preliminary Examination Report mailed Sep. 8, 2004, for PCT Application No. PCT/US03/18778, filed Jun. 12, 2003.
International Search Report and Written Opinion mailed Dec. 6, 2004, for PCT Application No. PCT/US04/01279, filed Jan. 20, 2004.
International Search Report mailed Aug. 29, 2003, for PCT Application No. PCT/US03/14787, filed May 9, 2003.
Written Opinion mailed Jun. 10, 2004, for PCT Application No. PCT/US03/14787, filed May 9, 2003.
International Preliminary Examination Report mailed Nov. 16, 2004, for PCT Application No. PCT/US03/14787, filed May 9, 2003.
International Search Report mailed Jul. 16, 2004, for PCT Application No. PCT/US03/13627, filed May 2, 2003.
Office Action mailed Nov. 2, 2004, for U.S. Appl. No. 10/366,828, filed Feb. 14, 2003.
International Search Report mailed Aug. 12, 2003, for PCT Application No. PCT/US03/04713, filed Feb. 14, 2003.
Written Opinion mailed Jun. 24, 2004, for PCT Application No. PCT/US03/04713, filed Feb. 14, 2003.
International Preliminary Examination Report mailed Dec. 8, 2004, for PCT Application No. PCT/US03/04713, filed Feb. 14, 2003.
International Search Report mailed Jul. 9, 2004, for PCT Application No. PCT/US03/23319, filed Jul. 23, 2003.
International Preliminary Examination Report mailed Sep. 30, 2004, for PCT Application No. PCT/US03/23319, filed Jul. 23, 2003.
International Search Report mailed May 20, 2004, for PCT Application No. PCT/US03/26093, filed Aug. 20, 2003.
International Preliminary Examination Report mailed Aug. 5, 2004, for PCT Application No. PCT/US03/26093, filed Aug. 20, 2003.
Office Action mailed Jan. 4, 2005, for U.S. Appl. No. 10/444,283, filed May 22, 2003.
International Search Report mailed Dec. 18, 2003, for PCT Application No. PCT/US03/16500, filed May 22, 2003.
International Preliminary Examination Report mailed Jun. 23, 2004, for PCT Application No. PCT/US03/16500, filed May 22, 2003.
Bergnes et al., "Compounds, Compositions, and Methods," U.S. Appl. No. 10/980,627, filed Nov. 2, 2004.
Bergnes et al., "Compounds, Compositions, and Methods," U.S. Appl. No. 10/982,195, filed Nov. 5, 2004.
Bergnes, "Compounds, Compositions, and Methods," U.S. Appl. No. 11/005,629, filed Dec. 7, 2004.
Written Opinion mailed Sep. 24, 2004, for PCT Application No. PCT/US02/41309, filed Dec. 20, 2002.
International Search Report mailed Oct. 12, 2004, for PCT Application No. PCT/US03/30788, filed Sep. 30, 2003.
Office Action mailed Feb. 7, 2005, for U.S. Appl. No. 10/435,069, filed May 8, 2005.
International Preliminary Examination Report mailed Jan. 28, 2005, for PCT Application No. PCT/US03/30788, filed Sep. 30, 2003.

Office Action mailed Apr. 27, 2005, for U.S. Appl. No. 10/429,195, filed May 2, 2003.
International Preliminary Examination Report mailed May 9, 2005, for PCT Application No. PCT/US03/13627, filed May 2, 2003.
International Search Report and Written Opinion mailed Apr. 28, 2005, for PCT Application No. PCT/US04/36253, filed Nov. 2, 2004.
International Search Report and Written Opinion mailed Jun. 14, 2005, for PCT Application No. PCT/US04/36853, filed Nov. 5, 2004.
Sauter et al., CAPLUS Abstract No. 87:84931 (1977).
Uchida et al., CAPLUS Abstract No. 81:152142 (1974).
Yamada et al., CAPLUS Abstract No. 134:252363 (2001).
Matsuoka et al., CAPLUS Abstract No. 133:150920 (2000).
Nugent et al., CAPLUS Abstract No. 123:143921 (1995).
De Melo et al., CAPLUS Abstract No. 117:143023 (1992).
Irikura et al., CAPLUS Abstract No. 105:42834 (1986).
Kyorin Pharmaceutical Co., Ltd., CAPLUS Abstract No. 103:87901 (1985).
Shuto et al., CAPLUS Abstract No. 90:72134 (1979).
Katagiri et al., CAPLUS Abstract No. 100:51536 (1984).
Hegrand et al., CAPLUS Abstract No. 80:95873 (1974).
Witkop et al., CAPLUS Abstract No. 75:77191 (1971).
Office Action mailed Jun. 24, 2005, for U.S. Appl. No. 10/773,602, filed Feb. 6, 2004.
Office Action mailed Jul. 6, 2005, for U.S. Appl. No. 10/982,195, filed Nov. 5, 2004.
Gavezzotti "Are Crystal Structures Predictable" *Acc. Chem. Res.* 27:309-314 (1994).
Wolff (ed.) *Burger's Medicinal Chemistry and Drug Discovery*, 5$^{th}$ Edition vol. 1: *Principles and Practice*, John Wiley & Sons, New York, pp. 975-977 (1995).
Banker et al. (eds.) *Modern Pharmaceuticals Third Edition, Revised and Expanded*, Marcel Dekker, Inc., New York, pp. 451 & 596 (1996).
Coleman et al. "Inhibitors of the mitotic kinesin spindle protein" *Expert Opin. Ther. Patents* 14(12): 1659-1667 (2004).
Li et al. "Discovery and development of antimitotic agents that inhibit tubulin polymerisation for the treatment of cancer" *Expert Opin. Ther. Patents* 12(11): 1663-1702 (2002).
Malik et al., "Compositions, Devices and Methods for Treating Cardiovascular Disease," U.S. Appl. No. 11/147,406, filed Jun. 7, 2005.
Communication and Supplementary European Search Report from the European Patent Office dated Aug. 1, 2006, for Application No. EP 03753011.0-2107, PCT/US03/14787, 3 pages.
Notice of Allowance mailed Aug. 12, 2005, for U.S. Appl. No. 10/435,069, filed May 8, 2005.

COMPOUNDS, COMPOSITIONS, AND METHODS

CROSS-REFERENCE TO RELATED PATENT APPLICATIONS

This application is a continuation of U.S. patent application Ser. No. 10/435,069, filed May 8, 2003, now U.S. Pat. No. 7,214,800 which claims benefit of U.S. Provisional Patent Application No. 60/379,531, filed May 9, 2002. Each of these applications is incorporated herein by reference for all purposes.

FIELD OF THE INVENTION

This invention relates to compounds which are inhibitors of the mitotic kinesin KSP and are useful in the treatment of cellular proliferative diseases, for example cancer, hyperplasias, restenosis, cardiac hypertrophy, immune disorders, fungal disorders, and inflammation.

BACKGROUND OF THE INVENTION

Among the therapeutic agents used to treat cancer are the taxanes and vinca alkaloids, which act on microtubules. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures, such as in nerve processes. Mitotic kinesins play essential roles during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins which have been identified is Kinesin Spindle Protein (KSP). KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described (Blangy, et al., Cell, 83:1159-69 (1995); Whitehead, et al., Arthritis Rheum., 39:1635-42 (1996); Galgio et al., J. Cell Biol., 135:339-414 (1996); Blangy, et al., J. Biol. Chem., 272:19418-24 (1997); Blangy, et al., Cell Motil Cytoskeleton, 40:174-82 (1998); Whitehead and Rattner, J. Cell Sci., 111:2551-61 (1998); Kaiser, et al., JBC 274:18925-31 (1999); GenBank accession numbers: X85137, NM004523 and U37426), and a fragment of the KSP gene (TRIP5) has been described (Lee, et al., Mol Endocrinol., 9:243-54 (1995); GenBank accession number L40372). *Xenopus* KSP homologs (Eg5), as well as *Drosophila* KLP61 F/KRP1 30 have been reported.

Mitotic kinesins, including KSP, are attractive targets for the discovery and development of novel antimitotic chemotherapeutics. Accordingly, it is an object of the present invention to provide compounds, compositions and methods useful in the inhibition of KSP.

SUMMARY OF THE INVENTION

In accordance with the objects outlined above, the present invention provides compounds that can be used to treat cellular proliferative diseases. The compounds are KSP inhibitors, particularly human KSP inhibitors. The present invention also provides compositions comprising such compounds, and methods utilizing such compounds or compositions, which can be used to treat cellular proliferative diseases In one aspect, the invention relates to methods for treating cellular proliferative diseases, and for treating disorders by inhibiting the activity of KSP. The methods employ compounds represented by Formula Ia or Ib:

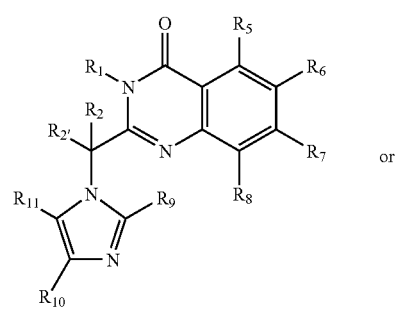

Formula Ia or

-continued

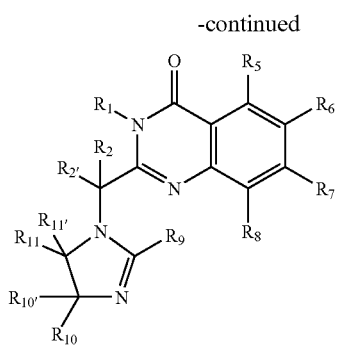

Formula Ib wherein:

$R_1$ is chosen from hydrogen, optionally substituted alkyl-, optionally substituted aryl-, optionally substituted aryl-$C_1$-$C_4$-alkyl-, optionally substituted heteroaryl-, and optionally substituted heteroaryl-$C_1$-$C_4$-alkyl-;

$R_2$ and $R_2'$ are independently chosen from hydrogen, optionally substituted alkyl-, optionally substituted aryl-, optionally substituted aryl-$C_1$-$C_4$-alkyl-, optionally substituted heteroaryl-, and optionally substituted heteroaryl-$C_1$-$C_4$-alkyl-; or $R_2$ and $R_2'$ taken together form an optionally substituted 3- to 7-membered ring;

$R_5$, $R_6$, $R_7$ and $R_8$ are independently chosen from hydrogen, optionally substituted alkyl-, optionally substituted alkoxy, halogen, hydroxyl-, nitro, cyano, dialkylamino, alkyl-sulfonyl-, alkylsulfonamido, alkylthio, carboxyalkyl-, carboxamido, aminocarbonyl-, optionally substituted aryl-, optionally substituted aryloxy, optionally substituted heteroaryl-, and optionally substituted heteroaryloxy;

$R_9$ is chosen from hydrogen, optionally substituted alkyl-, optionally substituted aryl-, optionally substituted aralkyl-, and optionally substituted heteroaryl-; and $R_{10}$, $R_{10'}$, $R_{11}$, and $R_{11'}$ are independently hydrogen, optionally substituted alkyl-, optionally substituted aryl-, or optionally substituted aralkyl-, (Formula Ia or Ib including single stereoisomers and mixtures of stereoisomers);

pharmaceutically acceptable salts of a compound of Formula Ia or Ib;

pharmaceutically acceptable solvates of a compound of Formula Ia or Ib; and pharmaceutically acceptable solvates of a pharmaceutically acceptable salt of a compound of Formula Ia or Ib.

In one aspect, the invention relates to methods for treating cellular proliferative diseases and other disorders that can be treated by inhibiting KSP by the administration of a therapeutically effective amount of a compound of Formula Ia or Ib; a pharmaceutically acceptable salt of a compound of Formula Ia or Ib; pharmaceutically acceptable solvate of a compound of Formula Ia or Ib; or a pharmaceutically acceptable solvate of a pharmaceutically acceptable salt of a compound of Formula Ia or Ib. Such diseases and disorders include cancer, hyperplasia, restenosis, cardiac hypertrophy, immune disorders, fungal disorders and inflammation.

In another aspect, the invention relates to compounds useful in inhibiting KSP kinesin. The compounds have the structures shown above in Formula Ia or Ib; a pharmaceutically acceptable salt of a compound of Formula Ia or Ib; a pharmaceutically acceptable solvate of a compound of Formula Ia or Ib; or a pharmaceutically acceptable solvate of a pharmaceutically acceptable salt of a compound of Formula Ia or Ib. The invention also relates to pharmaceutical compositions comprising: a therapeutically effective amount of a compound of Formula Ia or Ib; a pharmaceutically acceptable salt of a compound of Formula Ia or Ib; a pharmaceutically acceptable solvate of a compound of Formula Ia or Ib; or a pharmaceutically acceptable solvate of a pharmaceutically acceptable salt of a compound of Formula Ia or Ib; and one or more pharmaceutical excipients. In another aspect, the composition further comprises a chemotherapeutic agent other than a compound of the present invention.

In an additional aspect, the present invention provides methods of screening for compounds that will bind to a KSP kinesin, for example compounds that will displace or compete with the binding of a compound of the invention. The methods comprise combining a labeled compound of the invention, a KSP kinesin, and at least one candidate agent and determining the binding of the candidate agent to the KSP kinesin.

In a further aspect, the invention provides methods of screening for modulators of KSP kinesin activity. The methods comprise combining a compound of the invention, a KSP kinesin, and at least one candidate agent and determining the effect of the candidate agent on the KSP kinesin activity.

DETAILED DESCRIPTION OF THE INVENTION

Definitions

As used in the present specification, the following words and phrases are generally intended to have the meanings as set forth below, except to the extent that the context in which they are used indicates otherwise. The following abbreviations and terms have the indicated meanings throughout:

Ac=acetyl
Boc=t-butyloxy carbonyl
Bu=butyl
c-=cyclo
CBZ=carbobenzoxy=benzyloxycarbonyl
DCM=dichloromethane=methylene chloride=$CH_2Cl_2$
DIEA=N,N-diisopropylethylamine
DMF=N,N-dimethylformamide
DMSO=dimethyl sulfoxide
Et=ethyl
Fmoc=9-fluorenylmethoxycarbonyl
GC=gas chromatography
HOAc=acetic acid
Me=methyl
mesyl=methanesulfonyl
PEG=polyethylene glycol
Ph=phenyl
PhOH=phenol
Pht=phthalyl
Py=pyridine
rt or RT=room temperature
sat'd=saturated
s-=secondary
t-=tertiary
TFA=trifluoroacetic acid
THF=tetrahydrofuran
tosyl=p-toluenesulfonyl Alkyl is intended to include linear, branched, or cyclic aliphatic hydrocarbon structures and combinations thereof, which structures may be saturated or unsaturated. Lower-ally refers to alkyl groups of from 1 to 5 carbon atoms, preferably from 1 to 4 carbon atoms. Examples of lower-alkyl groups include methyl-, ethyl-, propyl-, isopropyl-, butyl-, s- and t-butyl- and the like. Preferred alkyl groups are those of $C_{20}$ or below. More preferred alkyl groups are those of $C_{13}$ or below.

Cycloalkyl is a subset of alkyl and includes cyclic aliphatic hydrocarbon groups of from 3 to 13 carbon atoms. Examples of cycloalkyl groups include c-propyl-, c-butyl-, c-pentyl-, norbornyl-, adamantyl- and the like. Cycloalkyl-alkyl- is another subset of alkyl and refers to cycloalkyl attached to the parent structure through a non-cyclic alkyl-. Examples of cycloalkyl-alkyl- include cyclohexylmethyl-, cyclopropylmethyl-, cyclohexylpropyl-, and the like. In this application, alkyl includes alkanyl-, alkenyl- and alkynyl-residues; it is intended to include vinyl-, allyl-, isoprenyl- and the like. When an alkyl residue having a specific number of carbons is named, all geometric isomers having that number of carbons are intended to be encompassed; thus, for example, "butyl" is meant to include n-butyl-, sec-butyl-, isobutyl- and t-butyl-; "propyl" includes n-propyl-, isopropyl-, and c-propyl-.

Alkylene-, alkenylene-, and alkynylene- are other subsets of alkyl-, including the same residues as alkyl-, but having two points of attachment within a chemical structure. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). Likewise, examples of alkenylene include ethenylene (—CH=CH—), propenylene (—CH=CH—$CH_2$—), and cyclohexylpropenylene (—CH=CHCH($C_6H_{13}$)—). Examples of alkynylene include ethynylene (—C≡C—) and propynylene (—CH≡CH—$CH_2$—).

Cycloalkenyl is a subset of alkyl and includes unsaturated cyclic hydrocarbon groups of from 3 to 13 carbon atoms. Examples of cycloalkenyl groups include c-hexenyl-, c-pentenyl- and the like.

Alkoxy or alkoxyl refers to an alkyl group, preferably including from 1 to 8 carbon atoms, of a straight, branched, or cyclic configuration, or a combination thereof, attached to the parent structure through an oxygen (i.e., the group alkyl-O—). Examples include methoxy-, ethoxy-, propoxy-, isopropoxy-, cyclopropyloxy-, cyclohexyloxy- and the like. Lower-alkoxy refers to alkoxy groups containing one to four carbons.

Acyl refers to groups of from 1 to 8 carbon atoms of a straight, branched, or cyclic configuration or a combination thereof, attached to the parent structure through a carbonyl functionality. Such groups may be saturated or unsaturated, and aliphatic or aromatic. One or more carbons in the acyl residue may be replaced by oxygen, nitrogen (e.g., carboxamido), or sulfur as long as the point of attachment to the parent remains at the carbonyl. Examples include acetyl-, benzoyl-, propionyl-, isobutyryl-, oxalyl-, t-butoxycarbonyl-, benzyloxycarbonyl-, morpholinylcarbonyl-, and the like. Lower-acyl refers to acyl groups containing one to four carbons.

Amino refers to the group —$NH_2$. The term "substituted amino" refers to the group —NHR or —NRR where each R is independently selected from the group: optionally substituted alkyl-, optionally substituted alkoxy, optionally substituted aminocarbonyl-, optionally substituted aryl-, optionally substituted heteroaryl-, optionally substituted heterocyclyl-, acyl-, alkoxycarbonyl-, sulfanyl-, sulfinyl- and sulfonyl-, e.g., diethylamino, methylsulfonylamino, furanyl-oxy-sulfonamino.

Aminocarbonyl- refers to the group —$NR^cCOR^b$, —$NR^cCO_2R^a$, or —$NR^cCONR^bR^c$, where $R^a$ is optionally substituted $C_1$-$C_6$ alkyl-, aryl-, heteroaryl-, aryl-$C_1$-$C_4$ alkyl-, or heteroaryl-$C_1$-$C_4$ alkyl- group;

$R^b$ is H or optionally substituted $C_1$-$C_6$ alkyl-, aryl-, heteroaryl-, aryl-$C_1$-$C_4$ alkyl-, or heteroaryl-$C_1$-$C_4$ alkyl- group; and $R^c$ is hydrogen or $C_1$-$C_4$ alkyl-; and where each optionally substituted $R^b$ group is independently unsubstituted or substituted with one or more substituents independently selected from $C_1$-$C_4$ alkyl-, aryl-, heteroaryl-, aryl-$C_1$-$C_4$ alkyl-, heteroaryl-$C_1$-$C_4$ alkyl-, $C_1$-$C_4$ haloalkyl-, —O$C_1$-$C_4$ alkyl-, —O$C_1$-$C_4$ alkylphenyl-, —$C_1$-$C_4$ alkyl-OH, —O$C_1$-$C_4$ haloalkyl-, halogen, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl-, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl-, —C(O)$C_1$-$C_4$ phenyl-, —C(O)$C_1$-$C_4$ haloalkyl-, —OC(O)$C_1$-$C_4$ alkyl-, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

Antimitotic refers to a drug for inhibiting or preventing mitosis, for example, by causing metaphase arrest. Some antitumour drugs block proliferation and are considered antimitotics.

Aryl and heteroaryl mean a 5- or 6-membered aromatic or heteroaromatic ring containing 0 or 1-4 heteroatoms, respectively, selected from O, N, or S; a bicyclic 9- or 10-membered aromatic or heteroaromatic ring system containing 0 or 1-4 (or more) heteroatoms, respectively, selected from O, N, or S; or a tricyclic 12- to 14-membered aromatic or heteroaromatic ring system containing 0 or 1-4 (or more) heteroatoms, respectively, selected from O, N, or S. The aromatic 6- to 14-membered carbocyclic rings include, e.g., phenyl-, naphthyl-, indanyl-, tetralinyl-, and fluorenyl- and the 5- to 10-membered aromatic heterocyclic rings include, e.g., imidazolyl-, pyridinyl-, indolyl-, thienyl-, benzopyranonyl-, thiazolyl-, furanyl-, benzimidazolyl-, quinolinyl-, isoquinolinyl-, quinoxalinyl-, pyrimidinyl-, pyrazinyl-, tetrazolyl- and pyrazolyl-.

Aralkyl- refers to a residue in which an aryl moiety is attached to the parent structure via an alkyl residue. Examples include benzyl-, phenethyl-, phenylvinyl-, phenylallyl- and the like. Heteroaralkyl- refers to a residue in which a heteroaryl moiety is attached to the parent structure via an alkyl residue. Examples include furanylmethyl-, pyridinylmethyl-, pyrimidinylethyl- and the like.

Aralkoxy- refers to the group —O-aralkyl. Similarly, heteroaralkoxy- refers to the group —O-heteroaralkyl-; aryloxy- refers to the group —O-aryl-; acyloxy- refers to the group —O-acyl-; heteroaryloxy- refers to the group —O-heteroaryl-; and heterocyclyloxy- refers to the group —O-heterocyclyl (i.e., aralkyl-, heteroaralkyl-, aryl-, acyl-, heterocyclyl-, or heteroaryl is attached to the parent structure through an oxygen).

Carboxyalkyl- refers to the group -alkyl-COOH.

Carboxamido refers to the group —$CONR^bR^c$, where $R^b$ is H or optionally substituted $C_1$-$C_6$, alkyl-, aryl-, heteroaryl-, aryl-$C_1$-$C_4$ alkyl-, or heteroaryl-$C_1$-$C_4$ alkyl- group; and $R^c$ is hydrogen or $C_1$-$C_4$ alkyl-; and where each optionally substituted $R^b$ group is independently unsubstituted or substituted with one or more substituents independently selected from $C_1$-$C_4$ alkyl-, aryl-, heteroaryl-, aryl-$C_1$-$C_4$ alkyl-, heteroaryl-$C_1$-$C_4$ alkyl-, $C_1$-$C_4$ haloalkyl-, —O$C_1$-$C_4$ alkyl-, —O$C_1$-$C_4$ alkylphenyl-, —$C_1$-$C_4$ alkyl-OH, —O$C_1$-$C_4$ haloalkyl-, halogen, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2$H, —C(O)O$C_1$-$C_4$ alkyl-, —CON($C_1$-$C_4$ alkyl)($C_1$-$C_4$ alkyl), —CONH($C_1$-$C_4$ alkyl), —CON$H_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl-, —C(O)$C_1$-$C_4$ haloalkyl-, —OC(O)$C_1$-$C_4$ alkyl-, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —NHSO$_2$($C_1$-$C_4$ alkyl), —NHSO$_2$(phenyl), and —NHSO$_2$($C_1$-$C_4$ haloalkyl). Carboxamido is meant to include carbamoyl-; lower-alkyl carbamoyl-; benzylcarbamoyl-; phenylcarbamoyl-; methoxymethyl-carbamoyl-; and the like.

Halogen or halo refers to fluorine, chlorine, bromine or iodine. Fluorine, chlorine and bromine are preferred. Dihaloaryl-, dihaloalkyl-, trihaloaryl- etc. refer to aryl and alkyl substituted with the designated plurality of halogens (here, 2, 2 and 3, respectively), but not necessarily a plurality of the same halogen; thus 4-chloro-3-fluorophenyl- is within the scope of dihaloaryl-.

Heterocyclyl means a cycloalkyl or aryl residue in which one to four of the carbons is replaced by a heteroatom such as oxygen, nitrogen or sulfur. Examples of heterocycles that fall within the scope of the invention include azetidinyl-, imidazolinyl-, pyrrolidinyl-, pyrazolyl-, pyrrolyl-, indolyl-, quinolinyl-, isoquinolinyl-, tetrahydroisoquinolinyl-, benzofuranyl-, benzodioxanyl-, benzodioxyl- (commonly referred to as methylenedioxyphenyl-, when occurring as a substituent), tetrazolyl-, morpholinyl-, thiazolyl-, pyridinyl-, pyridazinyl-, piperidinyl-, pyrimidinyl-, thienyl-, furanyl-, oxazolyl-, oxazolinyl-, isoxazolyl-, dioxanyl-, tetrahydrofuranyl- and the like. "N-heterocyclyl" refers to a nitrogen-containing heterocycle. The term heterocyclyl encompasses heteroaryl-, which is a subset of heterocyclyl-. Examples of N-heterocyclyl residues include azetidinyl-, 4-morpholinyl-, 4-thiomorpholinyl-, 1-piperidinyl-, 1-pyrrolidinyl-, 3-thiazolidinyl-, piperazinyl- and 4-(3,4-dihydrobenzoxazinyl). Examples of substituted heterocyclyl include 4-methyl-1-piperazinyl- and 4-benzyl-1-piperidinyl-.

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

Optional or optionally means that the subsequently described event or circumstance may or may not occur, and that the description includes instances where said event or circumstances occurs and instances in which it does not. For example, "optionally substituted alkyl" includes "alkyl" and "substituted alkyl" as defined herein. It will be understood by those skilled in the art with respect to any group containing one or more substituents that such groups are not intended to introduce any substitution or substitution patterns that are sterically impractical and/or synthetically non-feasible and/or inherently unstable.

Substituted alkoxy refers to alkoxy wherein the alkyl constituent is substituted (i.e., —O-(substituted alkyl)). One suitable substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_x$CH$_3$, where x is an integer of about 2-20, preferably about 2-10, and more preferably about 2-5.

Another suitable substituted alkoxy group is hydroxyalkoxy or —OCH$_2$(CH$_2$)$_y$OH, where y is an integer of about 1-10, preferably about 1-4.

Substituted-alkyl-, aryl-, and heteroaryl- refer respectively to alkyl-, aryl-, and heteroaryl wherein one or more (up to about 5, preferably up to about 3) hydrogen atoms are replaced by a substituent independently selected from the group: —$R^a$, —$OR^b$, —O($C_1$-$C_2$ alkyl)O— (as an aryl substituent), —$SR^b$, —$NR^bR^c$, halogen, cyano, nitro, —$COR^b$, —$CO_2R^b$, —$CONR^bR^c$, $OCOR^b$, —$OCO_2R^a$, —$OCONR^b$ $R^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is an optionally substituted $C_1$-$C_6$ alkyl-, aryl-, heteroaryl-, aryl-$C_1$-$C_4$ alkyl-, or heteroaryl-$C_1$-$C_4$ alkyl- group, $R^b$ is H or optionally substituted $C_1$-$C_6$ alkyl-, aryl-, heteroaryl-, aryl-$C_1$-$C_4$ alkyl-, or heteroaryl-$C_1$-$C_4$ alkyl- group;

$R^c$ is hydrogen or $C_1$-$C_4$ alkyl-;

where each optionally substituted $R^a$ group and $R^b$ group is independently unsubstituted or substituted with one or more substituents independently selected from $C_1$-$C_4$ alkyl-, aryl-, heteroaryl-, aryl-$C_1$-$C_4$ alkyl-, heteroaryl-$C_1$-$C_4$ alkyl-, C—$C_4$ haloalkyl-, —O$C_1$-$C_4$ alkyl-, —O$C_1$-$C_4$ alkylphenyl-, —$C_1$-$C_4$ alkyl-OH, —O$C_1$-$C_4$ haloalkyl-, halogen, —OH, —NH$_2$, —$C_1$-$C_4$ alkyl-NH$_2$, —N($C_1$-$C_4$ alkyl)($C_1$-$C_4$ alkyl), —NH ($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —CO$_2$H, —C(O)O$C_1$-$C_4$ alkyl-, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl-, —C(O)$C_1$-$C_4$ haloalkyl-, —OC(O)$C_1$-$C_4$ alkyl-, —SO$_2$($C_1$-$C_4$ alkyl). —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

Sulfanyl refers to the groups: —S-(optionally substituted alkyl), —S-(optionally substituted aryl), —S-(optionally substituted heteroaryl), and —S-(optionally substituted heterocyclyl).

Sulfinyl refers to the groups: —S(O)—H, —S(O)-(optionally substituted alkyl), —S(O)-optionally substituted aryl), —S(O)-(optionally substituted heteroaryl), —S(O)-(optionally substituted heterocyclyl); and —S(O)-(optionally substituted amino).

Sulfonyl refers to the groups: —S(O$_2$)—H, —S(O$_2$)-(optionally substituted alkyl), —S(O$_2$)-optionally substituted aryl), —S(O$_2$)-(optionally substituted heteroaryl), —S(O$_2$)-(optionally substituted heterocyclyl), —S(O$_2$)-(optionally substituted alkoxy), —S(O$_2$)-optionally substituted aryloxy), —S(O$_2$)-(optionally substituted heteroaryloxy), —S(O$_2$)-(optionally substituted heterocyclyloxy); and —S(O$_2$)-(optionally substituted amino).

Pharmaceutically acceptable salts refers to those salts that retain the biological effectiveness of the free compound and that are not biologically undesirable or unsuitable for pharmaceutical use, formed with a suitable acid or base, and includes pharmaceutically acceptable acid addition salts and base addition salts. Pharmaceutically acceptable acid addition salts include those derived from inorganic acids such as hydrochloric acid, hydrobromic acid, sulfuric acid, nitric acid, phosphoric acid and the like, and those derived from organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutically acceptable base addition salts include those derived from inorganic bases such as sodium, potassium, lithium, ammonium, calcium, magnesium, iron, zinc, copper, manganese, aluminum salts and the like. Particular embodiments are the ammonium, potassium, sodium, calcium, and magnesium salts. Base addition salts also include those derived from pharmaceutically acceptable organic non-toxic bases, including salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

Protecting group has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999), which is incorporated herein by reference in its entirety. For example, a hydroxy protected form is where at least one of the hydroxyl groups present in a compound is protected with a hydroxy protecting group. Likewise, amines and other reactive groups may similarly be protected.

Solvate refers to the compound formed by the interaction of a solvent and a compound of Formula Ia or Ib or salt thereof. Suitable solvates of the compounds of the Formula Ia or Ib or a salt thereof are pharmaceutically acceptable solvates including hydrates.

Many of the compounds described herein contain one or more asymmetric centers (e.g. the carbon to which $R_2$ and $R_{2'}$ are attached where $R_2$ differs from $R_{2'}$) and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms and rotational isomers are also intended to be included.

When desired, the R- and S-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

Compounds of the Present Invention

The present invention is directed to a class of novel compounds, that can be described as quinazolinone derivatives, that are inhibitors of one or more mitotic kinesins. By inhibiting mitotic kinesins, but not other kinesins (e.g., transport kinesins), specific inhibition of cellular proliferation is accomplished. While not intending to be bound by any theory, the present invention capitalizes on the finding that perturbation of mitotic kinesin function causes malformation or dysfunction of mitotic spindles, frequently resulting in cell cycle arrest and cell death. According to one embodiment of the invention, the compounds described herein inhibit the mitotic kinesin, KSP, particularly human KSP. In another embodiment, the compounds inhibit the mitotic kinesin, KSP, as well as modulating one or more of the human mitotic kinesins selected from the group consisting of HSET (see, U.S. Pat. No. 6,361,993, which is incorporated herein by reference); MCAK (see, U.S. Pat. No. 6,331,424, which is incorporated herein by reference); CENP-E (see, PCT Publication No. WO 99/13061, which is incorporated herein by reference); Kif4 (see, U.S. Pat. No. 6,440,684, which is incorporated herein by reference); MKLP1 (see, U.S. Pat. No. 6,448,025, which is incorporated herein by reference); Kif15 (see, U.S. Pat. No. 6,355,466, which is incorporated herein by reference); Kid (see, U.S. Pat. No. 6,387,644, which is incorporated herein by reference); Mpp1, CMKrp, KinI-3 (see, U.S. Pat. No. 6,461,855, which is incorporated herein by reference); Kip3a (see, PCT Publication No. WO 01/96593, which is incorporated herein by reference); Kip3d (see, U.S. Pat. No. 6,492,151, which is incorporated herein by reference); and RabK6.

The methods of inhibiting a mitotic kinesin comprise contacting an inhibitor of the invention with a kinesin, particularly a human kinesin, more particularly, human KSP or fragments and variants thereof. The inhibition can be of the ATP hydrolysis activity of the KSP kinesin and/or the mitotic spindle formation activity, such that the mitotic spindles are disrupted. Meiotic spindles may also be disrupted.

The present invention provides inhibitors of mitotic kinesins, in particular KSP and especially human KSP, for the treatment of disorders associated with cell proliferation. The compounds, compositions and methods are used to treat diseases of cellular proliferation, including, but not limited to cancer, hyperplasias, restenosis, cardiac hypertrophy, immune disorders, fungal disorders and inflammation.

Accordingly, the present invention relates to methods employing compounds represented by Formula Ia or Ib:

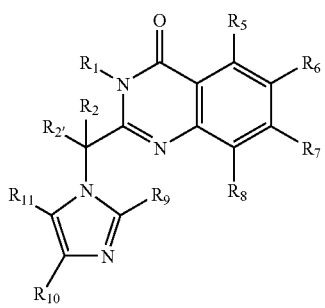

Formula Ia

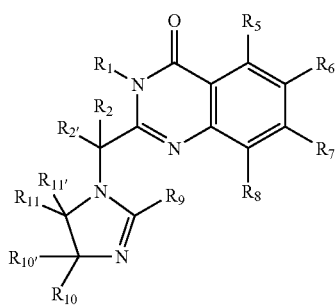

Formula Ib wherein

R₁ is chosen from hydrogen, optionally substituted alkyl-, optionally substituted aryl-, optionally substituted aralkyl-, optionally substituted heteroaryl-, and optionally substituted heteroaralkyl-;

$R_2$ and $R_{2'}$ are independently chosen from hydrogen, optionally substituted alkyl-, optionally substituted aryl-, optionally substituted aralkyl-, optionally substituted heteroaryl-, and optionally substituted heteroaralkyl-; or $R_2$ and $R_{2'}$ taken together form an optionally substituted 3- to 7-membered ring;

$R_5$, $R_6$, $R_7$ and $R_8$ are independently chosen from hydrogen, optionally substituted alkyl-, optionally substituted alkoxy, halogen, hydroxyl-, nitro, cyano, dialkylamino, alkylsulfonyl-, alkylsulfonamido, alkylthio, carboxyalkyl-, carboxamido, aminocarbonyl-, optionally substituted aryl-, optionally substituted aryloxy, optionally substituted heteroaryl-, and optionally substituted heteroaryloxy;

$R_9$ is chosen from hydrogen, optionally substituted alkyl-, optionally substituted aryl-, optionally substituted aralkyl-, and optionally substituted heteroaryl-; and $R_{10}$, $R_{10'}$, $R_{11}$, and $R_{11'}$ are independently hydrogen, optionally substituted alkyl-, optionally substituted aryl-, or optionally substituted aralkyl-, including single stereoisomers and mixtures of stereoisomers;

pharmaceutically acceptable salts of a compound of Formula Ia or Ib;

pharmaceutically acceptable solvates of a compound of Formula Ia or Ib; and pharmaceutically acceptable solvates of a pharmaceutically acceptable salt of a compound of Formula Ia or Ib. In a particular embodiment, the stereogenic center to which $R_2$ and $R_{2'}$ are attached is of the R configuration.

Nomenclature

The compounds of Formula Ia or Ib can be named and numbered in the manner (e.g., using AutoNom version 2.1 in ChemDraw or ISIS-DRAW) described below. For example, the compound:

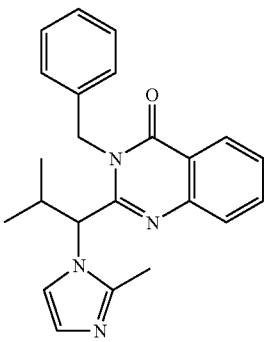

i.e., the compound according to Formula Ia where $R_1$ is benzyl-, $R_2$ is propyl- (or i-propyl-), $R_{2'}$ is hydrogen; $R_5$, $R_6$, $R_7$, $R_8$, $R_{10}$, and $R_{11}$ are hydrogen; and $R_9$ is methyl- can be named 3-benzyl-2-[2-methyl-1-(2-methyl-imidazol-1-yl)-propyl]-3H-quinazolin-4-one.

The compound having the structure

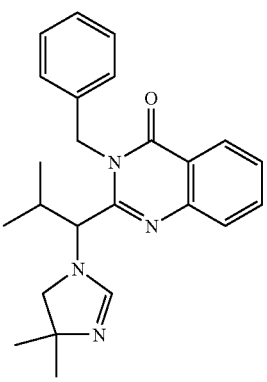

i.e., the compound according to Formula Ib where $R_1$ is benzyl-, $R_2$ is propyl- (or i-propyl-), $R_{2'}$ is hydrogen; $R_5$, $R_6$, $R_7$, $R_8$, $R_9$, $R_{11}$, and $R_{11'}$ are hydrogen; and $R_{10}$ and $R_{10'}$ are methyl- can be named 3-benzyl-2-[1-(4,4-dimethyl-4,5-dihydro-imidazol-1-yl)-2-methyl-propyl]-3H-quinazolin-4-one.

Synthetic Reaction Parameters

The compounds of Formula Ia or Ib can be prepared by following the procedures described with reference to the Reaction Schemes below.

Unless specified otherwise, the terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

In general, esters of carboxylic acids may be prepared by conventional esterification procedures, for example alkyl esters may be prepared by treating the required carboxylic acid with the appropriate alkanol, generally under acidic conditions. Likewise, amides may be prepared using conventional amidation procedures, for example amides may be prepared by treating an activated carboxylic acid with the appropriate amine. Alternatively, a lower-alkyl ester such as a methyl ester of the acid may be treated with an amine to provide the required amide, optionally in presence of trimethylalluminium following the procedure described in Tetrahedron Lett. 48, 4717-4173, (1977). Carboxyl groups may be protected as alkyl esters, for example methyl esters, which esters may be prepared and removed using conventional procedures, one convenient method for converting carbomethoxy to carboxyl is to use aqueous lithium hydroxide.

The salts and solvates of the compounds mentioned herein may as required be produced by methods conventional in the art. For example, if an inventive compound is an acid, a desired base addition salt can be prepared by treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; such as ethylenediamine, and cyclic amines, such as cyclohexylamine, piperidine, morpholine, and piperazine; as well as inorganic salts derived from sodium, calcium, potassium, magnesium, manganese, iron, copper, zinc, aluminum, and lithium.

If a compound is a base, a desired acid addition salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid, or the like.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Synthesis of the Compounds of Formula Ia and Ib

The compounds of Formula Ia and Ib can be prepared by following the procedures described in PCT Patent Application Serial No. US03/04713; PCT Publication Nos. WO 01/98278 and WO 01/30768, each of which is incorporated herein by reference for all purposes and with reference to the Reaction Schemes below.

Brief Description of Reaction Schemes

Reaction Scheme 1 illustrates synthesis of compounds of Formula 107 which are useful as intermediates in the synthesis of compounds of Formula Ia and Ib.

Reaction Schemes 2 and 3 illustrate the synthesis of compounds of Formula Ia from compounds of Formula 107.

Reaction Schemes 4 and 5 illustrate the synthesis of compounds of Formula Ib from compounds of Formula 107.

Reaction Scheme 6 illustrates the synthesis of compounds of Formula 603.

Reaction Scheme 7 illustrates the synthesis of compounds of Formula Ib from compounds of Formula 107.

Reaction Scheme 8 illustrates the synthesis of compounds of Formula 107 which are useful as intermediates in the synthesis of compounds of Formula Ia and Ib.

Reaction Scheme 9 illustrates the synthesis of compounds of Formula 809 which are useful as intermediates in the synthesis of compounds of Formula Ia and Ib.

Reaction Scheme 10 illustrates the synthesis of compounds of Formula 107 which are useful as intermediates in the synthesis of compounds of Formula Ia and Ib.

Starting Materials

The optionally substituted benzoic acids of Formula 101 and the other reagents are commercially available, e.g., from Aldrich Chemical Company, Milwaukee, Wis. or may be readily prepared by those skilled in the art using commonly employed synthetic methodology.

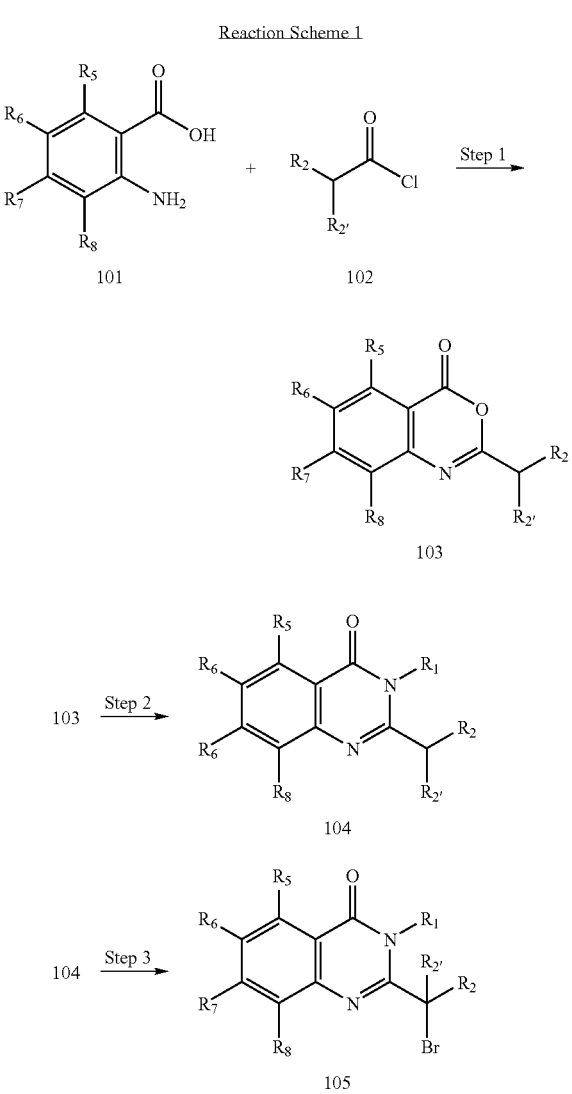

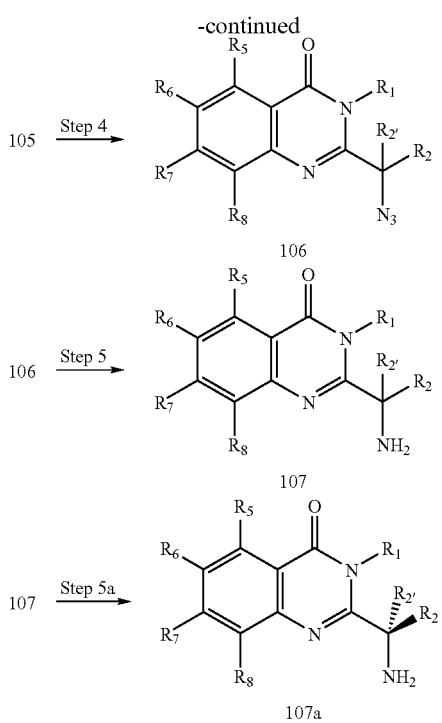

Preparation of Formula 103

Referring to Reaction Scheme 1, Step 1, to an optionally substituted benzoic acid (the compound of Formula 101) dissolved in an inert organic solvent (such as THF) in the presence of sodium bicarbonate and a dehydrating agent (such as $Na_2SO_4$) is added a slight molar excess of an optionally substituted acid chloride (the compound of Formula 102), maintaining about room temperature. Completion of the reaction is monitored, e.g., by TLC. Acetic anhydride is then added to the reaction mixture, which is heated to about 90-100° C., monitoring completion of the reaction (e.g., by TLC) followed by removal of the acetic anhydride under vacuum at about 80-100° C. The reaction mixture is cooled and the corresponding, optionally substituted benzo[d][1,3]oxazin-4-one (the compound of Formula 103) is isolated and purified.

Preparation of Formula 104

Referring to Reaction Scheme 1, Step 2, about 1.5 molar equivalents of a primary amine (such as $R_1NH_2$) and 1 molar equivalent of a compound of Formula 103 in an inert organic solvent (such as toluene) are heated to reflux. The reaction takes place over a period of 1 to 5 hours. After removal of water, ethylene glycol and sodium hydroxide are added to the reaction mixture and the temperature raised to 110-120° C. Completion of the reaction is monitored, e.g., by TLC. The corresponding, optionally substituted quinazolinone (a compound of Formula 104) is isolated and purified.

Preparation of Formula 105

Referring to Reaction Scheme 1, Step 3, a compound of Formula 104, dissolved in acetic acid and in the presence of sodium acetate, is heated to about 30° C., followed by the addition (with agitation) of a slight molar excess of bromine in acetic acid over a period of 2.5 hours. Completion is monitored, e.g., by TLC; if the starting material continues to be present, temperature is increased to about 50° C. until completion. The corresponding, optionally substituted quinazolinone of Formula 105 is isolated and purified.

Preparation of Formula 106

Referring to Reaction Scheme 1, Step 4, to 1.5 molar equivalents of sodium azide in an inert organic solvent (such as DMF) is slowly added 1 molar equivalent of a compound of Formula 105. The reaction takes place with agitation at a temperature of about 40° C. over a period of 3 to 10 hours. Completion is monitored, e.g., by TLC. The corresponding, optionally substituted quinazolinone azide of Formula 106 is isolated and purified.

Preparation of Formula 107

Referring to Reaction Scheme 1, Step 5, to a solution of triphenylphosphine dissolved in an inert organic solvent (such as THF) is added an azide of Formula 106, portionwise over about 15 minutes. The reaction takes place with agitation, maintaining the temperature at 20° C. over a period of 5 minutes to 1 hour. The reaction mixture is acidified, solvents removed followed by conventional work up to give the hydrochloride salt of the corresponding, optionally substituted quinazolinone of Formula 107, which is isolated and purified in the usual manner.

Preparation of Formula 107a

In certain compounds of the invention, particular stereoconfiguration can be preferred for the $R_2$ substituent, such as the (R) isomer, which can be obtained, e.g., as illustrated in optional Step 5a of Reaction Scheme 1. An amine of Formula 107 is dissolved in an inert organic solvent (such as IPA) and warmed to 60° C. In a separate vessel, a resolving agent (such as dibenzoyl-D-tartaric acid) is dissolved, preferably in the same warm solvent, and then quickly added (with agitation) to the warm amine solution. The reaction mixture is left to crystallize by cooling to room temperature over 16 hours under continuing agitation. The desired isomer, e.g., the (R) isomer illustrated as Formula 107a, is isolated and purified in the usual manner.

For the sake of brevity in the remaining description of the synthesis of compounds of Formula Ia or Ib, it should be understood that either single isomer or a mixture of isomers may be employed to give the corresponding product.

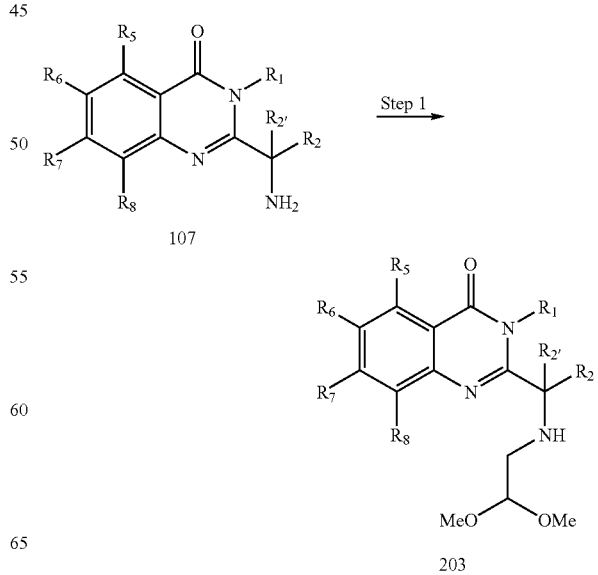

-continued

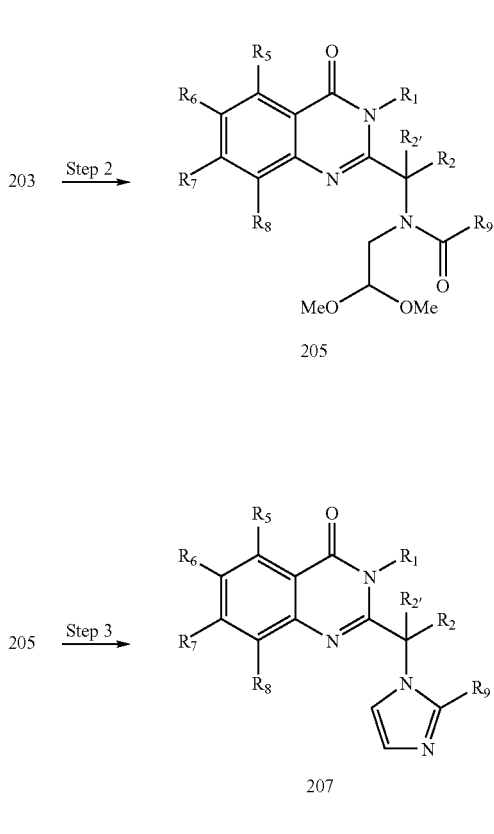

Preparation of Formula 203

Referring to Reaction Scheme 2, Step 1, to an optionally substituted compound of Formula 107 dissolved in a polar, aprotic solvent (such as DMF) in the presence of a base (such as potassium carbonate) is added one equivalent of an optionally substituted suitably protected aldehyde having a halogen substitutent. The solution is heated at reflux, monitoring completion of the reaction (e.g., by TLC). The reaction mixture is cooled and the corresponding, optionally substituted quinazolinone of Formula 203 is isolated and purified.

Preparation of Formula 205

Referring to Reaction Scheme 2, Step 2, to an optionally substituted compound of Formula 203 in an inert solvent (such as dichloromethane) in the presence of about 1.5 molar equivalents of an amine base (such as triethylamine) is added about 1.5 molar equivalents of an $R_9$ acid chloride where $R_9$ is as described above. The reaction takes place, with stirring, at room temperature over a period of 4 to 24 hours. Completion is monitored, e.g., by TLC. The corresponding compound of Formula 205 is isolated and purified.

Preparation of Formula 207

Referring to Reaction Scheme 2, Step 3, a solution of a compound of Formula 205 and an excess of ammonium acetate in acetic acid is heated at reflux for 1-4 hours. Completion is monitored, e.g., by TLC. The corresponding compound of Formula 207 is isolated and purified.

Reaction Scheme 3

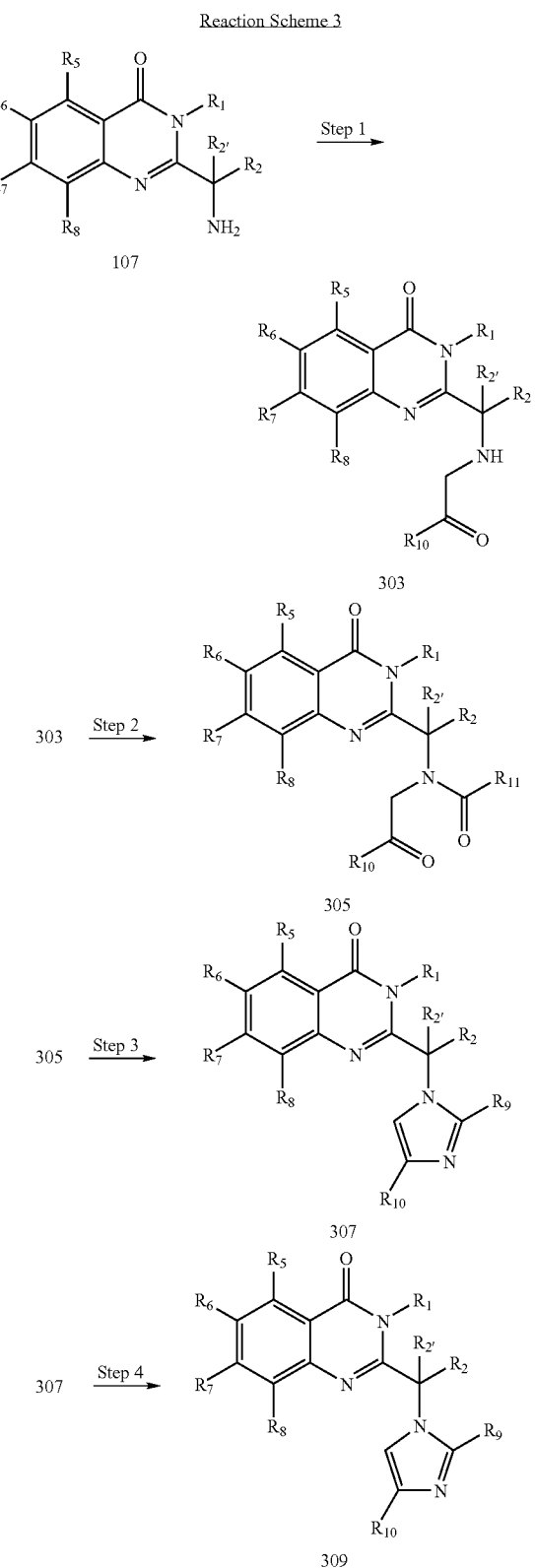

Preparation of Formula 303

Referring to Reaction Scheme 3, Step 1, a suspension of a compound of Formula 107, an alpha-haloketone reagent of the Formula $R_{10}(CO)CH_2X$ wherein X is a leaving group, preferably, a halide, and about an equivalent of a base, such as potassium carbonate in a polar, aprotic solvent such as DMF is stirred at room temperature. The reaction is diluted with water and the resulting solid is used in the subsequent step without further purification.

Preparation of Formula 305

Referring to Reaction Scheme 3. Step 2, a solution of the compound from previous step, about an equivalent of an amine base, such as triethylamine and about an equivalent of an acid chloride (such as p-toluoyl chloride) in an organic solvent such as methylene chloride is stirred at room temperature for several hours. Completion is monitored, e.g., by TLC. The corresponding compound of Formula 305 is isolated and purified.

Preparation of Formula 307

Referring to Reaction Scheme 3, Step 3, a solution of a compound of Formula 305 and an excess of ammonium acetate in acetic acid is heated at reflux using a Dean-Stark trap and condenser. Completion is monitored, e.g., by TLC. The corresponding compound of Formula 307 is isolated and purified.

Preparation of Formula 309

Optionally, in the event that group $R_{10}$ comprises a functionality bearing a protecting group, the protecting group is removed. Thus, if $R_{10}$ further comprises an amine bearing a Pht group, the protecting group is removed as shown in Reaction Scheme 3, Step 4. A solution of a compound of Formula 307 and an excess of anhydrous hydrazine in a polar, protic solvent such as ethanol is heated at reflux. The reaction is cooled to about 5° C. and any precipitate is filtered off. The filtrate is concentrated in vacuo and purified to yield a compound of Formula 309.

Reaction Scheme 4

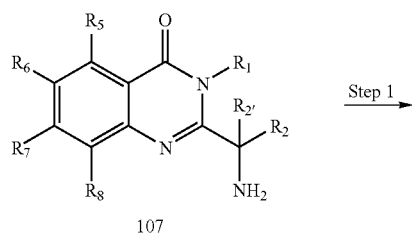

107

Step 1

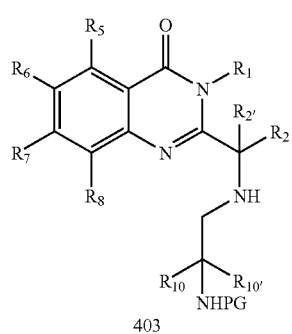

403

-continued

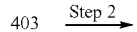

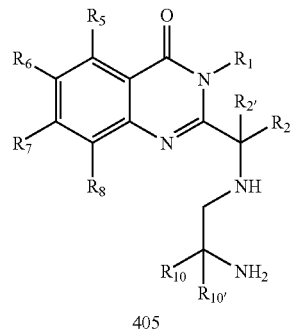

405

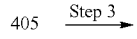

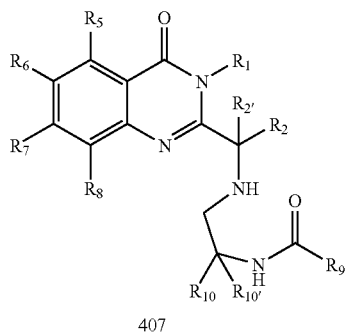

407

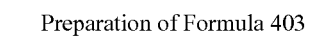

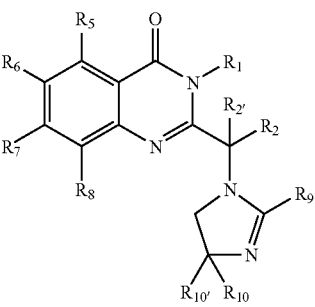

409

Preparation of Formula 403

Referring to Reaction Scheme 4, Step 1, reductive amination of amines of Formula 107 (prepared as described in WO 0130768) with an optionally substituted, aldehyde-containing carbamic acid ester (Seki et. al. *Chem. Pharm. Bull.* 1996, 44, 2061) gives urethane intermediates. Removal of the Boc-protecting group furnishes amines of Formula 405.

More specifically, to a solution of a compound of Formula 107 and an equivalent of a suitably protected aldehyde (Seki et. al. *Chem. Pharm. Bull.* 1996, 44, 2061) in dichloromethane is added a slight excess of a reducing agent, such as sodium triacetoxyborohydride. The resultant cloudy mixture is maintained at ambient temperature. Completion is monitored, e.g., by TLC. The corresponding compound of Formula 403 is isolated and used in the subsequent step without purification.

Preparation of Formula 405

Referring to Reaction Scheme 4, Step 2, the amine protecting group, PG, is then removed. For example, when PG is Boc, to a solution of a compound of Formula 403 in a polar, aprotic solvent such as dichloromethane is added a strong acid such as trifluoroacetic acid. The resultant solution is maintained at ambient temperature overnight and concentrated under reduced pressure. The residue is isolated and purified to give a compound of Formula 405 which was used in the subsequent step without purification.

Preparation of Formula 407

Referring to Reaction Scheme 4, Step 3, to a solution of a compound of Formula 405 in a polar, aprotic solvent such as dichloromethane is added an excess, preferably about two equivalents of an amine base such as triethylamine, followed by about an equivalent or slight excess of an acid chloride. The resultant solution is stirred at ambient temperature for about 3 hours. Completion is monitored, e.g., by TLC. The corresponding compound of Formula 407 is isolated and purified.

Preparation of Formula 409

Referring to Reaction Scheme 4, Step 4, a solution of a compound of Formula 407 in an excess of phosphorus oxychloride is heated at reflux. After 8 hours, the reaction mixture is allowed to cool to ambient temperature and concentrated under reduced pressure. The corresponding compound of Formula 409 is isolated and purified.

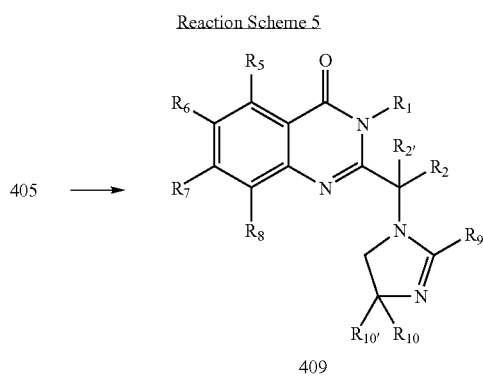

Preparation of Formula 409

As an alternative to Steps 3 and 4 of Reaction Scheme 4, acylation of primary amines of Formula 405, followed by acetic acid mediated cyclization, can proceed without isolation of the intermediate amides to provide the target compound of Formula 409. This route is shown in Reaction Scheme 5.

More specifically, to a solution of a compound of Formula 405 in a polar, aprotic solvent such as dichloromethane is added an excess, preferably about two equivalents of an amine base, such as triethylamine, followed by about an equivalent of an acid chloride. The resultant solution is stirred at ambient temperature for 2 hours, then evaporated under reduced pressure. The resultant solid is treated with glacial acetic acid, then the resultant suspension is heated at reflux for about 48 hours. The reaction is cooled to ambient temperature then evaporated under reduced pressure. The corresponding compound of Formula 409 is isolated and purified.

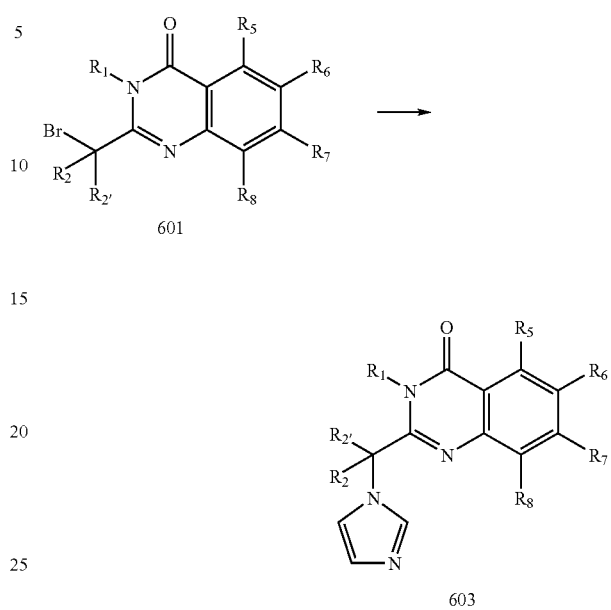

Preparation of Compounds of Formula 603

Referring to Reaction Scheme 6, to a solution of a compound of Formula 601 in a nonpolar, aprotic solvent such as DMF are added a base such as triethylamine and an excess (preferably, about 1.5 equivalents) of imidazole followed by about an equivalent of tetrabutylammonium iodide. The resultant solution is heated to about 90° C., stirred for about 18 h and allowed to cool to room temperature. The product, a compound of Formula 603, is isolated and purified.

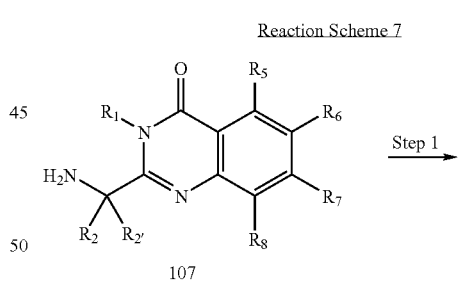

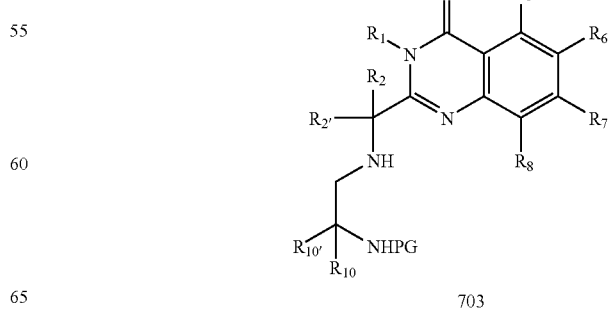

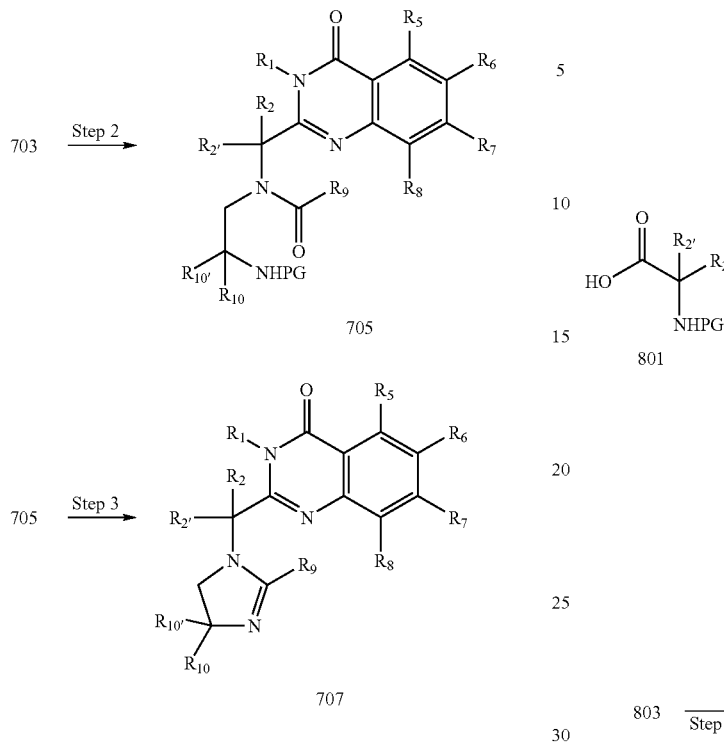

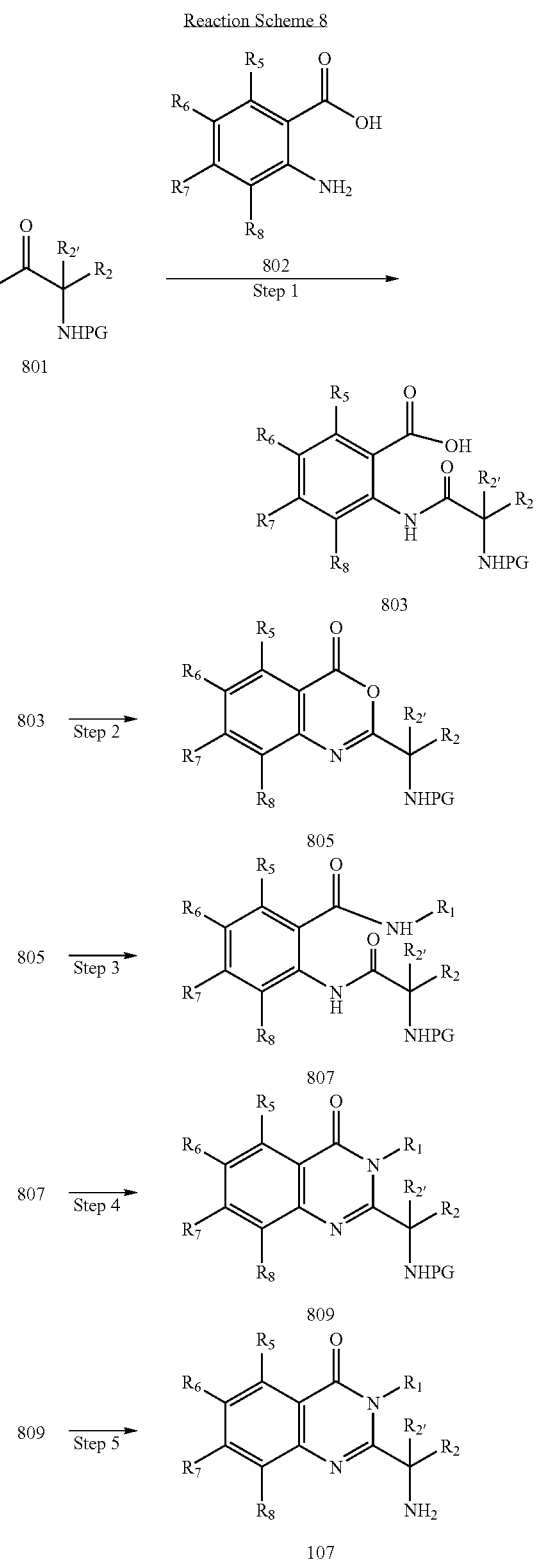

Preparation of Compounds of Formula 703

Referring to Reaction Scheme 7, Step 1, to a solution of a compound of Formula 107 and an excess of an optionally substituted, aldehyde-containing carbamic acid ester such as ((S)-4-benzyloxycarbonylamino-1-formyl-butyl)-carbamic acid tert-butyl ester) in a nonpolar, aprotic solvent such as $CH_2Cl_2$ is added sodium triacetoxyborohydride. The mixture is stirred overnight. The product, a compound of Formula 703, is isolated and purified.

Preparation of Compounds of Formula 705

Referring to Reaction Scheme 7, Step 2, to a solution of a compound of Formula 703 in a nonpolar, aprotic solvent such as toluene is added a base such as triethylamine followed by dropwise addition of an excess of an acid chloride of the formula $R_9$—COCl. The reaction mixture is heated to about 80° C. for about 18 h, then at reflux for about 4 h. The product, a compound of Formula 705, is isolated and purified.

Preparation of Compounds of Formula 707

Referring to Reaction Scheme 7, Step 3, a solution of a compound of Formula 705 in a solvent such as $CH_2Cl_2$/TFA (preferably, about 4:1 $CH_2Cl_2$/TFA) is stirred at room temperature. The reaction mixture is concentrated under reduced pressure and the residue is diluted with a nonpolar, aprotic solvent such as $CH_2Cl_2$ and washed with aqueous base. The aqueous layer is extracted with a nonpolar, aprotic solvent such as $CH_2Cl_2$ and the combined extracts are dried, filtered and concentrated under reduced pressure. The residue is diluted with a nonpolar, aprotic solvent such as THF and aqueous base (preferably, saturated aqueous $NaHCO_3$). The mixture is stirred at room temperature for 10 days. The product, a compound of Formula 707, is isolated and purified.

Preparation of Compounds of Formula 803

Referring to Reaction Scheme 8, Step 1, a compound of Formula 801 (e.g., an N-protected, chiral, naturally occuring or substituted amino acid such as valine; preferably N-Boc- D-valine) is converted to the corresponding compound of Formula 803. Any naturally occurring and substituted α-amino acids can be employed as the compound of Formula 801, such as alanine, valine, leucine, isoleucine, phenylglycine, phenylalanine, serine, threonine, cysteine, methionine, tryptophan, tyrosine, asparagine, glutamine, asparaginate, glutamate, lysine, arginine, histidine and 2-aminobutyric acid; preferably alanine, valine, leucine, isoleucine, phenylglycine or 2-aminobutyric acid. Art-recognized N-protecting groups can be employed in the compound of Formula 801, including Boc, CBZ, phthalide, alloc, and teoc.

The compound of Formula 801 is dissolved in an organic solvent (such as THF) in the presence of 1 to 2 molar equivalents of a base (such as N-methylmorpholine) and cooled to 0° C. Approximately 1 to 2 molar equivalents of isobutyl chloroformate is slowly added preferably with stirring. The mixture is maintained at 0° C. and stirred for 1 to 2 hours (preferably 1.5 hours) to give the corresponding mixed anhydride (not shown). The mixed anhydride is carried forward without isolation or purification by the addition in one portion of an equimolar amount of an optionally substituted anthranilic acid of Formula 802 followed by the addition of a second equimolar amount of the base (such as N-methylmorpholine). The reaction takes place at 0° C. over a period of 1 to 5 hours to give the corresponding compound of Formula 803 (which can also be carried forward without isolation or purification).

Preparation of Compounds of Formula 805

Referring to Reaction Scheme 8, Step 2, a compound of Formula 803 is converted to the corresponding compound of Formula 805. An additional 1 to 2 molar equivalents of isobutyl chloroformate is added to a compound of Formula 803 along with the addition of 1 to 2 molar equivalents of a base (such as N-methylmorpholine). The reaction takes place at 0° C. over a period of 1 to 3 hours to give the corresponding compound of Formula 805 (which can also be carried forward without isolation or purification).

Preparation of Compounds of Formula 807 and 809

Referring to Reaction Scheme 1, Step 3, a compound of Formula 805 is converted to the corresponding compounds of Formula 807 and 809. One to 3 molar equivalents of an amine of Formula $R_1NH_2$ are added with continued stirring to a compound of Formula 805. The reaction takes place at 0° C. to the corresponding compounds of Formula 807 and Formula 809, each of which can be isolated and purified.

Preparation of Compounds of Formula 809

Referring to Reaction Scheme 1, Step 4, a compound of Formula 807 is converted to the corresponding quinazolinone of Formula 809. A compound of Formula 807 is dissolved in an organic solvent (e.g., 1,4-dioxane/ethylene glycol 2:1 or dimethoxyethane), contacted with a slight to twice molar excess of a cyclo-dehydration reagent (e.g., lithium hydroxide monohydrate, HMDS, phosphorous oxychloride, oxalyl chloride, thionyl chloride, Burgess' reagent, $Ph_3P/I_2$, or a Vilsmeier reagent (DMF with phosphorous oxychloride, or DMF with thionyl chloride), preferably HMDS) and heated to reflux. The reaction takes place at reflux over a period of 3 to 36 hours, followed by cooling and optionally acidification of the mixture to give a suspension of the corresponding quinazolinone of Formula 809, which is then isolated and purified by conventional procedures. Reaction time and work-up will depend on the cyclo-dehydration reagent that is employed.

Preparation of Compounds of Formula 107

Referring to Reaction Scheme 8, Step 7, the amino protecting group of a compound of Formula 809 is removed. For example, to a solution of a compound of Formula 809 wherein the amino protecting group, PG, is Boc in a polar, aprotic solvent such as dichloromethane is added trifluoroacetic acid, while maintaining the temperature at about 0° C. The resulting solution is then stirred at room temperature for one hour and concentrated in vacuo. The product, a compound of Formula 107, is isolated and used in the next step without further purification. One of skill in the art will readily appreciate that the removal of other protecting groups can be accomplished using conditions known in the art. See, e.g., Greene, et al. supra.

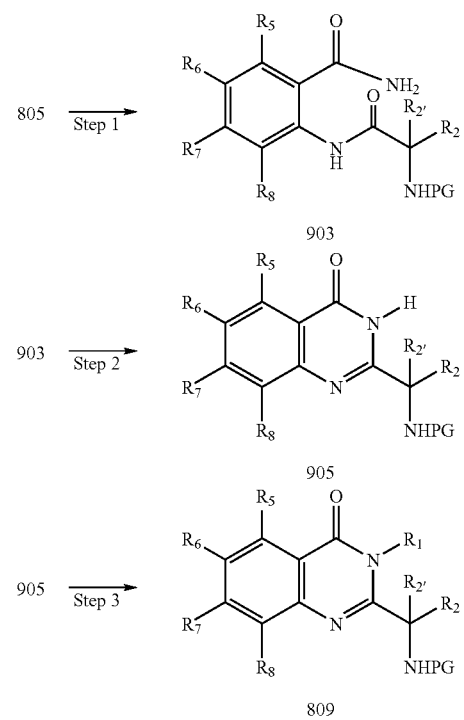

Reaction Scheme 9

Preparation of Compounds of Formula 903

Referring to Reaction Scheme 9, Step 1, a compound of Formula 805 is converted to the corresponding carbamide of Formula 903. Gaseous ammonia is bubbled through a solution of the compound of Formula 805. The reaction takes place with stirring at 0° C. over a period of 1 to 3 hours followed by isolation and purification via conventional procedures.

Preparation of Compounds of Formula 905

Referring to Reaction Scheme 9, Step 2, a compound of Formula 903 is converted to the corresponding quinazolinone of Formula 905. The compound of Formula 903 is dissolved in an organic solvent (preferably THF) and contacted with a slight molar excess of a strong base (preferably lithium hydroxide monohydrate) to give the corresponding compound of Formula 905. The reaction takes place at reflux over a period of about 30 minutes to 2 hours, followed by cooling and acidification of the mixture to give a suspension, which is then isolated and purified via conventional procedures.

Preparation of Compounds of Formula 809

Referring to Reaction Scheme 9, Step 3, a compound of Formula 905 is converted to the corresponding 3-N-substituted quinazolinone of Formula 809. The compound of Formula 807 is dissolved in an organic solvent (e.g., DMF) and N-substituted via contact with a compound of Formula $R_rX$ wherein X is a leaving group (preferably a halide or tosylate) in the presence of an alkaline metal carbonate or hydride. The reaction takes place at room temperature over a period of 10 to 20 hours to give the corresponding compound of Formula 809, which is isolated and purified.

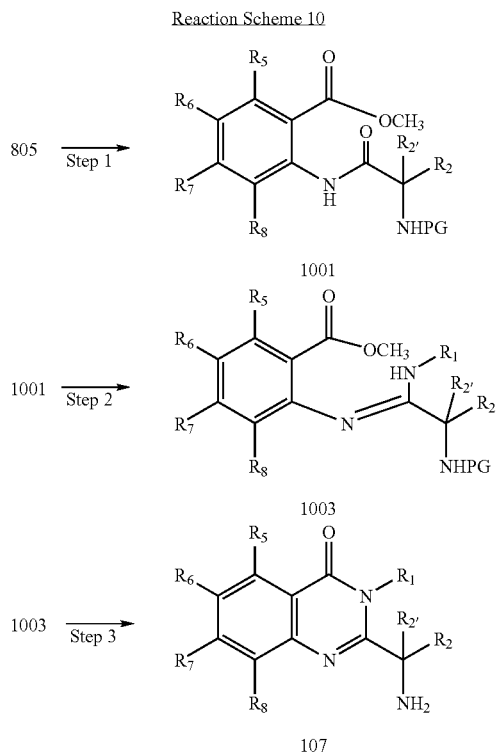

Reaction Scheme 10

Preparation of Compounds of Formula 1001

Referring to Reaction Scheme 10, Step 1, a compound of Formula 805 is opened with methanol and converted to the corresponding ester of Formula 1001. The compound of Formula 1001 is isolated and optionally-purified.

Preparation of Compounds of Formula 1003

Referring to Reaction Scheme 10, Step 2, an ester of Formula 1100 is converted to the corresponding amidine of Formula 1003.

Preparation of Compounds of Formula 107

Referring to Reaction Scheme 10, Step 3, an amidine of Formula 1003 is cyclized to afford the corresponding compound of Formula 107.

Preferred Processes and Last Steps

A compound of Formula Ia or Ib is optionally contacted with a pharmaceutically acceptable acid or base to form the corresponding acid or base addition salt.

A pharmaceutically acceptable acid addition salt of a compound of Formula Ia or Ib is optionally contacted with a base to form the corresponding free base of Formula Ia or Ib.

A pharmaceutically acceptable base addition salt of a compound of Formula Ia or Ib is optionally contacted with an acid to form the corresponding free acid of Formula Ia or Ib.

PARTICULAR EMBODIMENTS OF COMPOUNDS OF THE INVENTION $R_1$

When considering the compounds of Formula Ia or Ib, in one embodiment, $R_1$ is selected from hydrogen, optionally substituted $C_1$-$C_8$ alkyl-, optionally substituted aryl-, optionally substituted heteroaryl-, optionally substituted aryl-$C_1$-$C_4$-alkyl-, and optionally substituted heteroaryl-$C_1$-$C_4$-alkyl- (more preferably optionally substituted aryl- and optionally substituted aryl-$C_1$-$C_4$-alkyl-). In a more particular embodiment $R_1$ is selected from hydrogen, optionally substituted $C_1$-$C_4$ alkyl-, optionally substituted phenyl-$C_1$-$C_4$-alkyl-, optionally substituted naphthalenylmethyl-, optionally substituted phenyl-, and naphthyl-. Even more particularly, $R_1$ is optionally substituted phenyl-$C_1$-$C_4$-alkyl-, optionally substituted heteroaryl-$C_1$-$C_4$-alkyl-, or naphthalenylmethyl-. Yet more particularly, $R_1$ is benzyl-, cyanobenzyl-, methoxybenzyl-, or naphthalenylmethyl-. Most particularly, $R_1$ is benzyl-.

$R_2$ and $R_{2'}$

When considering the compounds of Formula Ia or Ib, and as will be appreciated by those skilled in the art, the compounds described herein possess a potentially chiral center at the carbon to which $R_2$ and $R_{2'}$ are attached. The $R_2$ and $R_{2'}$ groups may be the same or different; if different, the compound is chiral (i.e., has a stereogenic center). When $R_2$ and $R_{2'}$ are different, in particular embodiments $R_{2'}$ is hydrogen and $R_2$ is other than hydrogen. The invention contemplates the use of pure enantiomers and mixtures of enantiomers, including racemic mixtures, although the use of a substantially optically pure enantiomer will generally be preferred. The term "substantially pure" means having at least about 95% chemical purity with no single impurity greater than about 1%. The term "substantially optically pure" or "enantiomerically pure" means having at least about 97.5% enantiomeric excess. In a particular embodiment, the stereogenic center to which $R_2$ and $R_{2'}$ are attached is of the R configuration.

When considering the compounds of Formula Ia or Ib, $R_2$ and $R_{2'}$ are independently chosen from hydrogen, optionally substituted alkyl-, optionally substituted aryl-, optionally substituted aralkyl-, optionally substituted heteroaryl-, and optionally substituted heteroaralkyl-.

In one embodiment, $R_2$ and $R_{2'}$ taken together form a 3- to 7-membered ring which may optionally be substituted one or more of the following groups: hydroxyl, halogen (particularly chloro and fluoro), optionally substituted $C_1$-$C_4$ alkyl- (particularly methyl-), $C_1$-$C_4$ alkoxy (particularly methoxy), cyano substituted amino, or carbamyl-.

In one embodiment, $R_2$ is optionally substituted $C_1$-$C_4$ alkyl-, and $R_{2'}$ is hydrogen or optionally substituted $C_1$-$C_4$ alkyl-. More suitably, $R_{2'}$ is hydrogen and $R_2$ is optionally substituted $C_1$-$C_4$ alkyl-. In a most particular embodiment $R_2$ is chosen from methyl-, ethyl-, propyl- (particularly, c-propyl- or i-propyl-), butyl- (particularly, t-butyl-) methylthioethyl-, methylthiomethyl-, aminobutyl-, (CBZ)aminobutyl-, cyclohexylmethyl-, benzyloxymethyl-, methylsulfanylethyl-, methylsulfanylmethyl-, and hydroxymethyl-, and $R_{2'}$ is hydrogen. Especially chosen embodiments are when $R_{2'}$ is hydrogen and $R_2$ is ethyl- or propyl- (particularly c-propyl- or i-propyl-). Even more particularly, $R_2$ is i-propyl-. Yet more particularly, the stereogenic center to which $R_2$ and $R_{2'}$ is attached is of the R configuration.

In one embodiment, if either $R_2$ or $R_{2'}$ is hydrogen, then the other is not hydrogen. In another embodiment, both $R_2$ and $R_{2'}$ are hydrogen.

$R_5$, $R_6$, $R_7$, and $R_8$

In other embodiments $R_5$, $R_6$, $R_7$, and $R_8$ are independently chosen from hydrogen, hydroxyl, halogen (particularly chloro and fluoro), optionally substituted $C_1$-$C_4$ alkyl- (particularly methyl-), $C_1$-$C_4$ alkoxy (particularly methoxy), cyano substituted amino, or carbamyl-. More particularly, $R_5$, $R_6$, $R_7$, and $R_8$ are methoxy, hydrogen or halo. For each of the specific substituents: $R_5$ is hydrogen or halo; $R_6$ is hydrogen, optionally substituted $C_1$-$C_4$ alkyl- (particularly, methyl-) or halo; $R_7$ is hydrogen, halo, optionally substituted $C_1$-$C_4$ alkyl- (particularly, methyl- or trifluoromethyl-), $C_1$-$C_4$ alkoxy (particularly, methoxy), cyano, substituted amino, or carbamyl-; and $R_8$ is hydrogen, $C_1$-$C_4$ alkyl- (particularly, methyl-), $C_1$-$C_4$ alkoxy (particularly, methoxy), hydroxy, or halo. Still more particularly are the compounds where only one of $R_5$, $R_6$, $R_7$, and $R_8$ is not hydrogen, especially $R_7$. Another particular embodiment is drawn to the compounds where $R_7$ and $R_8$ are not hydrogen.

$R_9$

In a particular embodiment, $R_9$ is chosen from hydrogen, optionally substituted alkyl-, optionally substituted aryl-, optionally substituted aralkyl-, and optionally substituted heteroaryl-.

More particularly, $R^9$ is hydrogen;
optionally substituted lower-alkyl- (especially, methyloxymethyl-, aminoethyl-, methyl-, ethyl-, or propyl-);
aryl- (especially phenyl-);
substituted aryl- (especially phenyl- substituted with one or more of the following:
  optionally substituted lower-alkyl- (especially, methyl-, ethyl-, methoxymethyl-, or trifluoromethyl-), lower-alkoxy (especially, methoxy or methylenedioxy-), halo, aminocarbonyl-, or cyano);
aralkyl- (especially benzyl- or phenylvinyl-);
heteroaryl- (especially furyl-, thiophenyl-, pyridinyl-, isoxazolyl-, or quinoxalinyl-);
substituted heteroaryl- (especially furyl-, thiophenyl-, pyridinyl-, quinoxalinyl-, or isoxazolyl- substituted with one or more of the following optionally substituted lower-alkyl- (especially, methyl-, methoxymethyl-, or trifluoromethyl-), halo, lower-alkoxy-, or cyano); or
substituted aralkyl- (especially substituted benzyl- or substituted styrenyl-).

Yet more particularly, $R_9$ is hydrogen; methyl-; ethyl-; propyl-; phenyl-; tolyl-; ethylphenyl-; halophenyl-; acetylaminophenyl-; cyanophenyl-; halomethylphenyl-; polyhalophenyl-; methyoxymethyl-; methoxyethyl-; methoxyphenyl-; dimethoxyphenyl-; methylenedioxyphenyl-; trifluoromethylphenyl-; furyl-; thiophenyl-; pyridinyl-; halomethylpyridinyl-; isoxazolyl-; methylisoxzolyl-; dimethylaminophenyl-; diethylaminophenyl-; isopropylphenyl-; or quinoxalinyl-.

$R_{10}$, $R_{10'}$, $R_{11}$, and $R_{11'}$

When considering compounds of Formula Ia or Ib, in a particular embodiment, $R_{10}$, $R_{10'}$, $R_{11}$, and $R_{11'}$ are independently selected from the group consisting of hydrogen, optionally substituted alkyl-, optionally substituted aryl-, and optionally substituted aralkyl-.

More particularly, $R_{10}$ and $R_{10'}$ are independently selected from the group consisting of hydrogen; hydroxymethyl-; aminomethyl-; acetylaminomethyl-; (carboxymethyl-amino)-methyl-; aminoethyl-; acetylaminoethyl-; (carboxymethyl-amino)-ethyl-; hydroxyethyl-; aminopropyl-; acetylaminopropyl-; (carboxymethyl-amino)-propyl-; hydroxypropyl-; methyl-; ethyl-; and propyl-.

In a particular embodiment, $R_{11}$ and $R_{11'}$ are independently selected from the group consisting of hydrogen and optionally substituted lower-alkyl-. More particularly, $R_{11}$ and $R_{11'}$ are hydrogen.

Particular Subgenus

In a particular subgenus of Formula Ia, $R_1$ is benzyl-, halobenzyl-, methoxybenzyl-, cyanobenzyl-, or naphthylmethyl-; $R_2$ is chosen from ethyl- and propyl-; $R_2'$ is hydrogen; $R_5$ is hydrogen; $R_6$ is hydrogen; $R_7$ is halo; $R_8$ is hydrogen; and $R_9$ is substituted phenyl-; $R_{10}$ is methyl-, hydrogen, or amino lower-alkyl- (aminomethyl-, aminoethyl-, aminopropyl-); and $R_{11}$ is hydrogen.

In a particular subgenus of Formula Ib, $R_1$ is benzyl-, halobenzyl-, methoxybenzyl-, cyanobenzyl-, or naphthylmethyl-; $R_2$ is chosen from ethyl- and propyl-; $R_2'$ is hydrogen; $R_5$ is hydrogen; $R_6$ is hydrogen; $R_7$ is halo; $R_8$ is hydrogen; and $R_9$ is substituted phenyl-; $R_{10}$ and $R_{10'}$ are methyl-, hydrogen, or amino lower-alkyl-(aminomethyl-, aminoethyl-, aminopropyl-); and $R_{11}$ and $R_{11'}$ are hydrogen.

In a particular subgenus of Formula Ia, $R_1$ is chosen from hydrogen, optionally substituted alkyl-, optionally substituted aryl-, optionally substituted aryl-$C_1$-$C_4$-alkyl-, optionally substituted heteroaryl-, and optionally substituted heteroaryl-$C_1$-$C_4$-alkyl-;

$R_2$ and $R_2'$ are independently chosen from hydrogen, optionally substituted alkyl-, optionally substituted aryl-, optionally substituted aryl-$C_1$-$C_4$-alkyl-, optionally substituted heteroaryl-, and optionally substituted heteroaryl-$C_1$-$C_4$-alkyl-; or $R_2$ and $R_2'$ taken together form an optionally substituted 3- to 7-membered ring;

$R_5$, $R_6$, $R_7$ and $R_8$ are independently chosen from hydrogen, optionally substituted alkyl-, optionally substituted alkoxy, halogen, hydroxyl-, nitro, cyano, dialkylamino, alkylsulfonyl-, alkylsulfonamido, alkylthio, carboxyalkyl-, carboxamido, aminocarbonyl-, optionally substituted aryl-, optionally substituted aryloxy, optionally substituted heteroaryl-, and optionally substituted heteroaryloxy;

$R_9$ is chosen from hydrogen, optionally substituted alkyl-, optionally substituted aryl-, optionally substituted aralkyl-, and optionally substituted heteroaryl-; and $R_{10}$, $R_{10'}$, $R_{11}$, and $R_{11'}$ are independently hydrogen, optionally substituted alkyl-, optionally substituted aryl-, or optionally substituted aralkyl, provided that $R_1$ is not substituted phenyl when $R_2$ is methyl and $R_{2'}$ is hydrogen.

Particular Compounds

Particular compounds include:

3-Benzyl-7-chloro-2-{1-[2-(4-chloro-phenyl)-4,4-dimethyl-4,5-dihydro-imidazol-1-yl]-2-methyl-propyl}-3H-quinazolin-4-one;

3-Benzyl-2-{1-[2-(4-bromo-phenyl)-4,4-dimethyl-4,5-dihydro-imidazol-1-yl]-2-methyl-propyl}-7-chloro-3H-quinazolin-4-one;

3-Benzyl-7-chloro-2-{1-[2-(4-methoxy-phenyl)-4,4-dimethyl-4,5-dihydro-imidazol-1-yl]-2-methyl-propyl}-3H-quinazolin-4-one;

3-Benzyl-7-chloro-2-{1-[4,4-dimethyl-2-(4-trifluoromethyl-phenyl)-4,5-dihydro-imidazol-1-yl]-2-methyl-propyl}-3H-quinazolin-4-one;

3-Benzyl-7-chloro-2-[1-(4,4-dimethyl-2-thiophen-2-yl-4,5-dihydro-imidazol-1-yl)-2-methyl-propyl]-3H-quinazolin-4-one;

3-Benzyl-7-chloro-2-[1-(2-furan-2-yl-4,4-dimethyl-4,5-dihydro-imidazol-1-yl)-2-methyl-propyl]-3H-quinazolin-4-one;

3-Benzyl-7-chloro-2-[1-(2-methoxymethyl-4,4-dimethyl-4,5-dihydro-imidazol-1-yl)-2-methyl-propyl]-3H-quinazolin-4-one;

3-Benzyl-7-chloro-2-[1-(4,4-dimethyl-2-m-tolyl-4,5-dihydro-imidazol-1-yl)-2-methyl-propyl]-3H-quinazolin-4-one;

3-Benzyl-7-chloro-2-{1-[2-(3-chloro-phenyl)-4,4-dimethyl-4,5-dihydro-imidazol-1-yl]-2-methyl-propyl}-3H-quinazolin-4-one;

Benzyl-7-chloro-2-[(R)-1-(4,4-dimethyl-2-p-tolyl-4,5-dihydro-imidazol-1-yl)-2-methyl-propyl]-3H-quinazolin-4-one;

3-Benzyl-7-chloro-2-{1-[2-(4-fluoro-phenyl)-4,4-dimethyl-4,5-dihydro-imidazol-1-yl]-2-methyl-propyl}-3H-quinazolin-4-one;

3-Benzyl-7-chloro-2-[1-(4,4-dimethyl-2-phenyl-4,5-dihydro-imidazol-1-yl)-2-methyl-propyl]-3H-quinazolin-4-one trifluoroacetate;

3-Benzyl-7-chloro-2-{1-[2-(3,4-dichloro-phenyl)-4,4-dimethyl-4,5-dihydro-imidazol-1-yl]-2-methyl-propyl}-3H-quinazolin-4-one;

3-Benzyl-7-chloro-2-{1-[2-(3,4-dimethoxy-phenyl)-4,4-dimethyl-4,5-dihydro-imidazol-1-yl]-2-methyl-propyl}-3H-quinazolin-4-one;

2-[1-(2-Benzo[1,3]dioxol-5-yl-4,4-dimethyl-4,5-dihydro-imidazol-1-yl)-2-methyl-propyl]-3-benzyl-7-chloro-3H-quinazolin-4-one;

3-{1-[1-(3-Benzyl-7-chloro-4-oxo-3,4-dihydro-quinazolin-2-yl)-2-methyl-propyl]-4,4-dimethyl-4,5-dihydro-1H-imidazol-2-yl}-benzonitrile;

3-Benzyl-7-chloro-2-{1-[2-(2-chloro-6-methyl-pyridin-4-yl)-4,4-dihydro-imidazol-1-yl]-2-methyl-propyl}-3H-quinazolin-4-one;

3-Benzyl-7-chloro-2-{1-[4,4-dimethyl-2-(5-methyl-isoxazol-3-yl)-4,5-dihydro-imidazol-1-yl]-2-methyl-propyl}-3H-quinazolin-4-one;

3-Benzyl-7-chloro-2-{1-[2-(4-fluoro-3-methyl-phenyl)-4,4-dimethyl-4,5-dihydro-imidazol-1-yl]-2-methyl-propyl}-3H-quinazolin-4-one;

3-Benzyl-7-chloro-2-{1-[2-(3,5-dimethoxy-phenyl)-4,4-dimethyl-4,5-dihydro-imidazol-1-yl]-2-methyl-propyl}-3H-quinazolin-4-one;

3-Benzyl-7-chloro-2-{1-[2-(2,3-difluoro-4-methyl-phenyl)-4,4-dimethyl-4,5-dihydro-imidazol-1-yl]-2-methyl-propyl}-3H-quinazolin-4-one;

3-Benzyl-7-chloro-2-{1-[2-(3-dimethylamino-phenyl)-4,4-dimethyl-4,5-dihydro-imidazol-1-yl]-2-methyl-propyl}-3H-quinazolin-4-one;

3-Benzyl-7-chloro-2-{1-[2-(4-dimethylamino-phenyl)-4,4-dimethyl-4,5-dihydro-imidazol-1-yl]-2-methyl-propyl}-3H-quinazolin-4-one;

3-Benzyl-7-chloro-2-{-[2-(4-isopropyl-phenyl)-4,4-dimethyl-4,5-dihydro-imidazol-1-yl]-2-methyl-propyl}-3H-quinazolin-4-one;

3-Benzyl-7-chloro-2-{1-[2-(3-chloro-4-methyl-phenyl)-4,4-dimethyl-4,5-dihydro-imidazol-1-yl]-2-methyl-propyl}-3H-quinazolin-4-one;

3-Benzyl-2-{1-[2-(3-bromo-4-methyl-phenyl)-4,4-dimethyl-4,5-dihydro-imidazol-1-yl]-2-methyl-propyl}-3H-quinazolin-4-one;

4-{1-[1-(3-Benzyl-7-chloro-4-oxo-3,4-dihydro-quinazolin-2-yl)-2-methyl-propyl]-4,4-dimethyl-4,5-dihydro-1H-imidazol-2-yl}-benzonitrile;

3-Benzyl-7-chloro-2-[1-(4,4-dimethyl-2-(2-tolyl)-4,5-dihydro-imidazol-1-yl)-2-methyl-propyl]-3H-quinazolin-4-one;

3-Benzyl-7-chloro-2-[1-(4,4-dimethyl-2-pyridin-3-yl-4,5-dihydro-imidazol-1-yl)-2-methyl-propyl]-3H-quinazolin-4-one;

3-Benzyl-7-chloro-2-[1-(4,4-dimethyl-2-pyridin-4-yl-4,5-dihydro-imidazol-1-yl)-2-methyl-propyl]-3H-quinazolin-4-one;

3-Benzyl-7-chloro-2-{1-[2-(3-fluoro-4-methyl-phenyl)-4,5-dihydro-imidazol-1-yl]-2-methyl-propyl}-3H-quinazolin-4-one;

3-Benzyl-2-{1-[2-(4-bromo-phenyl)-4,5-dihydro-imidazol-1-yl]-2-methyl-propyl}-7-chloro-3H-quinazolin-4-one;

3-Benzyl-7-chloro-2-{1-[(S)-2-(3-fluoro-4-methyl-phenyl)-4-methyl-4,5-dihydro-imidazol-1-yl]-2-methyl-propyl}-3H-quinazolin-4-one;

3-Benzyl-7-chloro-2-[2-methyl-1-((S)-4-methyl-2-p-tolyl-4,5-dihydro-imidazol-1-yl)-propyl]-3H-quinazolin-4-one;

3-Benzyl-7-chloro-2-{1-[2-(2-methoxy-ethyl)-4,4-dimethyl-4,5-dihydro-imidazol-1-yl]-2-methyl-propyl}-3H-quinazolin-4-one;

3-Benzyl-7-chloro-2-[1-(2-isopropyl-4,4-dimethyl-4,5-dihydro-imidazol-1-yl)-2-methyl-propyl]-3H-quinazolin-4-one;

3-Benzyl-7-chloro-2-[1-(4,4-dimethyl-2-quinoxalin-2-yl-4,5-dihydro-imidazol-1-yl)-2-methyl-propyl]-3H-quinazolin-4-one;

3-Benzyl-7-chloro-2-{1-[2-(4-ethyl-phenyl)-4,4-dimethyl-4,5-dihydro-imidazol-1-yl]-2-methyl-propyl}-3H-quinazolin-4-one;

3-Benzyl-7-chloro-2-[(R)-2-methyl-1-(2-p-tolyl-4,5-dihydro-imidazol-1-yl)-propyl]-3H-quinazolin-4-one;

N-(4-{1-[1-(3-Benzyl-7-chloro-4-oxo-3,4-dihydro-quinazolin-2-yl)-2-methyl-propyl]-4,4-dimethyl-4,5-dihydro-1H-imidazol-2-yl}-phenyl)-acetamide;

3-Benzyl-7-chloro-2-{1-[2-(3-fluoro-4-methyl-phenyl)-4,5-dihydro-imidazol-1-yl]-2-methyl-propyl}-3H-quinazolin-4-one;

3-Benzyl-2-{1-[2-(4-bromo-phenyl)-4,5-dihydro-imidazol-1-yl]-2-methyl-propyl}-7-chloro-3H-quinazolin-4-one;

3-Benzyl-7-chloro-2-{(R)-1-[2-(3-fluoro-4-methyl-phenyl)-4,5-dihydro-imidazol-1-yl]-2-methyl-propyl}-3H-quinazolin-4-one;

3-Benzyl-7-chloro-2-[2-methyl-1-(2-phenyl-imidazol-1-yl)-propyl]-3H-quinazolin-4-one 3-Benzyl-7-chloro-2-[2-methyl-1-(2-p-tolyl-imidazol-1-yl)-propyl]-3H-quinazolin-4-one;

3-Benzyl-7-chloro-2-{1-[2-(4-fluoro-phenyl)-imidazol-1-yl]-2-methyl-propyl}-3H-quinazolin-4-one;

4-{1-[1-(3-Benzyl-7-chloro-4-oxo-3,4-dihydro-quinazolin-2-yl)-2-methyl-propyl]-1H-imidazol-2-yl}-benzonitrile;

3-Benzyl-7-chloro-2-{1-[2-(4-chloro-phenyl)-imidazol-1-yl]-2-methyl-propyl}-3H-quinazolin-4-one;

3-Benzyl-7-chloro-2-{1-[2-(3-fluoro-4-methyl-phenyl)-imidazol-1-yl]-2-methyl-propyl}-3H-quinazolin-4-one;

2-{1-[4-(2-Amino-ethyl)-2-p-tolyl-imidazol-1-yl]-2-methyl-propyl}-3-benzyl-7-chloro-3H-quinazolin-4-one;

3-Benzyl-7-chloro-2-{1-[2-(3-fluoro-4-methyl-phenyl)-4,4-dimethyl-4,5-dihydro-imidazol-1-yl]-2-methyl-propyl}-3H-quinazolin-4-one;

3-Benzyl-7-chloro-2-{1-[2-(methoxymethyl)-imidazol-1-yl]-2-methyl-propyl}-3H-quinazolin-4-one;

2-(2-{1-[1-(3-Benzyl-7-chloro-4-oxo-3,4-dihydro-quinazolin-2-yl)-2-methyl-propyl]-2-p-tolyl-1H-imidazol-4-yl}-ethyl)-isoindole-1,3-dione;

2-{1-[4-(2-Amino-ethyl)-2-p-tolyl-imidazol-1-yl]-2-methyl-propyl}-3-benzyl-7-chloro-3H-quinazolin-4-one;

(2-{1-[1-(3-Benzyl-7-chloro-4-oxo-3,4-dihydro-quinazolin-2-yl)-2-methyl-propyl]-2-p-tolyl-1H-imidazol-4-yl}-ethylamino)-acetic acid tert-butyl ester;

(2-{1-[1-(3-Benzyl-7-chloro-4-oxo-3,4-dihydro-quinazolin-2-yl)-2-methyl -propyl]-2-p-tolyl-1H-imidazol-4-yl}-ethylamino)-acetic acid;

2-{1-[4-(3-Amino-propyl)-2-p-tolyl-imidazol-1-yl]-2-methyl-propyl}-3-benzyl-7-chloro-3H-quinazolin-4-one;

3-Benzyl-7-chloro-2-(1-imidazol-1-yl-2-methyl-propyl)-3H-quinazolin-4-one;

2-[(R)-1-(4-Aminomethyl-2-p-tolyl-imidazol-1-yl)-2-methyl-propyl]-3-benzyl-7-chloro-3H-quinazolin-4-one;

2-{(R)-1-[4-Aminomethyl-2-(3-fluoro-4-methyl-benzoyl)-imidazol-1-yl]-2-methyl-propyl}-3-benzyl-7-chloro-3H-quinazolin-4-one;

N-{1-[(R)-1-(3-Benzyl-7-chloro-4-oxo-3,4-dihydro-quinazolin-2-yl)-2-methyl -propyl]-2-p-tolyl-1H-imidazol-4-ylmethyl}-acetamide;

2-{(R)-1-[4-(N,N-Dicarboxymethyl)aminomethyl-2-p-tolyl-imidazol-1-yl]-2-methyl-propyl }-3-benzyl-7-chloro-3H-quinazolin-4-one;

2-{(R)-1-[4-(N-Carboxymethyl)aminomethyl-2-p-tolyl-imidazol-1-yl]-2-methyl-propyl }-3-benzyl-7-chloro-3H-quinazolin-4-one;

3-Benzyl-7-chloro-2-[(R)-1-(4-hydroxymethyl-2-p-tolyl-imidazol-1-yl)-2-methyl-propyl ]-3H-quinazolin-4-one;

(3-{(S)-1-[(R)-1-(3-Benzyl-7-chloro-4-oxo-3,4-dihydro-quinazolin-2-yl)-2-methyl-propyl]-2-p-tolyl-4,5-dihydro-1H-imidazol-4-yl}-propyl)-carbamic acid benzyl ester; and 2-{(R)-1-[(S)-4-(3-Amino-propyl)-2-p-tolyl-4,5-dihydro-imidazol-1-yl]-2-methyl-propyl}-3-benzyl-chloro-3H-quinazolin-4-one.

Utility, Testing and Administration

General Utility

Once made, the compounds of the invention find use in a variety of applications involving alteration of mitosis. As will be appreciated by those skilled in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In a particular embodiment, the compounds of the invention are used to inhibit mitotic spindle formation, thus causing prolonged cell cycle arrest in mitosis. By "inhibit" in this context is meant decreasing or interfering with mitotic spindle formation or causing mitotic spindle dysfunction. By "mitotic spindle formation" herein is meant organization of microtubules into bipolar structures by mitotic kinesins. By "mitotic spindle dysfunction" herein is meant mitotic arrest and monopolar spindle formation.

The compounds of the invention are useful to bind to, and/or inhibit the activity of, a mitotic kinesin, KSP. In one embodiment, the KSP is human KSP, although the compounds may be used to bind to or inhibit the activity of KSP kinesins from other organisms. In this context, "inhibit" means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. See U.S. Pat. No. 6,437,115, hereby incorporated by reference in its entirety. The compounds of the invention have been shown to have specificity for KSP. However, the present invention includes the use of the compounds to bind to or modulate other mitotic kinesins.

The compounds of the invention are used to treat cellular proliferation diseases. Such disease states which can be treated by the compounds, compositions and methods provided herein include, but are not limited to, cancer (further discussed below), autoimmune disease, fungal disorders, arthritis, graft rejection, inflammatory bowel disease, cellular proliferation induced after medical procedures, including, but not limited to, surgery, angioplasty, and the like. Treatment includes inhibiting cellular proliferation. It is appreciated that in some cases the cells may not be in an abnormal state and still require treatment. Thus, in one embodiment, the invention herein includes application to cells or individuals afflicted or subject to impending affliction with any one of these disorders or states.

The compounds, compositions and methods provided herein are particularly deemed useful for the treatment of cancer including solid tumors such as skin, breast, brain, cervical carcinomas, testicular carcinomas, etc. More particularly, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformanis), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kalposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

Testing

For assay of KSP-modulating activity, generally either KSP or a compound according to the invention is non-diffusably bound to an insoluble support having isolated sample receiving areas (e.g., a microtiter plate, an array, etc.). The insoluble support may be made of any composition to which the sample can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the sample is not crucial so long as it is compatible with the reagents and overall methods of the invention, maintains the activity of the sample and is nondiffusable. Particular methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the sample, excess unbound material is removed by washing. The sample receiving areas may then be blocked through incubation with bovine serum albumin (BSA), casein or other innocuous protein or other moiety.

The compounds of the invention may be used on their own to inhibit the activity of a mitotic kinesin, particularly KSP. In one embodiment, a compound of the invention is combined with KSP and the activity of KSP is assayed. Kinesin (including KSP) activity is known in the art and includes one or more kinesin activities. Kinesin activities include the ability to affect ATP hydrolysis; microtubule binding; gliding and polymerization/depolymerization (effects on microtubule dynamics); binding to other proteins of the spindle; binding to proteins involved in cell-cycle control; serving as a substrate to other enzymes, such as kinases or proteases; and specific kinesin cellular activities such as spindle pole separation.

Methods of performing motility assays are well known to those of skill in the art. (See e.g., Hall, et al. (1996), Biophys. J., 71: 3467-3476, Turner et al., 1996, Anal. Biochem. 242 (1):20-5; Gittes et al., 1996, Biophys. J. 70(1): 418-29; Shirakawa et al., 1995, J. Exp. BioL 198: 1809-15; Winkelmann et al., 1995, Biophys. J. 68: 2444-53; Winkelmann et al., 1995, Biophys. J. 68: 72S.)

Methods known in the art for determining ATPase hydrolysis activity also can be used. Suitably, solution based assays are utilized. U.S. Pat. No. 6,410,254, hereby incorporated by reference in its entirety, describes such assays. Alternatively, conventional methods are used. For example, $P_i$ release from kinesin can be quantified. In one embodiment, the ATPase hydrolysis activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 µL of the reaction mixture is quenched in 90 µL of cold 0.3 M PCA. Phosphate standards are used so data can be converted to mM inorganic phosphate released. When all reactions and standards have been quenched in PCA, 100 µL of malachite green reagent is added to the relevant wells in e.g., a microtiter plate. The mixture is developed for 10-15 minutes and the plate is read at an absorbance of 650 nm. If phosphate standards were used, absorbance readings can be converted to mM $P_i$ and plotted over time. Additionally, ATPase assays known in the art include the luciferase assay.

ATPase activity of kinesin motor domains also can be used to monitor the effects of agents and are well known to those skilled in the art. In one embodiment ATPase assays of kinesin are performed in the absence of microtubules. In another embodiment, the ATPase assays are performed in the presence of microtubules. Different types of agents can be detected in the above assays. In a one embodiment, the effect of an agent is independent of the concentration of microtubules and ATP. In another embodiment, the effect of the agents on kinesin ATPase can be decreased by increasing the concentrations of ATP, microtubules or both. In yet another embodiment, the effect of the agent is increased by increasing concentrations of ATP, microtubules or both.

Compounds that inhibit the biochemical activity of KSP in vitro may then be screened in vivo. In vivo screening methods include assays of cell cycle distribution, cell viability, or the presence, morphology, activity, distribution, or number of mitotic spindles. Methods for monitoring cell cycle distribution of a cell population, for example, by flow cytometry, are well known to those skilled in the art, as are methods for determining cell viability. See for example, U.S. Pat. No. 6,437,115, hereby incorporated by reference in its entirety. Microscopic methods for monitoring spindle formation and malformation are well known to those of skill in the art (see, e.g., Whitehead and Rattner (1998), J. Cell Sci. 111:2551-61; Galgio et. al, (1996) J. Cell Biol., 135:399-414), each incorporated herein by reference in its entirety.

The compounds of the invention inhibit the KSP kinesin. One measure of inhibition is $IC_{50}$, defined as the concentration of the compound at which the activity of KSP is decreased by fifty percent relative to a control. Preferred compounds have $IC_{50}$'s of less than about 1 mM, with preferred embodiments having $IC_{50}$'s of less than about 100 µM, with more preferred embodiments having $IC_{50}$'s of less than about 10 µM, with particularly preferred embodiments having $IC_{50}$'s of less than about 1 µM, and especially preferred embodiments having $IC_{50}$'s of less than about 100 nM, and with the most preferred embodiments having $IC_{50}$'s of less than about 10 nM. Measurement of $IC_{50}$ is done using an ATPase assay such as described herein.

Another measure of inhibition is $K_i$. For compounds with $IC_{50}$'s less than 1 µM, the $K_i$ or $K_d$ is defined as the dissociation rate constant for the interaction of the compounds described herein with KSP. Preferred compounds have $K_i$'s of less than about 100 µM, with preferred embodiments having $K_i$'s of less than about 10 µM, and particularly preferred embodiments having $K_i$'s of less than about 1 µM and especially preferred embodiments having $K_i$'s of less than about 100 nM, and with the most preferred embodiments having $K_i$'s of less than about 10 nM.

The $K_i$ for a compound is determined from the $IC_{50}$ based on three assumptions and the Michaelis-Menten equation. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + Kd) - \sqrt{(E_0 + I_0 + Kd)^2 - 4E_0I_0}}{2E_0}\right]$$

where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Preferred compounds have $GI_{50}$'s of less than about 1 mM; those having a $GI_{50}$ of less than about 20 µM are more preferred; those having a $GI_{50}$ of less than about 10 µM more so; those having a $GI_{50}$ of less than about 1 µM more so; those having a $GI_{50}$ of less than about 100 nM more so; and those having a $GI_{50}$ of less than about 10 nM even more so. Measurement of $GI_{50}$ is done using a cell proliferation assay such as described herein. Compounds of this class were found to inhibit cell proliferation.

In vitro potency of small molecule inhibitors is determined, for example, by assaying human ovarian cancer cells (SKOV3) for viability following a 72-hour exposure to a 9-point dilution series of compound. Cell viability is determined by measuring the absorbance of formazon, a product formed by the bioreduction of MTS/PMS, a commercially available reagent. Each point on the dose-response curve is calculated as a percent of untreated control cells at 72 hours minus background absorption (complete cell kill).

Anti-proliferative compounds that have been successfully applied in the clinic to treatment of cancer (cancer chemotherapeutics) have $GI_{50}$'s that vary greatly. For example, in A549 cells, paclitaxel $GI_{50}$ is 4 nM, doxorubicin is 63 nM, 5-fluorouracil is 1 µM, and hydroxyurea is 500 µM (data provided by National Cancer Institute, Developmental Therapeutic Program, http://dtp.nci.nih.gov/). Therefore, compounds that inhibit cellular proliferation, irrespective of the concentration demonstrating inhibition, have potential clinical usefulness.

To employ the compounds of the invention in a method of screening for compounds that bind to KSP kinesin, the KSP is bound to a support, and a compound of the invention is added to the assay. Alternatively, the compound of the invention is bound to the support and KSP is added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays; immunoassays for protein binding, functional assays (phosphorylation assays, etc.) and the like.

The determination of the binding of the compound of the invention to KSP may be done in a number of ways. In one embodiment, the compound is labeled, for example, with a fluorescent or radioactive moiety, and binding is determined directly. For example, this may be done by attaching all or a portion of KSP to a solid support, adding a labeled test compound (for example a compound of the invention in which at least one atom has been replaced by a detectable isotope), washing off excess reagent, and determining whether the amount of the label is that present on the solid support.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}$I, or with fluorophores. Alternatively, more than one component may be labeled with different labels; using $^{125}$I for the proteins, for example, and a fluorophor for the antimitotic agents.

The compounds of the invention may also be used as competitors to screen for additional drug candidates. "Candidate agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, particular embodiments exclude molecules already known to bind to that particular protein, for example, polymer structures such as microtubules, and energy sources such as ATP. Particular embodiments of assays herein include candidate agents which do not bind the cellular proliferation protein in its endogenous native state termed herein as "exogenous" agents. In another embodiment, exogenous agents further exclude antibodies to KSP.

Candidate agents can encompass numerous chemical classes, though typically they are small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl-, hydroxyl-, ether, or carboxyl group, often at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, and/or amidification to produce structural analogs.

Competitive screening assays may be done by combining KSP and a drug candidate in a first sample. A second sample comprises a compound of the present invention, KSP and a drug candidate. This may be performed in either the presence or absence of microtubules. The binding of the drug candidate is determined for both samples, and a change, or difference in binding between the two samples indicates the presence of a drug candidate capable of binding to KSP and potentially inhibiting its activity. That is, if the binding of the drug candidate is different in the second sample relative to the first sample, the drug candidate is capable of binding to KSP.

In a particular embodiment, the binding of the candidate agent to KSP is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present. Incubations may be performed at any temperature which facilitates optimal activity, typically between 4 and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In another embodiment, the competitor is added first, followed by the candidate agent. Displacement of the competitor is an indication the candidate agent is binding to KSP and thus is capable of binding to, and potentially inhibiting, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

Inhibition is tested by screening for candidate agents capable of inhibiting the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein. The methods include both in vitro screening methods and in vivo screening of cells for alterations in cell cycle distribution, cell viability, or for the presence, morpohology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Suitably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Administration

Accordingly, the compounds of the invention are administered to cells. By "administered" herein is meant administration of a therapeutically effective dose of a compound of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant any cell in which mitosis or meiosis can be altered.

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

Compounds of the invention having the desired pharmacological activity may be administered, preferably as a pharmaceutically acceptable composition comprising an pharmaceutical excipient, to a patient, as described herein. Depending upon the manner of introduction, the compounds may be formulated in a variety of ways as discussed below. The concentration of therapeutically active compound in the formulation may vary from about 0.1-100 wt. %.

The agents may be administered alone or in combination with other treatments, i.e., radiation, or other chemotherapeutic agents such as the taxane class of agents that appear to act on microtubule formation or the camptothecin class of topoisomerase I inhibitors. When used, other chemotherapeutic agents may be administered before, concurrently, or after administration of a compound of the present invention. In one aspect of the invention, a compound of the present invention is co-administered with one or more other chemotherapeutic agents. By "co-administer" it is meant that the present compounds are administered to a patient such that the present compounds as well as the co-administered compound may be found in the patient's bloodstream at the same time, regardless when the compounds are actually administered, including simultaneously.

The administration of the compounds and compositions of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the compound or composition may be directly applied as a solution or spray.

Pharmaceutical dosage forms include a compound of Formula Ia or Ib or a pharmaceutically acceptable salt, solvate, or solvate of a salt thereof, and one or more pharmaceutical excipients. As is known in the art, pharmaceutical excipients are secondary ingredients which function to enable or enhance the delivery of a drug or medicine in a variety of dosage forms (e.g.: oral forms such as tablets, capsules, and liquids; topical forms such as dermal, opthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (I 995), each of which is incorporated herein by reference for all purposes.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colors, flavors, sweetening agents, polymers, waxes or other solubility-retarding materials.

Compositions for intravenous administration will generally comprise intravenous fluids, i.e., sterile solutions of simple chemicals such as sugars, amino acids or electrolytes, which can be easily carried by the circulatory system and assimilated. Such fluids are prepared with water for injection USP.

Fluids used commonly for intravenous (IV) use are disclosed in Remington, the Science and Practice of Pharmacy [full citation previously provided], and include:

alcohol (e.g., in dextrose and water ("D/W") [e.g., 5% dextrose] or dextrose and water [e.g., 5% dextrose] in normal saline solution ("NSS"); e.g. 5% alcohol):

synthetic amino acid such as Aminosyn, FreAmine, Travasol, e.g., 3.5 or 7; 8.5; 3.5, 5.5 or 8.5% respectively;
ammonium chloride e.g., 2.14%;
dextran 40, in NSS e.g., 10% or in D5/W e.g., 10%;
dextran 70, in NSS e.g., 6% or in D5/W e.g., 6%;
dextrose (glucose, D5/W) e.g., 2.5-50%;
dextrose and sodium chloride e.g., 5-20% dextrose and 0.22-0.9% NaCl;
lactated Ringer's (Hartmann's) e.g., NaCl 0.6%, KCl 0.03%, $CaCl_2$ 0.02%;
lactate 0.3%;
mannitol e.g., 5%, optionally in combination with dextrose e.g., 10% or NaCl e.g., 15 or 20%;
multiple electrolyte solutions with varying combinations of electrolytes, dextrose, fructose, invert sugar Ringer's e.g., NaCl 0.86%, KCl 0.03%, $CaCl_2$ 0.033%;
sodium bicarbonate e.g., 5%;
sodium chloride e.g., 0.45, 0.9, 3, or 5%;
sodium lactate e.g., ⅙ M; and
sterile water for injection The pH of such fluids may vary, and will typically be from 3.5 to 8 such as known in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All publications, including but not limited to patents and patent applications, cited in this specification are herein incorporated by reference as if each individual publication were specifically and individually indicated to be incorporated by reference herein as though fully set forth.

EXAMPLES

All anhydrous solvents were purchased from Aldrich Chemical Company in SureSeal® containers Example 1

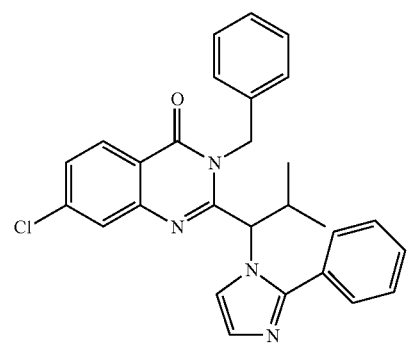

3-Benzyl-7-chloro-2-[2-methyl-1-(2-phenyl-imidazol-1-yl)-propyl]-3H-quinazolin-4-one a) 3-Benzyl-7-chloro-2-[1-(2,2-dimethoxy-ethylamino)-2-methyl-propyl]-3H-quinazolin-4-one To a solution of 2-(1-amino-2-methyl-propyl)-3-benzyl-7-chloro-3H-quinazolin-4-one (1.87 g, 5.48 mmol) in DMF (30 mL) was added bromoacetaldehyde dimethylacetal (2.78 g, 16.44 mmol) and potassium carbonate (2.27 g, 16.44 mmol) and the resulting suspension was heated at 135° C. for 18 h. The cooled reaction was concentrated in vacuo, triturated with methylene chloride to remove any solids, and the filtrate was concentrated in vacuo. The residue was purified by flash chromatography (silica gel; 2:1 hexanes:ethyl acetate) to give the title compound as a pale yellow oil (1.38 g, 59%). MS(ES+) m/e 430 [M+H]+.

b) N-[1-(3-Benzyl-7-chloro-4-oxo-3,4-dihydro-quinazolin-2-yl)-2-methyl-propyl]-N-(2,2-dimethoxy-ethyl)-benzamide A solution of 3-benzyl-7-chloro-2-[1-(2,2-dimethoxy-ethylamino)-2-methyl-propyl]-3H-quinazolin-4-one (505 mg, 1.17 mmol), benzoyl chloride (247 mg, 1.76 mmol), and triethylamine (179 mg, 1.76 mmol) in methylene chloride (10 mL) was stirred at room temperature for 18 h. The reaction was washed sequentially with 0.5 N HCl, water. 5% NaHCO3, water, and brine. The organic layer was dried (Na2SO4) and concentrated to yield the title compound as an orange oil (338 mg, 54%). MS(ES+) m/e 534 [M+H]+.

c) 3-Benzyl-7-chloro-2-[2-methyl-1-(2-phenyl-imidazol-1-yl)-propyl]-3H-quinazolin-4-one A solution of N-[1-(3-benzyl-7-chloro-4-oxo-3,4-dihydro-quinazolin-2-yl)-2-methyl-propyl]-N-(2,2-dimethoxy-ethyl)-benzamide (288 mg, 0.539 mmol) and ammonium acetate (374 mg, 4.85 mmol) in acetic acid (4.0 mL) was refluxed for 2.0 h. The reaction was concentrated in vacuo and the residue was dissolved in ethyl acetate and washed sequentially with saturated sodium carbonate, water, and brine. The organic layer was dried (Na2SO4), concentrated in vacuo, and recrystallized from ethanol to give the title compound as tan crystals (57.1 mg, 23%). MS(ES+) m/e 469 [M+H]+.

Example 2

3-Benzyl-7-chloro-2-[2-methyl-1-(2-p-tolyl-imidazol-1-yl)-propyl]-3H-quinazolin-4-one

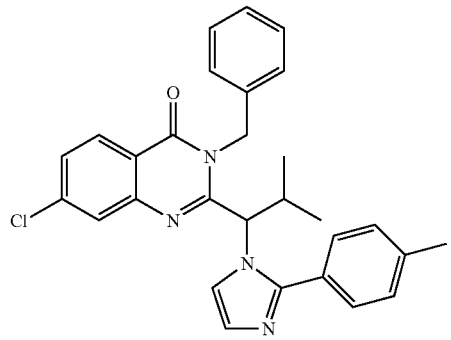

The title compound was prepared as in example one, except substituting p-toluoyl chloride for benzoyl chloride, as a white crystalline solid (22%). MS(ES+) m/e 483 [M+H]+.

Example 3

3-Benzyl-7-chloro-2-{1-[2-(4-fluoro-phenyl)-imidazol-1-yl]-2-methyl-propyl}-3H-quinazolin-4-one

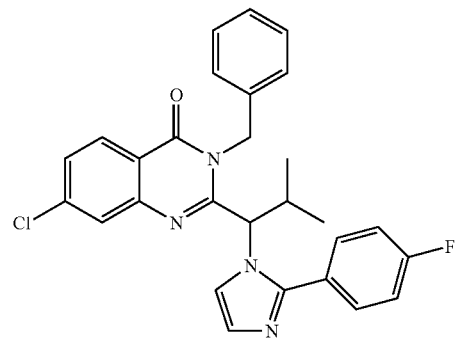

The title compound was prepared as in example one, except substituting 4-fluorobenzoyl chloride for benzoyl chloride, as tan crystals (17%). MS(ES+) m/e 487 [M+H].

Example 4

4-{1-[1-(3-Benzyl-7-chloro-4-oxo-3,4-dihydro-quinazolin-2-yl)-2-methyl-propyl]-1H-imidazol-2-yl}-benzonitrile

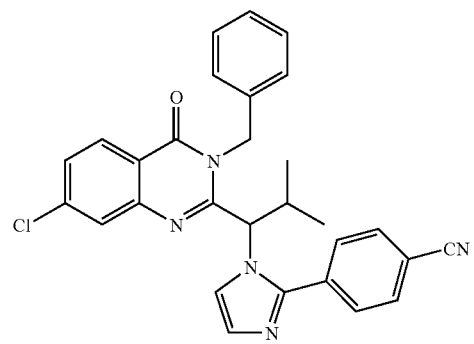

The title compound was prepared as in example one, except substituting 4-cyanobenzoyl chloride for benzoyl chloride and pyridine for methylene chloride, as tan crystals (18%). MS(ES+) n/e 494 [M+H]+.

Example 5

3-Benzyl-7-chloro-2-{1-[2-(4-chloro-phenyl)-imidazol-1-yl]-2-methyl-propyl}-3H-quinazolin-4-one

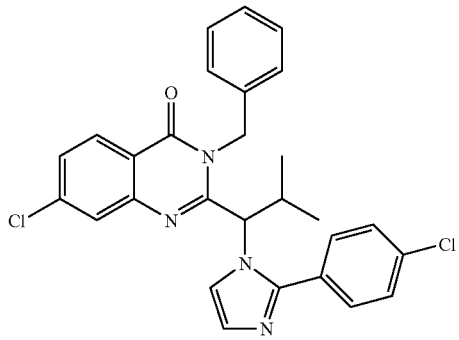

The title compound was prepared as in example one, except substituting 4-chlorobenzoyl chloride for benzoyl chloride, as a white solid (24%). MS(ES+) m/e 503 [M+H]+.

Example 6

3-Benzyl-7-chloro-2-{1-[2-(3-fluoro-4-methyl-phenyl)-imidazol-1-yl]-2-methyl-propyl}-3H-quinazolin-4-one

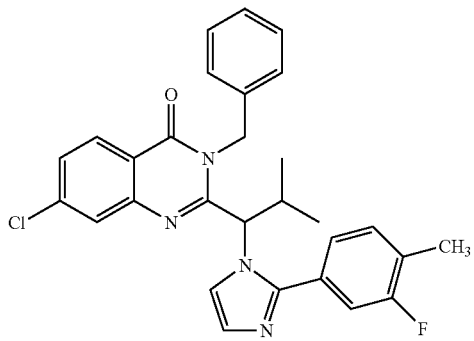

The title compound was prepared as in example one, except substituting 3-fluoro-4-methylbenzoyl chloride for benzoyl chloride, as tan crystals (26%). MS(ES+) m/e 501 [M+H]+.

Example 7

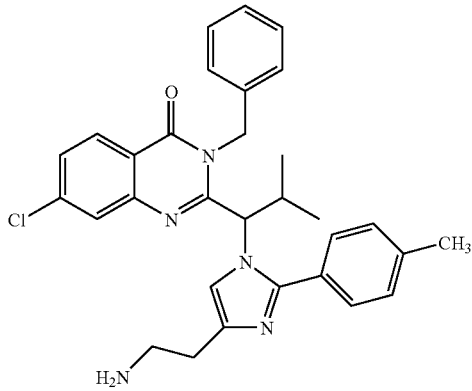

2-{1-[4-(2-Amino-ethyl)-2-p-tolyl-imidazol-1-yl]-2-methyl-propyl}-3-benzyl-7-chloro-3H-quinazolin-4-one a) 2-{4-[1-(3-Benzyl-7-chloro-4-oxo-3,4-dihydro-quinazolin-2-yl)-2-methyl-propylamino]-3-oxo-butyl}-isoindole-1,3-dione A suspension of 2-(1-amino-2-methyl-propyl)-3-benzyl-7-chloro-3H-quinazolin-4-one (1.0 g, 2.93 mmol), 2-(4-bromo-3-oxo-butyl)-isoindole-1,3-dione (867 mg., 2.93 mmol, prepared as described in WO 89/10360), and potassium carbonate (405 mg, 2.93 mmol) in DMF (14 mL) was stirred at room temperature for 80 minutes. The reaction was diluted with water and the resulting white solid (1.6 g.) was used in the subsequent step without further purification.

b) N-[1-(3-Benzyl-7-chloro-4-oxo-3,4-dihydro-quinazolin-2-yl)-2-methyl-propyl]-N-[4-(1,3-dioxo-1,3-dihydro-isoindol-2-yl)-2-oxo-butyl]-4-methyl-benzamide A solution of 2-{4-[1-(3-benzyl-7-chloro-4-oxo-3,4-dihydro-quinazolin-2-yl)-2-methyl-propylamino]-3-oxo-butyl}-isoindole-1,3-dione (1.5 g from previous step), triethylamine (245 mg, 2.42 mmol), and p-toluoyl chloride (374 mg, 2,42 mmol) in methylene chloride (10 mL) was stirred at room temperature for 2.0 h. The reaction was washed sequentially with 0.5 N HCl, water, 5% NaHCO₃, water, and brine and dried (Na₂SO₄). The filtrate was concentrated in vacuo and purified by flash chromatography (silica gel 3:2 hexanes: EtOAc as eluent) to provide the title compound as a white solid (0.7 g, 35%, 2 steps). MS(ES+) m/e 675 [M+H]+.

c) 2-(2-{1-[1-(3-Benzyl-7-chloro-4-oxo-3,4-dihydro-quinazolin-2-yl)-2-methyl-propyl]-2-p-tolyl-1H-imidazol-4-yl}-ethyl)-isoindole-1,3-dione A solution of N-[1-(3-benzyl-7-chloro-4-oxo-3,4-dihydro-quinazolin-2-yl)-2-methyl-propyl]-N-[4-(1,3-dioxo-1,3-dihydro-isoindol-2-yl)-2-oxo-butyl]-4-methyl-benzamide (641 mg, 0.948 mmol) and ammonium acetate (3.65 g, 47.4 mmol) in acetic acid (30 mL) was refluxed for 6.0 h using a Dean-Stark trap and condenser. The reaction was concentrated in vacuo and the residue was triturated with water, dried in a Buchner funnel, and recrystallized from ethanol to provide the title compound as a white solid (320 mg, 51%). MS(ES+) m/e 656 [M+H]+.

d) 2-{1-[4-(2-Amino-ethyl)-2-p-tolyl-imidazol-1-yl]-2-methyl-propyl}-3-benzyl-7-chloro-3H-quinazolin-4-one A solution of 2-(2-{1-[1-(3-benzyl-7-chloro-4-oxo-3,4-dihydro-quinazolin-2-yl)-2-methyl-propyl]-2-p-tolyl-1H-imidazol-4-yl}-ethyl)-isoindole-1,3-dione (278 mg, 0.423 mmol) and anhydrous hydrazine (98 mg, 3.06 mmol) in EtOH (12 mL) was refluxed for 3.0 h. The reaction was cooled to 5° C. and a white precipitate was filtered off. The filtrate was concentrated in vacuo and purified by flash chromatography (silica gel, 90:9:1 methylene chloride:methanol:ammonium hydroxide as eluent) to provide the title compound as a white solid (98.2 mg, 45%). MS(ES+) m/e 526 [M+H]+.

Example 8

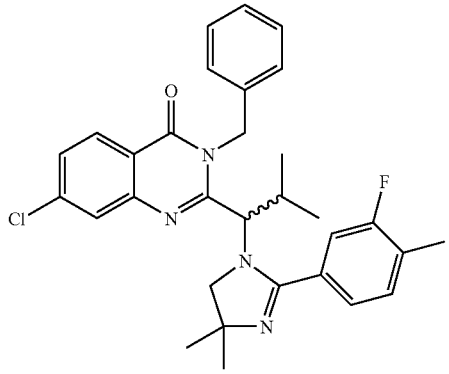

(±)-3-Benzyl-7-chloro-2-{1-[2-(3-fluoro-4-methyl-phenyl)-4,4-dimethyl-4,5-dihydro-imidazol-1-yl]-2-methyl-propyl}-3H-quinazolin-4-one a) (±)-{2-[1-(3-Benzyl-7-chloro-4-oxo-3,4-dihydro-quinazolin-2-yl)-2-methyl-propylamino]-1,1-dimethyl-ethyl}-carbamic acid tert-butyl ester To a solution of 2-(1-amino-2-methyl-propyl)-3-benzyl-7-chloro-3H-quinazolin-4-one (WO 0130768) (1.09 g, 3.19 mmol) and (1,1-dimethyl-2-oxo-ethyl)-carbamic acid tert-butyl ester (Seki et. al. Chem. Pharm. Bull. 1996, 44, 2061) (0.59 g, 3.19 mmol) in dichloromethane (80 mL) was added sodium triacetoxyborohydride (1.01 g, 4.79 mmol). The resultant cloudy mixture was maintained at ambient temperature for 4 hours, at which time it was quenched with brine (75 mL) and stirred vigorously for 10 minutes. The aqueous layer was extracted with dichloromethane (50 mL) and the combined extracts were dried over magnesium sulfate, filtered and concentrated under reduced pressure to give (±)-{2-[1-(3-benzyl-7-chloro-4-oxo-3,4-dihydro-quinazolin-2-yl)-2-methyl-propylamino]-1,1-dimethyl-ethyl}-carbamic acid tert-butyl ester (1.62 g, 99%) as a yellow solid which was used in the subsequent step without purification.

b) (±)-2-[1-(2-Amino-2-methyl-propylamino)-2-methyl-propyl]-3-benzyl-7-chloro-3H-quinazolin-4-one To a solution of (±)-{2-[1-(3-benzyl-7-chloro-4-oxo-3,4-dihydro-quinazolin-2-yl)-2-methyl-propylamino]-1,1-dimethyl-ethyl}-carbamic acid tert-butyl ester (1.62 g, 3.16 mmol) in dichloromethane (40 mL) was added trifluoroacetic acid (10 mL). The resultant solution was maintained at ambient temperature overnight and concentrated under reduced pressure. The residue was dissolved in dichloromethane (50 mL) and washed with saturated aqueous sodium bicarbonate (40 mL). The aqueous layer was extracted with dichloromethane (50 mL) and the combined extracts were dried over magnesium sulfate, filtered and concentrated under reduced pressure to give (±)-2-[1-(2-amino-2-methyl-propylamino)-2-methyl-propyl]-3-benzyl-7-chloro-3H-quinazolin-4-one (1.29 g, 99%) as a yellow solid which was used in the subsequent step without purification.

Method A:

c) (±)-N-{2-[1-(3-Benzyl-7-chloro-4-oxo-3,4-dihydro-quinazolin-2-yl)-2-methyl-propylamino]-1,1-dimethyl-ethyl}-3-fluoro-4-methyl-benzamide To a solution of (±)-2-[1-(2-amino-2-methyl-propylamino)-2-methyl-propyl]-3-benzyl-7-chloro-3H-quinazolin-4-one (133 mg, 0.32 mmol) in dichloromethane (3 mL) was added triethylamine (90 μL, 0.64 mmol), followed by 3-fluoro-4-methylbenzoyl chloride (51 μL, 0.35 mmol). The resultant solution was stirred at ambient temperature for 3 hours, quenched with saturated aqueous sodium bicarbonate (5 mL) and diluted with dichloromethane (5 mL). The aqueous layer was extracted with dichloromethane (5 mL) and the combined extracts were dried over magnesium sulfate, filtered and concentrated under reduced pressure. The residue was purified by silica gel chromatography (10-20% ethyl acetate/hexanes) to give (±)-N-{2-[1-(3-benzyl-7-chloro-4-oxo-3,4-dihydro-quinazolin-2-yl)-2-methyl-propylamino]-1,1-dimethyl-ethyl}-3-fluoro-4-methyl-benzamide (120 mg, 68%) as a white solid.

d) (±)-3-Benzyl-7-chloro-2-{1-[2-(3-fluoro-4-methyl-phenyl)-4,4-dimethyl-4,5-dihydro-imidazo-1-yl]-2-methyl-propyl}-3H-quinazolin-4-one A solution of (±)-N-{2-[1-(3-benzyl-7-chloro-4-oxo-3,4-dihydro-quinazolin-2-yl)-2-methyl-propylamino]-1,1-dimethyl-ethyl}-3-fluoro-4-methyl-benzamide (120 mg, 0.219 mmol) in phosphorus oxychloride (2 mL) was heated at reflux. After 8 hours, the reaction mixture was allowed to cool to ambient temperature and concentrated under reduced pressure. The residue was dissolved in dichloromethane (10 mL) and washed with two 10 mL portions of saturated aqueous sodium bicarbonte. The combined aqueous layers were extracted with dichloromethane and the extracts were dried over magnesium sulfate, filtered and concentrated under reduced pressure. The residue was purified by silica gel chromatography (3% methanol/dichloromethane) to give (±)-3-benzyl-7-chloro-2-{1-[2-(3-fluoro-4-methyl-phenyl)-4,4- dimethyl-4,5-dihydro-imidazol-1-yl]-2-methyl-propyl}-3H-quinazolin-4-one (64 mg, 55%) as a white solid: LCMS 531 (M⁺+H)

Example 9

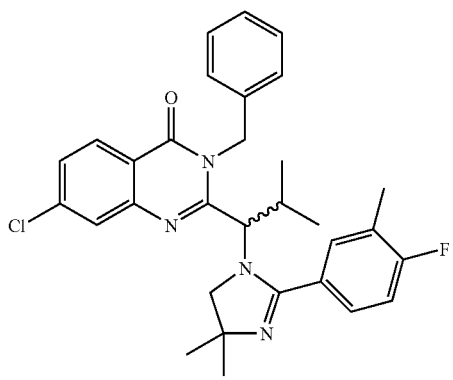

Method B:

a) (±)-3-Benzyl-7-chloro-2-{1-[2-(4-fluoro-3-methyl-phenyl)-4,4-dimethyl-4,5-dihydro-imidazol-1-yl]-2-methyl-propyl}-3H-quinazolin-4-one To a solution of (±)-2-[1-(2-amino-2-methyl-propylamino)-2-methyl-propyl]-3-benzyl-7-chloro-3H-quinazolin-4-one (250 mg, 0.61 mmol) in dichloromethane (10 mL) was added triethylamine (295 µL, 2.12 mmol), followed by 4-fluoro-3-methylbenzoyl chloride (105 mg, 0.61 mmol). The resultant solution was stirred at ambient temperature for 2 hours, then evaporated under reduced pressure to a crude white solid. The resultant solid was treated with glacial acetic acid (10 mL) then the resultant suspension was heated at reflux for 48 hours. The reaction was cooled to ambient temperature then evaporated under reduced pressure to a crude oil. The oil was quenched with saturated aqueous sodium bicarbonate (10 mL) and brine (5 mL). The aqueous layer was extracted with dichloromethane (2×5 mL) and the combined extracts were dried over magnesium sulfate, filtered and concentrated under reduced pressure. The residue was purified by silica gel chromatography (5-10% ethyl acetate/hexanes) to furnish (±)-3-benzyl-7-chloro-2-{1-[2-(4-fluoro-3-methyl-phenyl)-4,4-dimethyl-4,5-dihydro-imidazol-1-yl]-2-methyl-propyl}-3H-quinazolin-4-one (138 mg, 43%) as a white solid: LCMS 531 (M⁺+H)

Example 10

By following the procedure described above, the following compounds were prepared:

| Compound | Method | MS (ES+) m/e [M + H]⁺ |
|---|---|---|
| (±)-3-Benzyl-7-chloro-2-{1-[2-(4-chloro-phenyl)-4,4-dimethyl-4,5-dihydro-imidazol-1-yl]-2-methyl-propyl}-3H-quinazolin-4-one | A | 533 |
| (±)-3-Benzyl-2-{1-[2-(4-bromo-phenyl)-4,4-dimethyl-4,5-dihydro-imidazol-1-yl]-2-methyl-propyl}-7-chloro-3H-quinazolin-4-one | A | 577 |
| (±)-3-Benzyl-7-chloro-2-{1-[2-(4-methoxy-phenyl)-4,4-dimethyl-4,5-dihydro-imidazol-1-yl]-2-methyl-propyl}-3H-quinazolin-4-one | A | 529 |
| (±)-3-Benzyl-7-chloro-2-{1-[4,4-dimethyl-2-(4-trifluoromethyl-phenyl)-4,5-dihydro-imidazol-1-yl]-2-methyl-propyl}-3H-quinazolin-4-one | A | 567 |
| (±)-3-Benzyl-7-chloro-2-[1-(4,4-dimethyl-2-thiophen-2-yl-4,5-dihydro-imidazol-1-yl)-2-methyl-propyl]-3H-quinazolin-4-one | A | 505 |
| (±)-3-Benzyl-7-chloro-2-[1-(2-furan-2-yl-4,4-dimethyl-4,5-dihydro-imidazol-1-yl)-2-methyl-propyl]-3H-quinazolin-4-one | A | 489 |
| (±)-3-Benzyl-7-chloro-2-[1-(2-methoxymethyl-4,4-dimethyl-4,5-dihydro-imidazol-1-yl)-2-methyl-propyl]-3H-quinazolin-4-one | A | 467 |
| (±)-3-Benzyl-7-chloro-2-[1-(4,4-dimethyl-2-m-tolyl-4,5-dihydro-imidazol-1-yl)-2-methyl-propyl]-3H-quinazolin-4-one | A | 513 |
| (±)-3-Benzyl-7-chloro-2-{1-[2-(3-chloro-phenyl)-4,4-dimethyl-4,5-dihydro-imidazol-1-yl]-2-methyl-propyl}-3H-quinazolin-4-one | A | 533 |
| 3-Benzyl-7-chloro-2-[(R)-1-(4,4-dimethyl-2-p-tolyl-4,5-dihydro-imidazol-1-yl)-2-methyl-propyl]-3H-quinazolin-4-one | A | 513 |
| (±)-3-Benzyl-7-chloro-2-{1-[2-(4-fluoro-phenyl)-4,4-dimethyl-4,5-dihydro-imidazol-1-yl]-2-methyl-propyl}-3H-quinazolin-4-one | A | 517 |
| 3-Benzyl-7-chloro-2-[1-(4,4-dimethyl-2-phenyl-4,5-dihydro-imidazol-1-yl)-2-methyl-propyl]-3H-quinazolin-4-one trifluoroacetate | A | 499 |
| 3-Benzyl-7-chloro-2-{1-[2-(3,4-dichloro-phenyl)-4,4-dimethyl-4,5-dihydro-imidazol-1-yl]-2-methyl-propyl}-3H-quinazolin-4-one | A | 567 |

-continued

| Compound | Method | MS (ES+) m/e [M + H]+ |
|---|---|---|
| 3-Benzyl-7-chloro-2-{1-[2-(3,4-dimethoxy-phenyl)-4,4-dimethyl-4,5-dihydro-imidazol-1-yl]-2-methyl-propyl}-3H-quinazolin-4-one | B | 559 |
| 2-[1-(2-Benzo[1,3]dioxol-5-yl-4,4-dimethyl-4,5-dihydro-imidazol-1-yl)-2-methyl-propyl]-3-benzyl-7-chloro-3H-quinazolin-4-one | B | 543 |
| 3-{1-[1-(3-Benzyl-7-chloro-4-oxo-3,4-dihydro-quinazolin-2-yl)-2-methyl-propyl]-4,4-dimethyl-4,5-dihydro-1H-imidazol-2-yl}-benzonitrile | B | 524 |
| 3-Benzyl-7-chloro-2-{1-[2-(2-chloro-6-methyl-pyridin-4-yl)-4,4-dimethyl-4,5-dihydro-imidazol-1-yl]-2-methyl-propyl}-3H-quinazolin-4-one | B | 548 |
| 3-Benzyl-7-chloro-2-{1-[4,4-dimethyl-2-(5-methyl-isoxazol-3-yl)-4,5-dihydro-imidazol-1-yl]-2-methyl-propyl}-3H-quinazolin-4-one | B | 504 |
| 3-Benzyl-7-chloro-2-{1-[2-(4-fluoro-3-methyl-phenyl)-4,4-dimethyl-4,5-dihydro-imidazol-1-yl]-2-methyl-propyl}-3H-quinazolin-4-one | B | 531 |
| 3-Benzyl-7-chloro-2-{1-[2-(3,5-dimethoxy-phenyl)-4,4-dimethyl-4,5-dihydro-imidazol-1-yl]-2-methyl-propyl}-3H-quinazolin-4-one | B | 559 |
| 3-Benzyl-7-chloro-2-{1-[2-(2,3-difluoro-4-methyl-phenyl)-4,4-dimethyl-4,5-dihydro-imidazol-1-yl]-2-methyl-propyl}-3H-quinazolin-4-one | A | 549 |
| 3-Benzyl-7-chloro-2-{1-[2-(3-dimethylamino-phenyl)-4,4-dimethyl-4,5-dihydro-imidazol-1-yl]-2-methyl-propyl}-3H-quinazolin-4-one | A | 542 |
| 3-Benzyl-7-chloro-2-{1-[2-(4-dimethylamino-phenyl)-4,4-dimethyl-4,5-dihydro-imidazol-1-yl]-2-methyl-propyl}-3H-quinazolin-4-one | A | 542 |
| 3-Benzyl-7-chloro-2-{1-[2-(4-isopropyl-phenyl)-4,4-dimethyl-4,5-dihydro-imidazol-1-yl]-2-methyl-propyl}-3H-quinazolin-4-one | A | 541 |
| 3-Benzyl-7-chloro-2-{1-[2-(3-chloro-4-methyl-phenyl)-4,4-dimethyl-4,5-dihydro-imidazol-1-yl]-2-methyl-propyl}-3H-quinazolin-4-one | A | 547 |
| 3-Benzyl-2-{1-[2-(3-bromo-4-methyl-phenyl)-4,4-dimethyl-4,5-dihydro-imidazol-1-yl]-2-methyl-propyl}-3H-quinazolin-4-one | A | 591 |
| 4-{1-[1-(3-Benzyl-7-chloro-4-oxo-3,4-dihydro-quinazolin-2-yl)-2-methyl-propyl]-4,4-dimethyl-4,5-dihydro-1H-imidazol-2-yl}-benzonitrile | A | 524 |
| 3-Benzyl-7-chloro-2-[1-(4,4-dimethyl-2-(2-tolyl)-4,5-dihydro-imidazol-1-yl]-2-methyl-propyl]-3H-quinazolin-4-one | A | 513 |
| 3-Benzyl-7-chloro-2-[1-(4,4-dimethyl-2-pyridin-3-yl-4,5-dihydro-imidazol-1-yl)-2-methyl-propyl]-3H-quinazolin-4-one | A | 500 |
| 3-Benzyl-7-chloro-2-[1-(4,4-dimethyl-2-pyridin-4-yl-4,5-dihydro-imidazol-1-yl)-2-methyl-propyl]-3H-quinazolin-4-one | A | 500 |
| (±)-3-Benzyl-7-chloro-2-{1-[2-(3-fluoro-4-methyl-phenyl)-4,5-dihydro-imidazol-1-yl]-2-methyl-propyl}-3H-quinazolin-4-one | A | 503 |
| (±)-3-Benzyl-2-{1-[2-(4-bromo-phenyl)-4,5-dihydro-imidazol-1-yl]-2-methyl-propyl}-7-chloro-3H-quinazolin-4-one | A | 549 |
| 3-Benzyl-7-chloro-2-{1-[(S)-2-(3-fluoro-4-methyl-phenyl)-4-methyl-4,5-dihydro-imidazol-1-yl]-2-methyl-propyl}-3H-quinazolin-4-one | A | 517 |
| 3-Benzyl-7-chloro-2-[2-methyl-1-((S)-4-methyl-2-p-tolyl-4,5-dihydro-imidazol-1-yl)-propyl]-3H-quinazolin-4-one | A | 499 |
| 3-Benzyl-7-chloro-2-{1-[2-(2-methoxy-ethyl)-4,4-dimethyl-4,5-dihydro-imidazol-1-yl]-2-methyl-propyl}-3H-quinazolin-4-one | A | 480 |
| 3-Benzyl-7-chloro-2-[1-(2-isopropyl-4,4-dimethyl-4,5-dihydro-imidazol-1-yl)-2-methyl-propyl]-3H-quinazolin-4-one | A | 465 |
| 3-Benzyl-7-chloro-2-[1-(4,4-dimethyl-2-quinoxalin-2-yl-4,5-dihydro-imidazol-1-yl)-2-methyl-propyl]-3H-quinazolin-4-one | B | 550 |

-continued

| Compound | Method | MS (ES+) m/e [M + H]+ |
|---|---|---|
| 3-Benzyl-7-chloro-2-{1-[2-(4-ethyl-phenyl)-4,4-dimethyl-4,5-dihydro-imidazol-1-yl]-2-methyl-propyl}-3H-quinazolin-4-one | B | 526 |
| 3-Benzyl-7-chloro-2-[(R)-2-methyl-1-(2-p-tolyl-4,5-dihydro-imidazol-1-yl)-propyl]-3H-quinazolin-4-one | A | 485 |
| N-(4-{1-[1-(3-Benzyl-7-chloro-4-oxo-3,4-dihydro-quinazolin-2-yl)-2-methyl-propyl]-4,4-dimethyl-4,5-dihydro-1H-imidazol-2-yl}-phenyl)-acetamide | A | 556 |
| 3-Benzyl-7-chloro-2-{1-[2-(3-fluoro-4-methyl-phenyl)-4,5-dihydro-imidazol-1-yl]-2-methyl-propyl}-3H-quinazolin-4-one | A | 503 |
| 3-Benzyl-2-{1-[2-(4-bromo-phenyl)-4,5-dihydro-imidazol-1-yl]-2-methyl-propyl}-7-chloro-3H-quinazolin-4-one | A | 548 |
| 3-Benzyl-7-chloro-2-{(R)-1-[2-(3-fluoro-4-methyl-phenyl)-4,5-dihydro-imidazol-1-yl]-2-methyl-propyl}-3H-quinazolin-4-one | A | 503 |

Example 11

3-Benzyl-7-chloro-2-{1-[2-(methoxymethyl)-imidazol-1-yl]-2-methyl-propyl}-3H-quinazolin-4-one

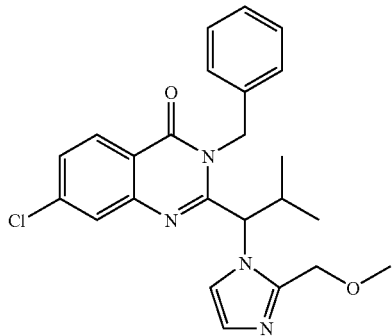

The title compound was prepared as in example one, except substituting methoxyacetyl chloride for benzoyl chloride, as tan crystals (15%). MS(ES+) m/e 437 [M+H]+.

Example 12

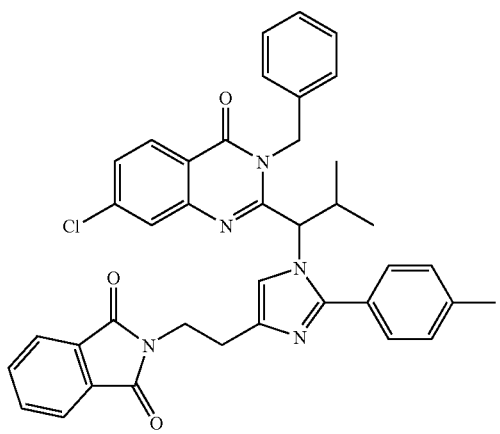

2-(2-{1-[1-(3-Benzyl-7-chloro-4-oxo-3,4-dihydro-quinazolin-2-yl)-2-methyl-propyl]-2-p-tolyl-1H-imidazol-4-yl}-ethyl)-isoindole-1,3-dione a) 2-{4-[1-(3-Benzyl-7-chloro-4-oxo-3,4-dihydro-quinazolin-2-yl)-2-methyl-propylamino]-3-oxo-butyl}-isoindole-1,3-dione A suspension of 2-(1-amino-2-methyl-propyl)-3-benzyl-7-chloro-3H-quinazolin-4-one (1.0 g, 2.93 mmol), 2-(4-bromo-3-oxo-butyl)-isoindole-1,3-dione (867 mg., 2.93 mmol, prepared as described in WO 89/10360), and potassium carbonate (405 mg, 2.93 mmol) in DMF (14 mL) was stirred at room temperature for 80 minutes. The reaction was diluted with water and the resulting white solid (1.6 g) was used in the subsequent step without further purification.

b) N-[1-(3-Benzyl-7-chloro-4-oxo-3,4-dihydro-quinazolin-2-yl)-2-methyl-propyl]-N-[4-(1,3-dioxo-1,3-dihydro-isoindol-2-yl)-2-oxo-butyl]-4-methyl-benzamide A solution of 2-{4-[1-(3-benzyl-7-chloro-4-oxo-3,4-dihydro-quinazolin-2-yl)-2-methyl-propylamino]-3-oxo-butyl}-isoindole-1,3-dione (1.5 g from previous step), triethylamine (245 mg, 2.42 mmol), and p-toluoyl chloride (374 mg, 2,42 mmol) in methylene chloride (10 mL) was stirred at room temperature for 2.0 h. The reaction was washed sequentially with 0.5 N HCl, water, 5% NaHCO₃, water, and brine and dried (Na₂SO₄). The filtrate was concentrated in vacuo and purified by flash chromatography (silica gel 3:2 hexanes: EtOAc as eluent) to provide the title compound as a white solid (0.7 g, 35%, 2 steps). MS(ES+) m/e 675 [M+H]+.

c) 2-(2-{1-[1-(3-Benzyl-7-chloro-4-oxo-3,4-dihydro-quinazolin-2-yl)-2-methyl-propyl]-2-p-tolyl-1H-imidazol-4-yl}-ethyl)-isoindole-1,3-dione A solution of N-[1-(3'-benzyl-7-chloro-4-oxo-3,4-dihydro-quinazolin-2-yl)-2-methyl-propyl]-N-[4-(1,3-dioxo-1,3-dihydro-isoindol-2-yl)-2-oxo-butyl]-4-methyl-benzamide (641 mg, 0.948 mmol) and ammonium acetate (3.65 g, 47.4 mmol) in acetic acid (30 mL) was refluxed for 6.0 h using a Dean-Stark trap and condenser. The reaction was concentrated in vacuo and the residue was triturated with water, dried in a Buchner funnel, and recrystallized from ethanol to provide the title compound as a white solid (320 mg, 51%). MS(ES+) n/e 656 [M+H]+.

Example 13

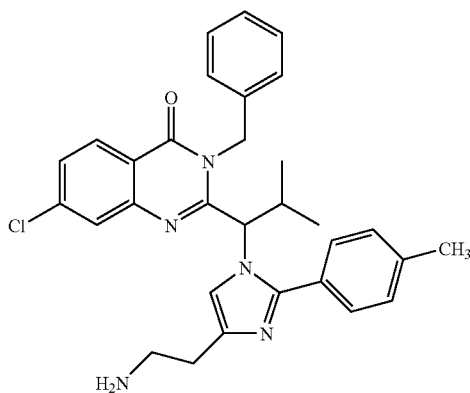

2-{1-[4-(2-Amino-ethyl)-2-p-tolyl-imidazol-1-yl]-2-methyl-propyl}-3-benzyl-7-chloro-3H-quinazolin-4-one A solution of 2-(2-{1-[1-(3-benzyl-7-chloro-4-oxo-3,4-dihydro-quinazolin-2-yl)-2-methyl-propyl]-2-p-tolyl-1H-imidazol-4-yl}-ethyl)-isoindole-1,3-dione (278 mg, 0.423 mmol) and anhydrous hydrazine (98 mg, 3.06 mmol) in EtOH (12 mL) was refluxed for 3.0 h. The reaction was cooled to 5° C. and a white precipitate was filtered off. The filtrate was concentrated in vacuo and purified by flash chromatography (silica gel, 90:9:1 methylene chloride:methanol:ammonium hydroxide as eluent) to provide the title compound as a white solid (98.2 mg, 45%). MS(ES+) m/e 526 [M+H]+.

Example 14

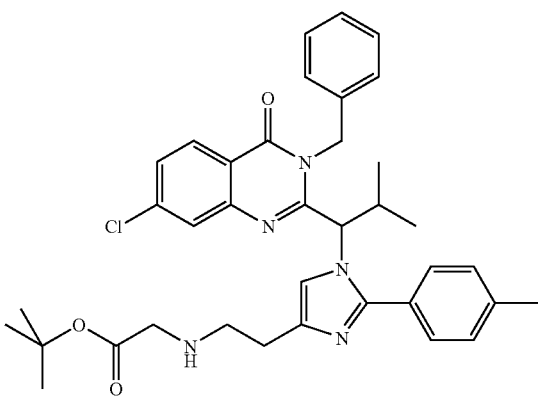

(2-{1-[1-(3-Benzyl-7-chloro-4-oxo-3,4-dihydro-quinazolin-2-yl)-2-methyl-propyl]-2-p-tolyl-1H-imidazol-4-yl}-ethylamino)-acetic acid tert-butyl ester A solution of 2-{1-[4-(2-Amino-ethyl)-2-p-tolyl-imidazol-1-yl]-2-methyl-propyl}-3-benzyl-7-chloro-3H-quinazo-lin-4-one (181 mg, 0.343 mmol), potassium carbonate (47 mg., 0.343 mmol), and tert-butyl bromoacetate (67 mg., 0.343 mmol) in DMF (2.0 mL) was stirred at room temperature for 4.5 h. The reaction was diluted with water and the resulting white precipitate was filtered and purified by flash chromatography (silica gel, 95:5 methylene chloride:methanol) to provide the title compound as a white solid (109 mg., 50%). MS(ES+) m/e 640 [M+H]+.

Example 15

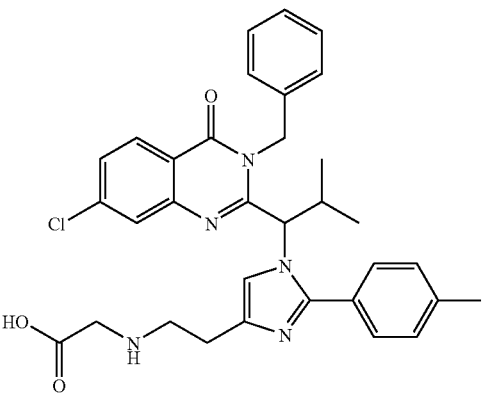

(2-{1-[1-(3-Benzyl-7-chloro-4-oxo-3,4-dihydro-quinazolin-2-yl)-2-methyl-propyl]-2-p-tolyl-1H-imidazol-4-yl}-ethylamino)-acetic acid A solution of (2-{1-[1-(3-benzyl-7-chloro-4-oxo-3,4-dihydro-quinazolin-2-yl)-2-methyl-propyl]-2-p-tolyl-1H-imidazol-4-yl}-ethylamino)-acetic acid tert-butyl ester (99.6 mg., 0.155 mmol) and trifluoroacetic acid (8 mL) in methylene chloride (4 mL) was stirred at room temperature for 3.0 h. The reaction was concentrated in vacuo and the residue was triturated with diethyl ether and dried to provide the title compound as a white solid (67 mg., 53%). MS(ES+) m/e 584 [M+H]+.

Example 16

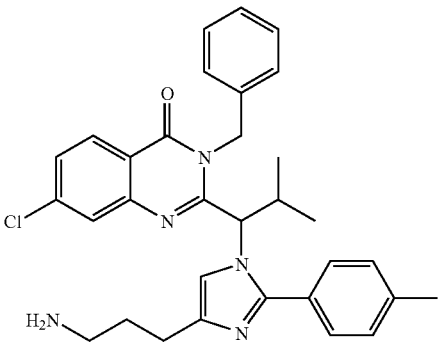

2-{1-[4-(3-Amino-propyl)-2-p-tolyl-imidazol-1-yl]-2-methyl-propyl}-3-benzyl-7-chloro-3H-quinazolin-4-one The title compound was prepared as in example 12 and 13, except substituting 2-(5-bromo-4-oxo-pentyl)-isoindole-1,3-dione for 2-(4-bromo-3-oxo-butyl)-isoindole-1,3-dione (as described in J. Med. Chem. 35, 3239 (1992)), as a white solid (61%). MS(ES+) m/e 540 [M+H]⁺.

Example 17

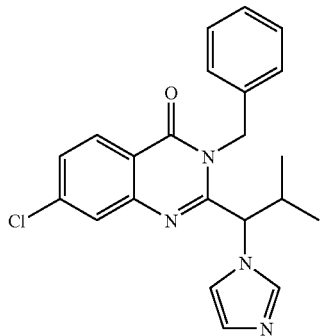

(±)-3-Benzyl-7-chloro-2-(1-imidazol-1-yl-2-methyl-propyl)-3H-quinazolin-4-one

To a solution of (±)-3-benzyl-2-(1-bromo-2-methyl-propyl)-7-chloro-3H-quinazolin-4-one (a compound of Formula 105, 250 mg, 0.616 mmol) in DMF (3 mL) was added triethylamine (0.130 mL, 0.924 mmol) and imidazole (63.0 mg, 0.924 mmol) followed by tetrabutylammonium iodide (228 mg, 0.616 mmol). The resultant solution was heated to 90° C., stirred for 18 h and allowed to cool to room temperature. The reaction mixture was quenched with water (3 mL) and diluted with ether (10 mL). The aqueous layer was extracted with ether (10 mL) ad the combined extracts were dried over MgSO₄, filtered and concentrated under reduced pressure. The residue was purified by silica gel chromatography (1:1 hexanes:ethyl acetate) to provide 38 mg (16%) of the title compound as a yellow solid. MS(ES+) m/e 393.0 [M+H]⁺.

Example 18

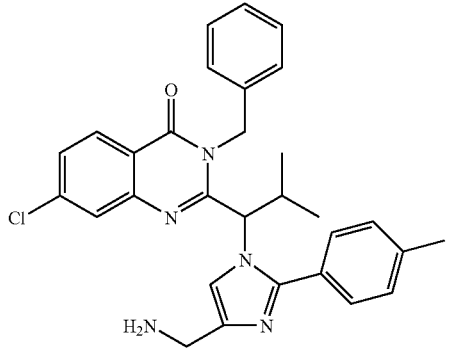

2-[(R)-1-(4-Aminomethyl-2-p-tolyl-imidazol-1-yl)-2-methyl-propyl]-3-benzyl-7-chloro-3H-quinazolin-4-one a) 2-[(R)-1-(3-Phthalimido-2-oxo-propylamino)-2-methyl-propyl]-3-benzyl-7-chloro-3H-quinazolin-4-one To 2-((R)-1-amino-2-methyl-propyl)-3-benzyl-7-chloro-3H-quinazolin-4-one (5.0 g, 14.6 mMol) and K₂CO₃ (2.1 g, 15.2 mMol) in DMF (50 mL) was added N-(3-Bromo-2-oxopropyl)-phthalimide (4.5 g, 14.8 mMol) (Nair et al.; J. Org. Chem.; 40; 1975; 1745). The reaction was stirred at RT for 3 h, concentrated under vacuum, taken up in EtOAc, washed with water, brine, dried (Na₂SO₄) and evaporated to give the title compound (7.94 g, 14.6 mMol) as an off-white solid: MS (ES) m/e 543.2 (M+H)⁺.

b) 2-{(R)-1-[N-Toluoyl-(3-Phthalimido-2-oxo-propyl)amino]-2-methyl-propyl}-3-benzyl-7-chloro-3H-quinazolin-4-one To 2-[(R)-1-(3-phthalimido-2-oxo-propylamino)-2-methyl-propyl]-3-benzyl-7-chloro-3H-quinazolin-4-one (7.22 g, 13.3 mMol) in CH₂Cl₂ (50 mL) was added Et₃N (2.0 mL, 14.3 mMol) and toluoyl chloride (1.9 mL, 14.4 mMol). The reaction was stirred at RT for 18 h, concentrated under vacuum, taken up in EtOAc, washed with 1 N HCl, brine, dried (MgSO₄) and evaporated to dryness. Purification by flash chromatography on silica gel (1% MeOH/CH₂Cl₂) followed by trituration with (1:1) Et₂O/pet. ether, filtration and drying under vacuum gave the title compound (6.41 g, 73%) as a white solid. A side fraction (1.20 g) which contained mostly product was also obtained: ¹H NMR (400 MHz, CDCl₃) δ 8.23 (d, J=8.6 Hz, 1 H), 7.69-7.78 (m, 5 H), 7.45-7.49 (m, 3 H), 7.34 (t, 2 H), 7.25-7.29 (m, 3 H), 7.15 (d, J=8.1 Hz, 2 H), 6.19 (d, J=15.9 Hz, 1H), 5.82 (d, J=10.6 Hz, 1H), 5.12 (d, J=15.9 Hz, 1H), 4.56 (d, J=18.8 Hz, 1 H), 4.26 (d, J=18.8 Hz, 1 H), 4.09 (d, J=17.6 Hz, 1 H), 3.90 (d, J=17.6 Hz, 1H), 2.62 (n, 1 H), 2.42 (s, 3 H), 0.93 (d, J=6.8 Hz, 3 H), 0.32 (d, J=6.4 Hz, 3 H); MS (ES) m/e 661.2 (M+H)⁺.

c) N-{1-[(R)-1-(3-Benzyl-7-chloro-4-oxo-3,4-dihydro-quinazolin-2-yl)-2-methyl-propyl]-2-p-tolyl-1H-imidazol-4-ylmethyl}-acetamide (SB-767470) and N-{1-[(R)-1-(3-Benzyl-7-chloro-4-oxo-3,4-dihydro-quinazolin-2-yl)-2-methyl-propyl]-2-p-tolyl-1H-imidazol-4-ylmethyl}-phthalimide To 2-{(R)-1-[N-toluoyl-(3-phthalimido-2-oxo-propyl)amino]-2-methyl-propyl}-3-benzyl-7-chloro-3H-quinazolin-4-one (6.0 g, 9.1 mMol) and NH₄OAc (35 g 450 mMol) was added HOAc (100 mL). The reaction was stirred and heated to reflux (155° C. oil bath) for 6 h. After cooling to RT the reaction was concentrated under vacuum and poured into ice water (500 mL). The fine white precipitate which formed was filtered off (slow!), rinsed with water then dried under vacuum. Purification by flash chromatography on silica gel (50% EtOAc/hexane to EtOAc to 5% MeOH/EtOAc) after trituration with (1:1) Et₂O/pet. ether, filtration and drying under vacuum gave the title compound N-{1-[(R)-1-(3-benzyl-7-chloro-4-oxo-3,4-dihydro-quinazolin-2-yl)-2-methyl-propyl]-2-p-tolyl-1H-imidazol-4-ylmethyl}-phthalimide (3.77 g, 65%) as a white solid: ¹H NMR (400 MHz, CDCl₃) δ 8.23 (d, J=8.6 Hz, 1 H), 7.87 (m, 2 H), 7.72 (m, 2 H), 7.68 (d, J=1.7 Hz, 1 H), 7.61 (s, 1 H), 7.46-7.50 (m, 3 H), 7.40 (d, J=7.9 Hz, 2 H), 7.15-7.22 (m, 3 H), 6.47 (d, J=7.0 Hz, 2 H), 5.75 (d, J=16.3 Hz, 1 H), 4.89 (m, 3 H), 3.79 (d, J=16.3 Hz, 1 H), 2.93 (m, 1 H), 2.52 (s, 3 H), 0.89 (d, J=6.8 Hz, 3 H). 0.25 (d, J=6.8 Hz, 3 H); MS (ES) m/e 642.2 (M+H)⁺.

d) 2-[(R)-1-(4-Aminomethyl-2-p-tolyl-imidazol-1-yl)-2-methyl-propyl]-3-benzyl-7-chloro-3H-quinazolin-4-one To N-{1-[(R)-1-(3-benzyl-7-chloro-4-oxo-3,4-dihydro-quinazolin-2-yl)-2-methyl-propyl]-2-p-tolyl-1H-imidazol- 4-ylmethyl}-phthalimide (3.50 g, 5.5 mMol) in EtOH (100 mL) was added hydrazine monohydrate (1.1 mL, 22.7 mMol). The reaction was stirred at RT for 72 h, filtered through a pad of Celite® to remove the insoluble precipitate, rinsed with EtOH and evaporated to dryness. Purification by flash chromatography on silica gel [5-10% (5% NH$_4$OH in MeOH)/CH$_2$Cl$_2$] gave the title compound (2.71 g, 96%) as a white solid: $^1$H NMR (400 MHz, CDCl$_3$) δ 8.24 (d, J=8.6 Hz, 1 H), 7.80 (d, J=2.0 Hz, 1 H), 7.40-7.51 (m, 6 H), 7.15-7.22 (m, 3 H), 6.43 (d, J=7.1 Hz, 2 H), 5.78 (d, J=16.3 Hz, 1 H), 4.84 (d, J=10.5 Hz, 1 H), 3.87 (d, J=16.3 Hz, 1 H), 3.83 (2d, 2H), 3.00 (m, 1 H), 2.60 (br s, 2H), 2.54 (s, 3 H), 0.90 (d, J=6.7 Hz, 3 H), 0.31 (d, J=6.7 Hz, 3 H); MS (ES) m/e 512.2 (M+H)$^+$.

Example 19

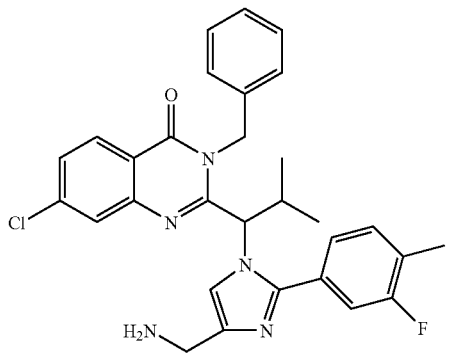

2-{(R)-1-[4-Aminomethyl-2-(3-fluoro-4-methyl-benzoyl)-imidazol-1-yl]-2-methyl-propyl}-3-benzyl-7-chloro-3H-quinazolin-4-one According to the procedure of Example 18, the title compound (191 mg, 61%) was prepared as an off-white solid: $^1$H NMR (400 MHz, CDCl$_3$) δ 8.24 (d, J=8.6 Hz, 1 H), 7.8 (d, J=1.9 Hz, 1 H), 7.49 (m, 2H), 7.41 (appt, 1 H), 7.19-7.32 (m, 5 H), 6.48 (d, J=6.7 Hz, 2 H), 5.81 (d, J=16.4 Hz, 1 H), 4.88 (d, J=10.5 Hz, 1 H), 3.90 (d, J=16.4 Hz, 1 H), 3.85 (2d, 2H), 3.02 (m, 1 H), 2.82 (br s, 2 H), 2.46 (s, 3 H), 0.90 (d, J=6.7 Hz, 3H), 0.37 (d, J=6.7 Hz, 3 H); MS (ES) m/e 530.2 (M+H)$^+$.

Example 20

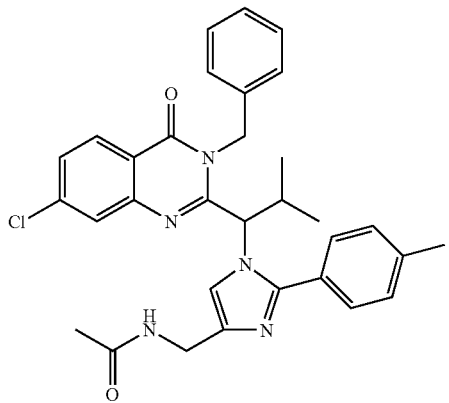

N-{1-[(R)-1-(3-Benzyl-7-chloro-4-oxo-3,4-dihydro-quinazolin-2-yl)-2-methyl-propyl]-2-p-tolyl-1H-imidazol-4-ylmethyl}-acetamide A second product was isolated during the chromatographic purification of Example 18c, which was triturated with Et$_2$O, filtered and dried under vacuum to give the title compound N-{1-[(R)-1-(3-benzyl-7-chloro-4-oxo-3,4-dihydro-quinazolin-2-yl)-2-methyl-propyl]-2-p-tolyl-1H-imidazol-4-ylmethyl}-acetamide (0.87 g, 17%) as a white solid: $^1$H NMR (400 MHz, CDCl$_3$) δ 8.24 (d, J=8.6 Hz, 1 H), 7.80 (d, J=2.0 Hz, 1 H), 7.49-7.51 (m, 4 H), 7.43 (d, J=8.0 Hz, 2 H), 7.16-7.23 (m, 3 H), 6.43 (d, J=7.1 Hz, 2 H), 6.30 (br s, 1 H), 5.80 (d, J=16.3 Hz, 1 H), 4.87 (d, J=10.6 Hz, 1 H), 4.40 (d, 1 H), 4.36 (d, 1 H), 3.84 (d, J=16.3 Hz, 1 H), 3.00 (m, 1H), 2.56 (s, 3H), 1.98 (s, 3 H), 0.90 (d, J=6.8 Hz, 3 H), 0.30 (d, J=6.6 Hz, 3H); MS (ES) m/e 554.2 (M+H)$^+$.

Example 21

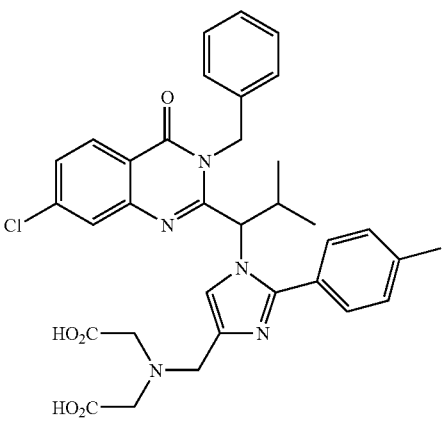

2-{(R)-1-[4-(N,N-Dicarboxymethyl)aminomethyl-2-p-tolyl-imidazol-1-yl]-2-methyl-propyl}-3-benzyl-7-chloro-3H-quinazolin-4-one a) 2-{(R)-1-[4-(N,N-Di-t-butoxycarbonylmethyl)aminomethyl-2-p-tolyl-imidazo-1-yl]-2-methyl-propyl}-3-benzyl-7-chloro-3H-quinazolin-4-one and 2-{(R)-1-[4-(N-t-butoxycarbonylmethyl)aminomethyl-2-p-tolyl-imidazol-1-yl]-2-methyl-propyl}-3-benzyl-7-chloro-3H-quinazolin-4-one To 2-[(R)-1-(4-aminomethyl-2-p-tolyl-imidazol-1-yl)-2-methyl-propyl]-3-benzyl-7-chloro-3H-quinazolin-4-one (0.35 g, 0.68 mMol) (from example 18d) and K$_2$CO$_3$ (100 mg, 0.72 mMol) in DMF (10 mL) was added t-butyl bromoacetate (103 uL, 0.68 mMol). The reaction was stirred at RT for 18 h, concentrated under vacuum, triturated with cold water, filtered and dried under vacuum. Purification by flash chromatography on silica get (1-5% (5% NH$_4$OH in MeOH)/(20% EtOAc in CH$_9$Cl$_2$) gave the title compound 2-{(R)-1-[4-(N,N-di-t-butoxycarbonylmethyl)aminomethyl-2-p-tolyl-imidazol-1-yl]-2-methyl-propyl}-3-benzyl-7-chloro-3H-quinazolin-4-one (0.23 g, 46%) as a white solid: MS (ES) m/e 740.2 (M+H)$^+$.

b) 2-{(R)-1-[4-(N,N-Dicarboxymethyl)aminomethyl-2-p-tolyl-imidazol-1-yl]-2-methyl-propyl}-3-benzyl-7-chloro-3H-quinazolin-4-one To 2-{(R)-1-[4-(N,N-di-t-butoxycarbonylmethyl)aminomethyl-2-p-tolyl-imidazol-1-yl]-2-methyl-propyl}-3-benzyl-7-chloro-3H-quinazolin-4-one (0.23 g, 0.31 mMol) was added TFA (20 mL). The reaction was stirred at RT for 4 h and evaporated to dryness under vacuum. Trituration with (1:1) Et$_2$O/pet. ether, filtration and drying under vacuum gave the title compound 2-{(R)-1-[4-(N,N-dicarboxymethyl)aminomethyl-2-p-tolyl-imidazol-1-yl]-2-methyl-propyl}-3-benzyl-7-chloro-3H-quinazolin-4-one (203 mg, 77%) as a white solid: $^1$H NMR (400 MHz, d$_6$-DMSO) δ 8.19 (d, J±8.6 H), 8.14 (s, 1 H), 7.91 (d, J=1.8 Hz, 1 H), 7.68 (dd, 1 H), 7.52-7.55 (m, 4 H), 7.21-7.25 (m, 3H), 6.50 (d, J=5.9 Hz, 2 H), 5.59 (d, J=16.7 Hz, 1 H), 4.88 (d, J=10.1 Hz, 1 H), 4.13 (d, J=14.6 Hz, 1 H), 4.05 (d, J=14.6 Hz, 1H), 4.00 (d, J=16.8 Hz, 1 H), 3.68 (s, 4 H), 2.78 (m, 1 H), 0.80 (d, J=6.7 Hz, 3 H), 0.26 (d, J=6.5 Hz, 3 H).

Example 22

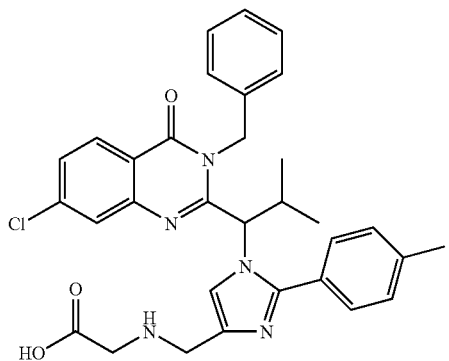

2-{(R)-1-[4-(N-Carboxymethyl)aminomethyl-2-p-tolyl-imidazol-1-yl]-2-methyl-propyl}-3-benzyl-7-chloro-3H-quinazolin-4-one During the chromatographic purification of Example 21a, second compound, 2-{(R)-1-[4-t-butoxycarbonylmethyl)aminomethyl-2-p-tolyl-imidazol-1-yl]-2-methyl-propyl}-3-benzyl-7-chloro-3H-quinazolin-4-one, was obtained (0.10 g, 24%) as a white solid: MS (ES) m/e 626.2 (M+H)$^+$. According to the procedure of Example 20b, 2-{(R)-1-[4-(N-t-butoxycarbonylmethyl)aminomethyl-2-p-tolyl-imidazol-1-yl]-2-methyl-propyl}-3-benzyl-7-chloro-3H-quinazolin-4-one (0.10 g, 0.16 mMol) was converted to the title compound (102 mg, 80%) as a white solid: $^1$H NMR (400 MHz, d$_6$-DMSO) δ 8.18 (d, J=8.5 Hz, 1 H), 7.88 (d, J=1.8 Hz, 1 H), 7.86 (s, 1 H), 7.67 (dd, 1 H), 7.41-7.57 (m, 4 H), 7.22-7.27 (m, 3 H), 6.46 (d, J=7.5 Hz, 2 H), 5.56 (d, J=16.7 Hz, 1 H), 4.84 (d, J=10.3 Hz, 1 H), 4.15 (d, J=13.7 Hz, 1 H), 4.10 (d, J=13.8 Hz, 1 H), 4.02 (d, J=16.6 Hz, 1 H), 3.89 (s, 2 H), 2.85 (m, 1 H), 0.80 (d, J=6.7 Hz, 3 H), 0.34 (d, J=6.7 Hz, 3 H).

Example 23

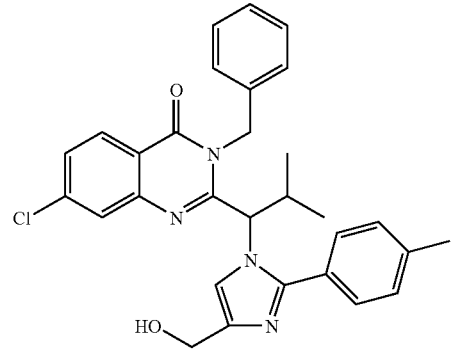

3-Benzyl-7-chloro-2-[(R)-1-(4-hydroxymethyl-2-p-tolyl-imidazol-1-yl)-2-methyl-propyl]-3H-quinazolin-4-one a) 2-[(R)-1-(3-Toluoyloxy-2-oxo-propylamino)-2-methyl-propyl]-3-benzyl-7-chloro-3H-quinazolin-4-one To 2-((R)-1-amino-2-methyl-propyl)-3-benzyl-7-chloro-3H-quinazolin-4-one (1.0 g, 2.9 mMol) in DMF (10 mL) was added DIEA (0.6 mL, 3.4 mMol) and 1-toluoyloxy-3-bromopropan-2-one (1.0 g, 3.7 mMol) (Prepared using the procedure of F. C. Hartman, *Biochemistry*, 9, 1776 (1970) except substituting toluoyl chloride for benzoyl chloride.) The reaction was stirred at RT for 18 h, concentrated under vacuum, taken up in EtOAc, washed with 1 N Na$_2$CO$_3$, dried (Na$_2$SO$_4$) and evaporated to dryness. The product was converted to its hydrochloride salt by treating with 4 N HCl in dioxane (20 mL) and concentration under vacuum. Trituration with (1:1) Et$_2$O/pet. ether, filtration and drying under vacuum left the title compound (1.87 g, 100%, 88% pure) as a beige solid: MS (ES) m/e 532.2 (M+H)$^+$.

b) 2-{(R)-1-[N-Toluoyl-(3-toluoyloxy-2-oxo-propyl)amino]-2-methyl-propyl}-3-benzyl-7-chloro-3H-quinazolin-4-one To 2-[(R)-1-(3-toluoyloxy-2-oxo-propylamino)-2-methyl-propyl]-3-benzyl-7-chloro-3H-quinazolin-4-one (1.87 g, 2.9 mMol) in CH$_2$Cl$_2$ (30 mL) was added Et$_3$N (1 mL, 7.1 mMol) and toluoyl chloride (0.44 mL, 3.3 mMol). The reaction was stirred at RT for 18 h, concentrated under vacuum, taken up in EtOAc, washed with 1 N HCl, brine, dried (MgSO$_4$) and evaporated to dryness. Purification by flash chromatography on silica gel (20% EtOAc/hexane) gave the title compound (1.76 g, 93%) as a white-solid: MS (ES) m/e 650.4 (M+H)$^+$.

c) 3-Benzyl-7-chloro-2-[(R)-1-(4-hydroxymethyl-2-p-tolyl-imidazol-1-yl)-2-methyl-propyl]-3H-quinazolin-4-one (SB-792813)

To a mixture of 2-{(R)-1-[N-toluoyl-(3-toluoyloxy-2-oxo-propyl)amino]-2-methyl-propyl}-3-benzyl-7-chloro-3H-quinazolin-4-one (1.50 g, 2.3 mMol) and NH4OAc (8.9 g, 115 mMol) was added HOAc (30 mL). The reaction was heated to reflux (155° C. oil bath) and stirred for 2.5 h. After cooling to RT the reaction was concentrated under vacuum, taken up in EtOAc, washed with water, 1 N Na$_2$CO$_3$, brine, dried (MgSO₄) and evaporated to dryness. To this crude mixture of alcohol, toluoyl and acetyl esters was added MeOH (20 mL) and 1 N NaOH (5 mL). The reaction was stirred at RT for 18 h, neutralized with 1 N HCl (5 mL) and evaporated under vacuum. The remaining solid was taken up in EtOAc, washed with water, brine, dried (MgSO₄) and evaporated to dryness. Purification by flash chromatography on silica gel (80-100% EtOAc/hexane) gave the title compound (0.95 g, 81%) as an off-white solid: ¹H NMR (400 MHz, CDCl₃) δ 8.25 (d, J=8.6 Hz, 1 H), 7.78 (d, J=1.8 Hz, 1 H), 7.48-7.54 (m, 4 H), 7.43 (d, J=7.9 Hz, 2 H), 7.16-7.23 (m, 3 H), 6.43 (d, J=7.2 Hz, 2 H), 5.78 (d, J =16.3 Hz, 1 H), 4.88 (d, J=10.5 Hz, 1 H), 4.64 (d, J=12.9 Hz, 1 H), 4.60 (d, J=12.9 Hz, 1 H), 3.84 (d, J=16.3 Hz, 1 H), 3.01 (ml, 1 H), 2.75 (br s, 1 H), 2.55 (s, 3 H), 0.90 (d, J=6.7 Hz, 3 H), 0.32 (d, J=6.7 Hz, 3 H); MS (ES) m/e 513.2 (M+H)⁺.

Example 24

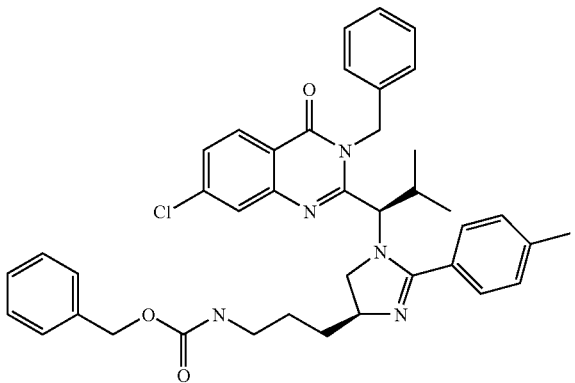

(3-{(S)-1-[(R)-1-(3-Benzyl-7-chloro-4-oxo-3,4-dihydro-quinazolin-2-yl)-2-methyl-propyl]-2-p-tolyl-4,5-dihydro-1H-imidazol-4-yl}-propyl)-carbamic acid benzyl ester a) ((S)-1-{[(R)-1-(3-Benzyl-7-chloro-4-oxo-3,4-dihydro-quinazolin-2-yl)-2-methyl-propylamino]-methyl}-4-benzyloxycarbonylamino-butyl)-carbamic acid tert-butyl ester To a solution of 2-((R)-1-amino-2-methyl-propyl)-3-benzyl-7-chloro-3H-quinazolin-4-one (a compound of Formula 107, 366 mg, 1.07 mmol) and ((S)-4-benzyloxycarbonylamino-1-formyl-butyl)-carbamic acid tert-butyl ester (prepared as previously described: Hamada, Y.; Shioro, T. Chem. Pharm. Bull. 1982, 30, 1921) (452 mg, 1.29 mmol) in CH₂Cl₂ (25 mL) was added sodium triacetoxyborohydride (341 mg, 1.61 mmol). The resultant cloudy mixture was stirred overnight and quenched with saturated brine (50 mL). The aqueous layer was extracted with CH₂Cl₂ (20 mL) and the combined extracts were dried over MgSO₄, filtered and concentrated under reduced pressure. The residue was purified by silica gel chromatography (2:1 hexanes:ethyl acetate) to provide 550 mg (76%) of the title compound as a yellow oil. MS(ES+) m/e 676.4 [M+H]⁺.

b) (1-{[[1-(3-Benzyl-7-chloro-4-oxo-3,4-dihydro-quinazolin-2-yl)-2-methyl-propyl]-(1-p-tolyl-methanoyl)-amino]-methyl}-4-benzyloxycarbonylamino-butyl)-carbamic acid tert-butyl ester To a solution of ((S)-1-{[(R)-1-(3-benzyl-7-chloro-4-oxo-3,4-dihydro-quinazolin-2-yl)-2-methyl-propylamino]-methyl}-4-benzyloxycarbonylamino-butyl)-carbamic acid tert-butyl ester (250 mg, 0.37 mmol) in toluene (4 mL) was added triethylamine (0.10 mL, 0.74 mmol) followed by dropwise addition of p-toluoyl chloride (0.049 mL, 0.37 mmol). The reaction mixture was heated to 80° C. for 18 h, then reflux for 4 h. The reaction mixture was allowed to cool to room temperature, quenched with saturated aqueous NaHCO₃ (10 mL) and diluted with CH₂Cl₂ (10 mL). The extracts were dried over MgSO₄, filtered and concentrated under reduced pressure. The residue was purified by silica gel chromatography (3:1 hexanes:ethyl acetate) to provide 235 mg (79%) of the title compound as a pale yellow powder. MS(ES+) m/e 794.2 [M+H]⁺.

c) (3-{(S)-1-[(R)-1-(3-Benzyl-7-chloro-4-oxo-3,4-dihydro-quinazolin-2-yl)-2-methyl-propyl]-2-p-tolyl-4,5-dihydro-1H-imidazol-4-yl}-propyl)-carbamic acid benzyl ester A solution of (1-([[1-(3-benzyl-7-chloro-4-oxo-3,4-dihydro-quinazolin-2-yl)-2-methyl-propyl]-(1-p-tolyl-methanoyl)-amino]-methyl}-4-benzyloxycarbonylamino-butyl)-carbamic acid tert-butyl ester (235 mg, 0.37 mmol) in CH₂Cl₂/TFA (4:1, 5 mL) was stirred at room temperature overnight. The reaction mixture was concentrated under reduced pressure and the residue was diluted with CH₂Cl₂ (10 mL) and washed with saturated aqueous NaHCO₃ (10 mL). The aqueous layer was extracted with CH₂Cl₂ and the combined extracts were dried over MgSO₄, filtered and concentrated under reduced pressure. The residue was diluted with THF (10 mL) and saturated aqueous NaHCO₃ (1 mL). The mixture was stirred at room temperature for 10 days, diluted with ether (20 mL) and washed with brine. The aqueous layer was extracted with two 10 mL portions of EtOAc and the combined extracts were dried over MgSO₄, filtered and concentrated under reduced pressure. The residue was purified by silica gel chromatography (19:1 CH₂Cl₂:MeOH) to provide 81 mg (40%) of the title compound as a pale white powder. MS(ES+) m/e 675.6 [M+H]⁺.

Example 25

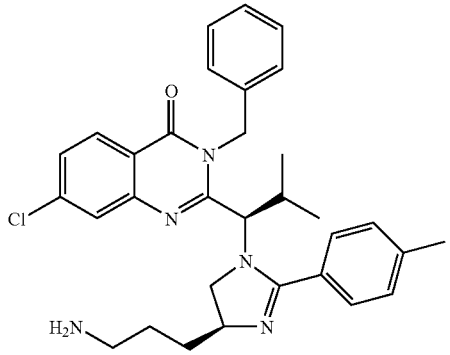

2-{(R)-1-[(S)-4-(3-Amino-propyl)-2-p-tolyl-4,5-dihydro-imidazol-1-yl]-2-methyl-propyl}-chloro-3H-quinazolin-4-one (3-{(S)-1-[(R)-1-(3-Benzyl-7-chloro-4-oxo-3,4-dihydro-quinazolin-2-yl)-2-methyl-propyl]-2-p-tolyl-4,5-dihydro-1H-imidazol-4-yl}-propyl)-carbamic acid benzyl ester (65.0 mg, 0.096 mmol) was dissolved in a solution of HBr in AcOH (30% by weight, 5 mL). After 45 min, the reaction mixture was concentrated under reduced pressure. The residue was diluted with toluene (2 mL) and concentrated under reduced pressure. The residue was then diluted with $CH_2Cl_2$ (10 mL) and washed with 1N NaOH (10 mL). The aqueous layer was extracted with $CH_2Cl_2$ (3×10 mL) and the combined extracts were dried over $MgSO_4$, filtered and concentrated under reduced pressure. The residue was purified by silica gel chromatography (92:7:1 $CH_2Cl_2$:MeOH:$NH_4OH$) to provide 30.0 mg (57%) of the title compound as an off-white powder. MS(ES+) m/e 542.2 $[M+H]^+$.

Example 26

Inhibition of Cellular Viability in Tumor Cell Lines Treated with KSP Inhibitors.r Materials and Solutions:
  Cells: SKOV3, Ovarian Cancer (human).
  Media: Phenol Red Free RPMI+5% Fetal Bovine Serum+2 mM L-glutamine.
  Colorimetric Agent for Determining Cell Viability: Promega MTS tetrazolium compound.
  Control Compound for max cell kill: Topotecan, 1 µM.

Procedure: Day 1—Cell Plating:

Adherent SKOV3 cells are washed with 10 mLs of PBS followed by the addition of 2 mLs of 0.25% trypsin and incubation for 5 minutes at 37° C. The cells are rinsed from the flask using 8 mL of media (phenol red-free RPMI+5% FBS) and transferred to fresh flask. Cell concentration is determined using a Coulter counter and the appropriate volume of cells to achieve 1000 cells/100 µL is calculated. 100 µL of media cell suspension (adjusted to 1000 cells/100 µL) is added to all wells of 96-well plates, followed by incubation for 18 to 24 hours at 37° C., 100% humidity, and 5% $CO_2$, allowing the cells to adhere to the plates.

Procedure: Day 2—Compound Addition:

To one column of the wells of an autoclaved assay block are added an initial 2.5 µL of test compound(s) at 400× the highest desired concentration. 1.25 µL of 400× (400 µM) Topotecan is added to other wells (optical density's from these wells are used to subtract out for background absorbance of dead cells and vehicle). 500 µL of media without DMSO are added to the wells containing test compound, and 250 µL to the Topotecan wells. 250 µL of media +0.5% DMSO is added to all remaining wells, into which the test compound(s) are serially diluted. By row, compound-containing media is replica plated (in duplicate) from the assay block to the corresponding cell plates. The cell plates are incubated for 72 hours at 37° C., 100% humidity, and 5% $CO_2$.

Procedure: Day 4—MTS Addition and OD Reading:

The plates are removed from the incubator and 40 µl MTS/PMS is added to each well. Plates are then incubated for 120 minutes at 37° C., 100% humidity, 5% $CO_2$, followed by reading the ODs at 490 nm after a 5 second shaking cycle in a ninety-six well spectrophotometer.

Data Analysis

The normalized % of control (absorbance-background) is calculated and an XLfit is used to generate a dose-response curve from which the concentration of compound required to inhibit viability by 50% is determined. The compounds of the present invention show activity when tested by this method as described above.

Example 27

Enantiomer Separation

In general, the procedures described above can be used to prepare substantially pure or enriched R- or S-enantiomers by selected a starting amino acid of the appropriate R- or S-configuration. More preferred compounds of the invention are those of the R-configuration: at the stereogenic center to which $R^2$ is attached. An R:S mixture can be separated into its constituent pure enantiomers by methods well known to those skilled in the art. These include the formation and separation of diastereomeric derivatives such as those formed by reaction with an optically pure acid such as dibenzoyltartaric acid. Alternatively, separation can be accomplished by chiral chromatography, for example, using the following conditions:
  Column: Chiralcel OD 20×250 mm;
  Sample loaded ~100 mg $mL^{-1}$ in 1:2 ethanol:hexane containing 0.01% isopropylamine;
  Chromatography conditions: isocratic elution with 1:2 ethanol:hexane containing 0.01% isopropylamine at a flow rate of 15 mL $min^{-1}$;
  UV detection at 254 nm.

For example, an enriched 3:1 R:S mixture of enantiomers was separated into its pure enantiomers by chiral chromatography with the following conditions: Chiralpak AD, 250×4.6 mm (Diacel Inc.). Sample—22.5 mg/ml in 1:1 i-PrOH:hexanes. Conditions—40 min at isocratic 50% i-PrOH in Hexanes, (S)-enantiomer elutes at 18.35 min. (R)-enantiomer elutes at 26.87 min. The (R)-enantiomer was significantly more potent than the (S)-enantiomer.

Example 28

Monopolar Spindle Formation Following Application of a KSP Inhibitor

Human tumor cells Skov-3 (ovarian) were plated in 96-well plates at densities of 4,000 cells per well, allowed to adhere for 24 hours, and treated with various concentrations of the pyridmidinone derivatives for 24 hours. Cells were fixed ill 4% formaldehyde and stained with antitubulin antibodies (subsequently recognized using fluorescently-labeled secondary antibody) and Hoechst dye (which stains DNA).

Visual inspection revealed that the compounds caused cell cycle arrest in the prometaphase stage of mitosis. DNA was condensed and spindle formation had initiated, but arrested cells uniformly displayed monopolar spindles, indicating that there was an inhibition of spindle pole body separation. Microinjection of anti-KSP antibodies also causes mitotic arrest with arrested cells displaying monopolar spindles.

Example 29

Inhibition of Cellular Proliferation in Tumor Cell Lines Treated with KSP Inhibitors.

Cells were plated in 96-well plates at densities from 1000-2500 cells/well of a 96-well plate and allowed to adhere/grow for 24 hours. They were then treated with various concentrations of drug for 48 hours. The time at which compounds are added is considered $T_0$. A tetrazolium-based assay using the reagent 3-(4,5-dimethylthiazol-2-yl)-5-(3-carboxymethoxyphenyl)-2-(4-sulfophenyl)-2H-tetrazolium (MTS) (U.S. Pat. No. 5,185,450) (see Promega product catalog #G3580, CellTiter 96® $AQ_{usous}$ One Solution Cell Proliferation Assay) was used to determine the number of viable cells at $T_0$ and the number of cells remaining after 48 hours compound exposure. The number of cells remaining after 48 hours was compared to the number of viable cells at the time of drug addition, allowing for calculation of growth inhibition.

The growth over 48 hours of cells in control wells that had been treated with vehicle only (0.25% DMSO) is considered 100% growth and the growth of cells in wells with compounds is compared to this.

A $Gi_{50}$ was calculated by plotting the concentration of compound in μM vs the percentage of cell growth in treated wells. The $Gi_{50}$ calculated for the compounds is the estimated concentration at which growth is inhibited by 50% compared to control. i.e., the concentration at which:

$$100 \times [(\text{Treated}_{48} - T_0)/(\text{Control}_{48} - T_0)] = 50$$

wherein $\text{Treated}_{48}$ is the value at 48 hours for the treated cells and $\text{Control}_{48}$ is the value at 48 hours for the control population.

All concentrations of compounds are tested in duplicate and controls are averaged over 12 wells. A very similar 96-well plate layout and $Gi_{50}$ calculation scheme is used by the National Cancer Institute (see Monks, et al., J. Natl. Cancer Inst. 83:757-766 (1991)). However, the method by which the National Cancer Institute quantitates cell number does not use MTS, but instead employs alternative methods.

Compounds of examples above inhibited cell proliferation in human ovarian tumor cell lines (SKOV-3).

Example 30

Calculation of $IC_{50}$:

Measurement of a compound's $IC_{50}$ for KSP activity uses an ATPase assay. The following solutions are used: Solution 1 consists of 3 mM phosphoenolpyruvate potassium salt (Sigma P-7127), 2 mM ATP (Sigma A-3377), 1 mM IDTT (Sigma D-9779), 5 μM paclitaxel (Sigma T-7402), 10 ppm antifoam 289 (Sigma A-8436), 25 mM Pipes/KOH pH 6.8 (Sigma P6757), 2 mM MgCl2 (VWR JT400301), and 1 mM EGTA (Sigma E3889). Solution 2 consists of 1 mM NADH (Sigma N8129), 0.2 mg/ml BSA (Sigma A7906), pyruvate kinase 7 U/ml, L-lactate dehydrogenase 10 U/ml (Sigma P0294), 100 nM KSP motor domain, 50 μg/ml microtubules, 1 mM DTT (Sigma D9779), 5 μM paclitaxel (Sigma T-7402), 10 ppm antifoam 289 (Sigma A-8436), 25 mM Pipes/KOH pH 6.8 (Sigma P6757), 2 mM MgCl2 (VWR JT4003-01), and 1 mM EGTA (Sigma E3889). Serial dilutions (8-12 two-fold dilutions) of the compound are made in a 96-well microtiter plate (Corning Costar 3695) using Solution 1. Following serial dilution each well has 50 μl of Solution 1. The reaction is started by adding 50 μl of solution 2 to each well. This may be done with a multichannel pipettor either manually or with automated liquid handling devices. The microtiter plate is then transferred to a microplate absorbance reader and multiple absorbance readings at 340 mm are taken for each well in a kinetic mode. The observed rate of change, which is proportional to the ATPase rate, is then plotted as a function of the compound concentration. For a standard $IC_{50}$ determination the data acquired is fit by the following four parameter equation using a nonlinear fitting program (e.g., Grafit 4):

$$y = \frac{\text{Range}}{1 + \left(\frac{x}{IC_{50}}\right)^s} + \text{Background}$$

where y is the observed rate and x is the compound concentration.

What is claimed is:

1. A method of inhibiting Kinesin Spindle Protein (KSP) which comprises contacting said KSP in vitro with an effective amount of a compound chosen from:
compounds having the structure

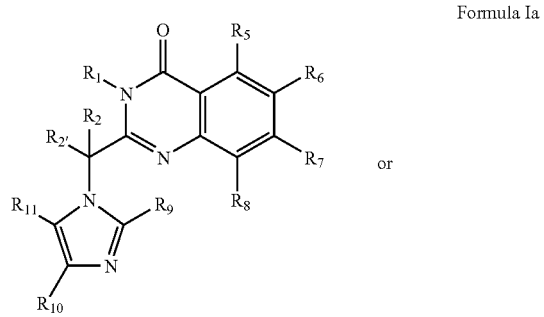

Formula Ia or

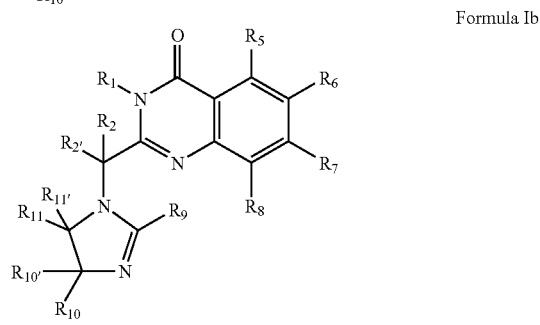

Formula Ib wherein:

$R_1$ is chosen from hydrogen, optionally substituted alkyl-, optionally substituted aryl-, optionally substituted aralkyl-, optionally substituted heteroaryl-, and optionally substituted heteroaralkyl-;

$R_2$ and $R_2'$ are independently chosen from hydrogen, optionally substituted alkyl-, optionally substituted aryl-, optionally substituted aralkyl-, optionally substituted heteroaryl-, and optionally substituted heteroaralkyl-; or $R_2$ and $R_2'$ taken together form an optionally substituted 3- to 7-membered ring;

$R_5$, $R_6$, $R_7$ and $R_8$ are independently chosen from hydrogen, optionally substituted alkyl-, optionally substituted alkoxy, halogen, hydroxyl-, nitro, cyano, dialkylamino, alkylsulfonyl-, alkylsulfonamido, alkylthio, carboxyalkyl-, carboxamido, aminocarbonyl-, optionally substituted aryl-, optionally substituted aryloxy, optionally substituted heteroaryl-, and optionally substituted heteroaryloxy;

$R_9$ is chosen from hydrogen, optionally substituted alkyl-, optionally substituted aryl-, optionally substituted aralkyl-, and optionally substituted heteroaryl-; and $R_{10}$, $R_{10'}$, $R_{11}$, and $R_{11'}$ are independently hydrogen, optionally substituted alkyl-, optionally substituted aryl-, or optionally substituted aralkyl-, and pharmaceutically acceptable salts of a compound of Formula Ia or Ib.

2. A method according to claim 1, wherein $R_1$ is selected from hydrogen, optionally substituted $C_1$-$C_8$ alkyl-, optionally substituted aryl-, optionally substituted heteroaryl-, optionally substituted aryl-$C_1$-$C_4$-alkyl-, and optionally substituted heteroaryl-$C_1$-$C_4$-alkyl-.

3. A method according to claim 2, wherein $R_1$ is selected from hydrogen, optionally substituted $C_1$-$C_4$ alkyl-, optionally substituted phenyl-$C_1$-$C_4$-alkyl-, optionally substituted naphthalenylmethyl-, optionally substituted phenyl-, and naphthyl-.

4. A method according to claim 3, wherein $R_1$ is optionally substituted phenyl-$C_1$-$C_4$-alkyl-, optionally substituted heteroaryl-$C_1$-$C_4$-alkyl-, or naphthalenylmethyl-.

5. A method according to claim 4, wherein $R_1$ is benzyl-.

6. A method according to claim 1, wherein $R_2$ is hydrogen and $R_2$ is optionally substituted $C_1$-$C_4$ alkyl-.

7. A method according to claim 6, wherein $R_2$ is chosen from methyl-, ethyl-, propyl-, butyl-, methylthioethyl-, methylthiomethyl-, aminobutyl-, (CBZ)aminobutyl-, cyclohexylmethyl-, benzyloxymethyl-, methylsulfanylethyl-, methylsulfanylmethyl-, and hydroxymethyl-, and $R_{2'}$ is hydrogen.

8. A method according to claim 7, wherein $R_{2'}$ is hydrogen and $R_2$ is ethyl- or propyl-.

9. A method according to claim 8, wherein $R_2$ is i-propyl-.

10. A compound method according to claim 1, wherein $R_5$, $R_6$, $R_7$, and $R_8$ are independently chosen from hydrogen, hydroxyl, halogen, $C_1$-$C_4$ alkyl-, $C_1$-$C_4$ alkoxy, and cyano.

11. A method according to claim 10, wherein $R_5$, $R_6$, $R_7$, and $R_8$ are methoxy, hydrogen or halo.

12. A method according to claim 11, wherein only one of $R_5$, $R_6$, $R_7$, and $R_8$ is not hydrogen.

13. A method according to claim 1, wherein $R^9$ is hydrogen; $C_1$-$C_4$ alkyl; substituted $C_1$-$C_4$ alkyl-; aryl-; substituted aryl-; aryl-$C_1$-$C_4$-alkyl-; heteroaryl-; substituted heteroaryl-; or substituted aryl-$C_1$-$C_4$-alkyl-.

14. A method according to claim 13, wherein $R_9$ is hydrogen; methyl-; ethyl-; propyl-; phenyl-; tolyl-; ethylphenyl-; halophenyl-; acetylaminophenyl-; cyanophenyl-; halomethylphenyl-; polyhalophenyl-; methyoxymethyl-; methoxyethyl-; methoxyphenyl-; dimethoxyphenyl-; methylenedioxyphenyl-; trifluoromethylphenyl-; furyl-; thiophenyl-; pyridinyl-; halomethylpyridinyl-; isoxazolyl-; methylisoxzolyl-; dimethylaminophenyl-; diethylaminophenyl-; isopropylphenyl-; or quinoxalinyl-.

15. A method according to claim 1, wherein $R_{10}$ and $R_{10'}$ are independently selected from the group consisting of hydrogen; hydroxymethyl-; aminomethyl-; acetylaminomethyl-; (carboxymethyl-amino)-methyl-; aminoethyl-; acetylaminoethyl-; (carboxymethyl-amino)-ethyl-; hydroxyethyl-; aminopropyl-; acetylaminopropyl-; (carboxymethyl-amino)-propyl-; hydroxypropyl-; methyl-; ethyl-; and propyl-.

16. A method according to claim 1, wherein $R_{11}$ and $R_{11'}$ are independently selected from the group consisting of hydrogen and optionally substituted $C_1$-$C_4$ alkyl-.

17. A method according to claim 16, wherein $R_{11}$ and $R_{11'}$ are hydrogen.

18. A method according to claim 1, wherein the compound is a compound of Formula Ia and $R_1$ is benzyl-, halobenzyl-, methoxybenzyl-, cyanobenzyl-, or naphthylmethyl-; $R_2$ is chosen from ethyl- and propyl-; $R_{2'}$ is hydrogen; $R_5$ is hydrogen; $R_6$ is hydrogen; $R_7$ is halogen; $R_8$ is hydrogen; and $R_9$ is substituted phenyl-; $R_{9'}$ is hydrogen; $R_{10}$ is methyl-, hydrogen, or amino lower-alkyl-; and $R_{11}$ is hydrogen.

19. A method according to claim 1, wherein the compound is a compound of Formula Ib and according to claim 1, wherein $R_1$ is benzyl-, halobenzyl-, methoxybenzyl-, cyanobenzyl-, or naphthylmethyl-; $R_2$ is chosen from ethyl- and propyl-; $R_{2'}$ is hydrogen; $R_5$ is hydrogen; $R_6$ is hydrogen; $R_7$ is halogen; $R_8$ is hydrogen; and $R_9$ is substituted phenyl-; $R_{9'}$ is hydrogen; $R_{10}$ and $R_{10'}$ are methyl-, hydrogen, or amino lower-alkyl-; and $R_{11}$ and $R_{11'}$ are hydrogen.

20. A method according to claim 1 wherein $R_2$ and $R_{2'}$ are each attached to a stereogenic center having an R-configuration.

* * * * *